US008728489B2

(12) United States Patent
Apelian et al.

(10) Patent No.: US 8,728,489 B2

(45) Date of Patent: May 20, 2014

(54) IMMUNOTHERAPY FOR CHRONIC HEPATITIS C VIRUS INFECTION

(75) Inventors: David Apelian, Boonton Township, NJ (US); Richard C. Duke, Denver, CO (US); Alex Franzusoff, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 451 days.

(21) Appl. No.: 13/119,760

(22) PCT Filed: Sep. 18, 2009

(86) PCT No.: PCT/US2009/057535

§ 371 (c)(1), (2), (4) Date: Jun. 30, 2011

(87) PCT Pub. No.: WO2010/033841

PCT Pub. Date: Mar. 25, 2010

(65) Prior Publication Data

US 2011/0256098 A1 Oct. 20, 2011

Related U.S. Application Data

(60) Provisional application No. 61/098,306, filed on Sep. 19, 2008, provisional application No. 61/110,003, filed on Oct. 31, 2008, provisional application No. 61/171,373, filed on Apr. 21, 2009, provisional application No. 61/231,901, filed on Aug. 6, 2009.

(51) Int. Cl.

*A61K 39/29* (2006.01)
*A61K 45/00* (2006.01)
*C12N 1/00* (2006.01)
*C12N 1/19* (2006.01)

(52) U.S. Cl.

USPC .................. 424/228.1; 424/192.1; 424/278.1; 424/93.1; 424/93.51; 435/69.3; 435/69.7; 435/254.1; 435/255.1

(58) Field of Classification Search

None

See application file for complete search history.

(56) References Cited

U.S. PATENT DOCUMENTS

| | | | |
|---|---|---|---|
| 4,775,622 | A | 10/1988 | Hitzeman et al. |
| 5,413,914 | A | 5/1995 | Franzusoff |
| 5,523,215 | A | 6/1996 | Cousens et al. |
| 5,585,258 | A | 12/1996 | Houghton et al. |
| 5,641,654 | A | 6/1997 | Maki et al. |
| 5,683,864 | A | 11/1997 | Houghton et al. |
| 5,830,463 | A | 11/1998 | Duke et al. |
| 5,858,378 | A | 1/1999 | Bostwick |
| 5,871,903 | A | 2/1999 | Miyamura et al. |
| 5,919,651 | A | 7/1999 | Hitzeman et al. |
| 5,930,463 | A | 7/1999 | Park |
| 5,961,978 | A | 10/1999 | Gaudernack et al. |
| 6,027,729 | A | 2/2000 | Houghton et al. |
| 6,071,693 | A | 6/2000 | Cha et al. |
| 6,074,816 | A | 6/2000 | Houghton et al. |
| 6,090,546 | A | 7/2000 | Breivik et al. |
| 6,121,020 | A | 9/2000 | Selby et al. |
| 6,187,307 | B1 | 2/2001 | Cohen |
| 6,194,140 | B1 | 2/2001 | Houghton et al. |
| 6,284,249 | B1 | 9/2001 | Barban |
| 6,326,171 | B1 | 12/2001 | Selby et al. |
| 6,361,969 | B1 | 3/2002 | Galeotti |
| 6,521,423 | B1 | 2/2003 | Houghton et al. |
| 6,558,951 | B1 | 5/2003 | Tomai et al. |
| 6,562,346 | B1 | 5/2003 | Paliard et al. |
| 6,613,333 | B1 | 9/2003 | Leroux-Roels et al. |
| 6,747,135 | B1 | 6/2004 | Nolan et al. |
| 6,759,046 | B1 | 7/2004 | Gaudernack et al. |
| 6,861,057 | B2 | 3/2005 | Gaudernack et al. |
| 6,890,737 | B1 | 5/2005 | Maertens et al. |
| 6,986,892 | B1 | 1/2006 | Coit et al. |
| 6,989,892 | B2 | 1/2006 | White |
| 7,033,805 | B2 | 4/2006 | Houghton et al. |
| 7,048,930 | B2 | 5/2006 | Bosman et al. |
| 7,052,696 | B2 | 5/2006 | Fields et al. |

(Continued)

FOREIGN PATENT DOCUMENTS

| | | |
|---|---|---|
| FR | 2486400 | 1/1982 |
| WO | WO 92/22571 | 12/1992 |

(Continued)

OTHER PUBLICATIONS

Chou et al. "Immunity to TCR Peptides in Multiple Sclerosis," Journal of Immunology, Mar. 1994, vol. 152, No. 5, pp. 2520-2529.

(Continued)

*Primary Examiner* — Michelle S Horning

(74) *Attorney, Agent, or Firm* — Sheridan Ross P.C.

(57) ABSTRACT

Disclosed are uses of immunotherapeutic compositions in combination with Standard of Care (SOC), or interferon therapy combined with anti-viral therapy, for the improved treatment of chronic hepatitis C virus (HCV) infection and related conditions, including liver function. The compositions, kits and uses of the invention, as compared to the use of SOC therapy alone: improves the rate of early response to therapy as measured by early virologic markers (e.g., RVR and EVR), enlarges the pool of patients who will have sustained responses to therapy over the long term, offers shortened courses of therapy for certain patients, enables "rescue" of patients who are non-responders or intolerant to SOC therapy, improves liver function and/or reduces liver damage in patients, and enables the personalization of HCV therapy for a patient, which can result in dose sparing, improved patient compliance, reduced side effects, and improved long term therapeutic outcomes.

19 Claims, 23 Drawing Sheets

(56) References Cited

U.S. PATENT DOCUMENTS

| | | | | |
|---|---|---|---|---|
| 7,078,416 | B2 | 7/2006 | Gaudernack et al. | |
| 7,083,787 | B2 | 8/2006 | Duke et al. | |
| 7,105,303 | B2 | 9/2006 | Ralston et al. | |
| 7,166,426 | B2 | 1/2007 | Arcangel et al. | |
| 7,192,927 | B2 | 3/2007 | Gaudernack et al. | |
| 7,238,356 | B2 | 7/2007 | Bosman et al. | |
| 7,314,925 | B2 | 1/2008 | Sablon et al. | |
| 7,439,042 | B2 * | 10/2008 | Duke et al. | 435/69.7 |
| 7,465,454 | B2 | 12/2008 | Franzusoff et al. | |
| 7,563,447 | B2 | 7/2009 | Franzusoff et al. | |
| 7,595,060 | B2 | 9/2009 | Duke et al. | |
| 7,625,569 | B2 * | 12/2009 | Duke et al. | 424/228.1 |
| 7,632,511 | B2 * | 12/2009 | Duke et al. | 424/228.1 |
| 8,007,816 | B2 * | 8/2011 | Duke et al. | 424/228.1 |
| 8,388,980 | B2 * | 3/2013 | Duke et al. | 424/228.1 |
| 2002/0044948 | A1 | 4/2002 | Khleif et al. | |
| 2002/0169125 | A1 | 11/2002 | Leung et al. | |
| 2003/0035810 | A1 | 2/2003 | Caplan | |
| 2003/0064499 | A1 | 4/2003 | Houghton et al. | |
| 2004/0009937 | A1 | 1/2004 | Chen et al. | |
| 2004/0126395 | A1 | 7/2004 | Maertens et al. | |
| 2004/0138204 | A1 | 7/2004 | Harrington | |
| 2004/0151735 | A1 | 8/2004 | Maertens et al. | |
| 2004/0191270 | A1 | 9/2004 | Drane et al. | |
| 2005/0013828 | A1 | 1/2005 | George et al. | |
| 2005/0037018 | A1 | 2/2005 | Maertens et al. | |
| 2005/0074465 | A1 | 4/2005 | Houghton | |
| 2008/0182895 | A1 | 7/2008 | Howe et al. | |
| 2009/0098154 | A1 | 4/2009 | Franzusoff et al. | |
| 2009/0142366 | A1 | 6/2009 | Franzusoff et al. | |
| 2009/0142367 | A1 | 6/2009 | Franzusoff et al. | |
| 2009/0304741 | A1 | 12/2009 | Duke et al. | |
| 2010/0034840 | A1 | 2/2010 | Apelian et al. | |
| 2010/0111912 | A1 | 5/2010 | Apelian et al. | |
| 2010/0150963 | A1 | 6/2010 | Duke et al. | |
| 2010/0189749 | A1 | 7/2010 | Franzusoff et al. | |

FOREIGN PATENT DOCUMENTS

| | | |
|---|---|---|
| WO | WO 93/17110 | 9/1993 |
| WO | WO 01/38360 | 5/2001 |
| WO | WO 02/39951 | 5/2002 |
| WO | WO 02/086100 | 10/2002 |
| WO | WO 2004/005473 | 1/2004 |
| WO | WO 2004/046175 | 6/2004 |
| WO | WO 2004/046176 | 6/2004 |
| WO | WO 2004/058157 | 7/2004 |

OTHER PUBLICATIONS

MacDonald et al., "CD4 T Helper Type 1 and Regulatory T Cells Induced against the Same Epitopes on the Core Protein in Hepatitis C Virus-Infected Persons," Journal of Infectious Diseases, 2002, vol. 185, Iss. 6, pp. 720-727.

Shirai et al., "An Epitope in Hepatitis C Virus Core Region Recognized by Cytotoxic T Cells in Mice and Humans," Journal of Virology, 1994, vol. 68, No. 5, pp. 3334-3342.

Acosta-Rivero et al. "Processing of the Hepatitis C virus precursor protein expressed in the methylotrophic yeast *Pichia pastoris*," Biochemical and Biophysical Research Communications, 2002, vol. 295, pp. 81-84.

Adams et al. "Hybrid Ty Virus-Like Particles," International Reviews of Immunology, 1994, vol. 11, pp. 133-141.

Allsopp et al. "Comparison of Numerous delivery systems for the induction of cytotoxic T lymphocytes by immunization," European Journal of Immunology, 1996, vol. 26, No. 8, pp. 1951-1959.

Bachmann, et al. "In vivo versus in vitro assays for assessment of T- and B-cell function". Current Opinion in Immunology, Jun. 1994, vol. 6, pp. 320-326.

Baker et al. "Reconstitution of SEC Gene Product-Dependent Intercompartmental Protein Transport," Cell, Jul. 29, 1988, vol. 54, pp. 335-344.

Bizzini et al. "Use of live *Saccharomyces cerevisiae* cells as a biological response modifier in experimental infections." FEMS Microbiology Immunology, 1990, vol. 64, pp. 155-168.

Bourdette et al. "Immunity to TCR Peptides in Multiple Sclerosis," Journal of Immunology, 1994, vol. 15, No. 2, pp. 2510-2519.

Brake et al. "a-Factor-directed synthesis and secretion of mature foreign proteins in *Saccharomyces cerevisiae*,"Proc. Natl. Acad. Sci. USA, Aug. 1984, vol. 81, pp. 4642-4646.

Brossier et al. "Functional Analysis of the Carboxy-Terminal Domain of *Bacillus anthracis* Protective Antigen," Infection and Immunity, Feb. 1999, vol. 67, No. 2, pp. 964-967.

Brown "Gene Therapy 'Oversold' by Researchers, Journalists NIH Advisers Cite Nearly Uniform Failure," The Washington Post, Dec. 8, 1995, 1 page.

Caumont et al., "Expression of functional HIV-1 integrase in the yeast *Saccharomyces cerevisiae* leads to the emergence of a lethal phenotype: potential use for inhibitor screening." Current Genetics, 1996. vol. 29, No. 6, p. 503-510.

Chien et al. "Diagnosis of hepatitis C virus (HCV) infection using an immunodminant chimeric polyprotein to capture circulating antibodies: Reevaluation of the role of HCV in liver disease," Proc. Natl. Acad Sci. USA., Nov. 1992, vol. 89, pp. 10011-10015.

Chou et al. "Immuniy to TCR Peptides in Multiple Sclerosis," Journal Immunology, vol. 152, pp. 2520-2529.

Cocquerel et al., "Charged Residues in the Transmembran Domains of Hepatitis C Virus Glycoproteins Playa Major Role in the Processing, Subcellular Localization, and Assembly ofThese Envelope Proteins," J. Virology, 2000, vol. 74, No. 8, pp. 3623-3633.

Coghlan "Gene dream fades away". New Scientist, Nov. 25, 1995, vol. 145, pp. 14-15.

Cohen "Will Media Reports KO Upcoming Real-Life Trials?" Science, Jun. 1994, vol. 264, p. 1660.

Cohen "U.S. Panel Votes to Delay Real-World Vaccine Trials," Science, Jun. 24, 1994, vol. 264, p. 1839.

Davies et al. "Targeted alterations in yeast artificial chromosomes for inter-species gene transfer," Nucleic Acids Research, 1992, vol. 20, No. 11, pp. 2693-2698.

Demmer et al. "Simultaneous Transfer of Four Functional Genes from the HLA Class II Region into Mammalian Cells by Fusion with Yeast Spheroplasts Carrying an Artificial Chromosome," Journal of Immunology, Jun. 15, 1993, vol. 150, No. 12, pp. 5371-5378.

Di Bisceglie et al., Combination of interferon and ribavirin in chronic hepatitis C: re-treatment of nonresponders to interferon, Hepatology, vol. 33 No. 3, pp. 704-707 (Mar. 2001).

Diepolder et al. "Immunodominant CD4+ T-Cell Epitope within Nonstructural Protein 3 in Acute Hepatitis C Virus Infection," Journal of Virology, Aug. 1997, vol. 71, No. 8, pp. 6011-6019.

Duenas-Carrera Santiago: "DNA vaccination against hepatitis C" Current Opinion in Molecular Therapeutics, Current Drugs, London, GB, vol. 6, No. 2, Apr. 1, 2004, pp. 146-150.

Engelhardt et al. "Prolonged Transgene Expression in Cotton Rat Lung with Recombinant Adenoviruses Defective in E2a," Human Gene Therapy, Oct. 1994, vol. 5, pp. 1217-1229.

Everson Gregory T et al: "Interim results from a randomized, double-blind, placebo-controlled phase 1b study in subjects with chronic HCV after treatment with GI-5005, a yeast-based HCV immunotherapy targeting NS3 and core proteins" Hepatology, vol. 44, No. 4, Suppl. 1, Oct. 2006, pp. 697A-698A, XP002554459 & 57th Annual Meeting of the American-Association-For-The-Study-Of-Live R-Diseases; Boston, MA, USA; October 27-31, 2006 ISSN: 0270-9139.

Fattal-German et al. "Assessment of the Anti-Viral Effect of a Short-term Oral Treatment of Mice with Live *Saccharomyces Cerevisiae* Cells," Develop. Biol. Standard., 1992, vol. 77, pp. 115-120.

Forns Xavier et al: "The challenge of developing a vaccine against hepatitis C virus." J. Hepatol., Nov. 2002, vol. 37, No. 5, Nov. 2002, pp. 684-695.

Franzusoff, A. et al. (Apr. 1, 2005). "Yeasts Encoding Tumour Antigens in Cancer Immunotherapy," Expert Opinion on Biological Therapy 5(4):565-575.

Franzusoff et al. "Biochemical and Genetic Definition of the Cellular Protease Required for HIV-1 gp160 Processing," Journal of Biol Chem., Feb. 17, 1995, vol. 270, No. 7, pp. 3154-3159.

(56) References Cited

OTHER PUBLICATIONS

Fujita et al. "Studies in the development of *Japanese encephalitis* vaccine: expression of virus envelope glycoprotein V3(E) gene in yeast," Bulletin of the World Health Organization, 1987, vol. 65, No. 3, pp. 303-308.
Gallinari P. et al: "Multiple enzymatic activities associated with recombinant NS3 protein of Hepatitis C virus" J. Virol., vol. 72, No. 8, Aug. 1, 1998, pp. 6758-6769.
Garber et al. "AIDS Vaccine Development: the Long and Winding Road," AIDS Reviews, 2003, vol. 5, No. 3, pp. 131-139.
GENPEPT AAB67036, "polyprotein [Hepatitis C virus strain H77]", Aug. 16, 1997.
Gnirke et al. "Cloning and in vivo expression of the human GART gene using yeast artificial chromosomes," The EMBO Journal, 1991, vol. 10, No. 7, pp. 1629-1634.
Gobin et al. "Transfer of yeast artificial chromosomes into mammalian cells and comparative study of their integrity," Gene, 1995, vol. 163, pp. 27-33.
Haller Aurelia et al: "Whole recombinant yeast-based immunotherapy for treatment of chronic hepatitis C infection induces dose-dependent T cell responses and therapeutic effects without vector neutralization" Hepatology, vol. 42, No. 4, Suppl. 1, Oct. 2005, p. 249A, XP002554457 & 56th Annual Meeting of The American-Association-for-The-Study-Of-Live R-Diseases; San Francisco, CA, USA; Nov. 11-15, 2005 ISSN: 0270-9139.
Haller et al: "Whole recombinant yeast-based immunotherapy induces potent T cell responses targeting HCV NS3 and Core proteins" Vaccine, Butterworth Scientific. Guildford, GB, vol. 25, No. 8, Jan. 23, 2007, pp. 1452-1463, XP005829882 ISSN: 0264-410X.
Han et al., "Identification of the protease domain in NS3 of hepatitis C virus," Journal of General Virology, vol. 76 No. 4, pp. 985-993 (Apr. 1995).
Hatsuyama et al. "Direct Transfer of Plasmid DNA from Intact Yeast Spheroplasts into Plant Protoplasts," Plant Cell Physiology, 1994, vol. 35, No. 1, pp. 93-98.
Hitomi et al., "High efficiiency prokaryotic expression and purification of a portion of Hepatitis C Core Protein and analysis of the immune response to recombinant protein in BALB/c mice," Viral Immunology, vol. 8 No. 2, pp. 109-119 (1995).
Isoyama et al., "The core protein of hepatitis C virus is imported into the nucleus by transport receptor Kap123p but inhibits Kap121p-dependent nuclear import of yeast AP1-like transcription factor in yeast cells," J Biol Chem., Oct. 2002, vol. 277(42), pp. 39634-39641.
Kaur et al. "HIV Pathogenesis and Vaccine Development," International AIDS Society-USA Topics in HIV Medicine, 2003, vol. 11, No. 3, pp. 76-85.
Ketner et al. "Efficient manipulation of the human adenovirus genome as an infectious yeast artificial chromosome clone," Proc. Natl. Acad. Sci. USA, Jun. 1994, vol. 91, pp. 6186-6190.
Khu et al. "Hepatitis C virus non-structural protein NS3 interacts with LMP7, a component of the immunoproteasome, and affects its proteasome activity," Biochem. J., 2004, vol. 384, pp. 401-409.
Kurokohchi et al. "Use of Recombinant Protein to Identify a Motif-Negative Human Cytotoxic T-Cell Epitope Presented by HLA-A2 in the Hepatitis C Virus NS3 Region," Journal of Virology, Jan. 1996, vol. 70, No. 1, pp. 232-240.
Kyono et al., "Human eukaryotic initiation factor 4AII associates with hepatitis C virus NS5B protein in vitro," Biochem Biophys Res Commun, Apr. 2002, vol. 292(3), pp. 659-666.
Layton et al. "Induction of single and dual cytotoxic T-lymphocyte responses to viral proteins in mice using recombinant hybrid Ty-virus-like particles," Immunology, 1996, vol. 87, No. 2, pp. 171-178.
Lechmann et al. "Vaccine development for hepatitis C." Semin Liver Disease, 2000, vol. 20, No. 2, pp. 211-226 (Abstract).
Lu, Y. et al. (Aug. 1, 2004). "Mutation-Selective Tumor Remission with Ras-Targeted, Whole Yeast-Based Immunotherapy," Cancer Research, 64:5084-5088.
Markie et al."New Vector for Transfer of Yeast Artificial Chromosomes to Mammalian Cells," Somat. Cell Mol. Genet., 1993, vol. 19, No. 2, pp. 161-169.
Markland et al. "Purification and characterization of the NS3 serine protease domain of hepatitis C virus expressed in *Saccharomyces cerevisia*," Journal of General Virology., 1997, vol. 78, pp. 39-43.
Marshall, E. "Gene Therapy's Growing Pains," Science, vol. 269: 1050-1055, Aug. 25, 1995.
Martinez-Donato et al. "Expression and processing of hepatitis C virus structrural proteins in *Pichia pastoris* yeast," Biochemical and Biophysical Research Comm., 2006, vol. 342, pp. 625-631.
Matsui et al. "Induction of hepatitis C virus-specific cytotoxic T lymphocytes in mice by immuniziation with dendritic cells transduced with replication-defective recombinant adenovirus," Vaccine, 2002, vol. 21, pp. 211-220.
Moore et al. "Novel yeast-based vaccine 1-40, against HIV-SF2 gp160 promotes a cytotoxic 43-62 cell response." FASEB Journal (online), vol. 10. No. 6. 1996, p. A1473, ZP002186594, Joint.
Moulard et al. "Kex2p: A model for cellular endoprotease processing human immunodeficiency virus type 1 envelope glycoprotein precursor," European Journal of Biochemister, vol. 225, No. 2, 1994, pp. 565-572, XP001042234.
Mullen et al., 1994, Plant Physiol., 105:113 (Abstr. 606).
Mulligan, et al. "The Basic Science of Gene Therapy." Science, vol. 260, 926-930, May 14, 1993.
Mustilli et al. "Comparison of secretion of a hepatitis C virus glycoprotein in *Saccharomyces cerevisiae* and *Kluyveromyces lactis*," Res. Microbiol., 1999, vol. 150, pp. 179-187.
O'Brien et al. "Alternative modes of binding of proteins with tandem SH2 domains," Protein Science, 2000, vol. 9, pp. 570-579.
Pachnis et al. "Transfer of a yeast artificial chromosome carrying human DNA from *Saccharomyces cerevisiae* into mammalian cells," Proc. Natl. Acad. Sci. USA, Jul. 1990, vol. 87, pp. 5109-5113.
Paglia et al. "Murine Dendritic Cells Loaded in Vitro with Soluble Protein Prime Cytotoxic T Lymophocytes against Tumor Antigen In Vivo," J. of Experimental Medicine, Jan. 1996, vol. 183, No. 1, pp. 317-322.
Park et al., "Monitoring antibody titers to recombinant Core-NS3 fusion polypeptide is useful for evaluating hepatitis C virus infection and responses to interferon-alpha therapy." Journal of Korean medical science, Apr. 1999, vol. 14, No. 2, pp. 165-170.
Parolin et al. "Heterologous production of five Hepatitis C virus-derived antigens in three *Saccharomyces cerevisiae* host strains," Journal of Biotechnology, 2005, vol. 120, pp. 46-58.
Peterson et al. "Use of yeast artificial chromosomes (YACs) for studying control of gene expression: Correct regulation of the genes of a human beta-globin locus YAC following transfer to mouse erythroleukemia cell lines," Proc. Natl. Acad. Sci. USA, Dec. 1993, vol. 90 pp. 11207-11211.
Rabinovich et al. "Vaccine Technologies: View to the Future," Science, Sep. 1994, vol. 265, pp. 1401-1404.
Rosa et al. "A quantitative test to estimate neutralizing antibodies to the hepatitis C virus: Cytofluorimetric assessment of envelope glycoprotein 2 binding to target cells." Proc. Natl. Acad. Sci. USA, Mar. 1996, vol. 93, pp. 1759-1763.
Sanchez-Pescador et al. "Nucleotide Sequence and Expression of an AIDS-Associated Retrovirus (ARV-2)," Science, Feb. 1985, vol. 227, pp. 484-492.
Schiff Eugene R et al: "HCV-specific cellular immunity, RNA reductions, and normalization of ALT in chronic HCV subjects after treatment with GI-5005, a yeast-based immunotherapy targeting NS3 and Core: A randomized, double-blind, placebo controlled phase 1B study" Hepatology, vol. 46, No. 4, Suppl. S, Oct. 2007, p. 816A, XP002554458 & 58th Annual Meeting of the American-Association-For-The-Study-Of-Live R-Diseases; Boston, MA, USA; Nov. 2-6, 2007 ISSN: 0270-9139.
Schreuder et al. "Yeast expressing hepatitis B virus surface antigen determinants on its surface: implications for a possible oral vaccine," Vaccine, Apr. 1996, vol. 14, No. 5, pp. 383-388.
Schupper et al., 1993, Hepatology, 18(5):1055-1060 (Abstract Only).
Seong et al., "Overexpression and simple purification of a truncated immunologically reative GST-HCV core (1-123) fusion protein", Journal of Virological Methods, May 1996, vol. 59, Nos. 1-2, pp. 13-21.

(56) References Cited

OTHER PUBLICATIONS

Sousa et al. "Phagocytosis of Antigens by Langerhans Cells In Vitro," Journal of Experimental Medicine, Aug. 1993, vol. 178, No. 2, pp. 509-519.
Stern et al. "The Human Class II MHC Protein HLA-DR1 Assembles as Empty αβ Heterodimiers in the Absence of Antigenic Peptide," Cell, Feb. 7, 1992, vol. 68, pp. 465-477.
Stubbs et al., "Whole recombinant yeast vaccine activates dendritic cells and elicits protective cell-mediated immunity" Nature Medicine vol. 7, No. 5, May 1, 2001, pp. 625-629.
Suda et al. "Molecular Cloning and Expression of the Fas Ligand, a Novel Member of the Tumor Necrosis Factor Family," Cell, Dec. 17, 1993, vol. 75, pp. 1169-1178.
Vajdy, et al., "Hepatitis C virus polyprotein vaccine formulations capable of inducing broad antibody and cellular immune responses", Journal of General Virology, 2006, 87:2253-2262.
Valenzuela, et al. "Antigen engineering in yeast: Synthesis and assembly of hybrid hepatitis B surface antigen-Herpes simplex 1 gD particles," Bio/Technology, vol. 3, 323-326, Apr. 1985.
International Search Report for International (PCT) Patent Application No. PCT/US/09/57535, mailed Nov. 19, 2009.
Written Opinion for International (PCT) Patent Application No. PCT/US/09/57535, mailed Nov. 19, 2009.
International Preliminary Report on Patentability for International (PCT) Patent Application No. PCT/US09/57535, mailed Mar. 31, 2011 12 pages.
Habersetzer et al. "GI-5005, a yeast vector vaccine expressing an NS3-core fusion protein for chronic HCV infection," Current Opinion in Molecular Therapeutics, Aug. 2009, vol. 11, No. 4, pp. 456-462, XP009167081.
Extended Search Report for European Patent Application No. 09815294.5, dated Feb. 27, 2013 10 pages.

* cited by examiner

IMMUNOTHERAPY FOR CHRONIC HEPATITIS C VIRUS INFECTION

CROSS REFERENCE TO RELATED APPLICATION

This application is a national stage application under 35 U.S.C. 371 of PCT Application No. PCT/US2009/057535 having an international filing date of Sep. 18, 2009, which designated the United States, which PCT application claimed the benefit of U.S. Application Ser. No. 61/098,306, filed Sep. 19, 2008, U.S. Application Ser. No. 61/110,003, filed Oct. 31, 2008, U.S. Application Ser. No. 61/171,373, filed Apr. 21, 2009, and U.S. Application Ser. No. 61/231,901, filed Aug. 9, 2009, the entire disclosure of each of which is hereby incorporated herein by reference.

REFERENCE TO SEQUENCE LISTING

This application contains a Sequence Listing submitted as an electronic text file named "3923-20-PCT_ST25", having a size in bytes of 101 kb, and created on Sep. 17, 2009. The information contained in this electronic file is hereby incorporated by reference in its entirety pursuant to 37 CFR §1.52 (e)(5).

FIELD OF THE INVENTION

This invention generally relates to methods for treating chronic hepatitis C virus (HCV) infection in a subject.

BACKGROUND OF THE INVENTION

Hepatitis C virus (HCV) is a major causative agent of acute and chronic hepatitis worldwide. HCV infection affects more than 200 million people worldwide and represents a significant health problem in many countries (Lauer and Walker, *N Engl J Med* 2001; 345: 41-52; Shepard et al., *Lancet Infect Dis* 2005; 5:558-567.). Approximately 20-40% of individuals infected with HCV clear the virus during the acute phase, whereas the remaining 60-80% develop chronic disease which may result in hepatic failure and liver cancer (Villano et al., *Hepatology* 1999; 29:908-914; Seeff, *Hepatology* 2002; 36:S35-S46; Cox et al., *Clin Infect Dis* 2005; 40:951-958). There is at present no preventative composition, and therapeutic options are currently limited to interferon/ribavirin therapy (see below), which is often poorly tolerated, is contraindicated in many subjects, and is expensive. In addition, the efficacy of the current standard treatment with interferon and ribavirin is limited, especially in genotype 1, the most prevalent genotype in the U.S. and most industrialized countries (Dienstag and McHutchison, *Gastroenterology* 2006; 130:231-264). Thus, only a proportion of HCV-infected persons can be successfully treated using current standard of care regimens.

HCV is a non-cytopathic virus that induces both acute and chronic hepatitis and interacts in a highly complex manner with the immune system (Rehermann and Nascimbeni, *Nat Rev Immunol* 2005; 5:215-229). Likewise, the immune system has a unique role in the pathogenesis of HCV infection, as it contributes both to control of viral infection and liver repair, but also to the development of chronic infection and liver cirrhosis.

As mentioned above, the current Standard Of Care (SOC) for the treatment of chronic hepatitis C is pegylated interferon-alpha plus ribavirin combination therapy, where the interferon is typically administered by subcutaneous injection once weekly for 24 weeks (HCV genotypes 2 and 3) or 48 weeks (HCV genotypes 1 and 4), with daily doses of ribavirin. While interferon/ribavirin therapy is relatively efficacious in patients suffering from genotype 2 or 3 HCV infection (~85% of patients reach Sustained Virologic Response (SVR)), about 50% of patients infected with genotype 1 HCV do not reach SVR. Moreover, the current SOC is poorly tolerated—interferons are proinflammatory cytokines that are known to cause side effects, including flu-like symptoms and depression, and ribavirin induces hemolytic anemia in 20-30% of patients. When used together as Standard of Care (SOC), adverse events reported include flu-like symptoms (e.g., fever, headache, chills), gastrointestinal issues (e.g., nausea, anorexia, diarrhea), neuropsychiatric disorders (e.g., depression), skin disorders, and hematological disorders. These side effects often lead to patient non-compliance or discontinuation of treatment, and require erythropoietin rescue and/or dose reductions in 10-20% of patients.

The behavior of the serum HCV RNA levels in chronic HCV has been predicted in various settings using a 3 compartment model of viral kinetics, which includes uninfected liver cells, infected liver cells, and free virus in the serum. Viral levels in the peripheral blood early during the course of interferon (IFN) therapy have served as an early predictor of response to therapy due to the fact that they can be measured easily and have been correlated to other more meaningful endpoints in the setting of long-term IFN treatment, such as Sustained Virologic Response (SVR, defined as negative peripheral viral levels for at least 6 months after the completion of IFN-based therapy). Viral clearance in the setting of interferon therapy is bi-phasic; a rapid early phase of peripheral viral load reduction which occurs in the first week(s) (phase 1), followed by the rate limiting, gradual second phase of peripheral viral load reduction which occurs over many months (phase 2) (Layden-Almer et al., *J Viral Hep* 2006; 13:499-504; Herrmann and Zeuzem S. *Eur J Gastroenterol Hepatol* 2006; 18:339-342). While phase 1 kinetics reflect the efficiency of inhibition of viral replication (driven by rapid peripheral viral clearance), phase 2 kinetics represent direct clearance of infected liver cells. Clearance of infected hepatocytes is the rate limiting step in achieving complete eradication of hepatic infection and SVR.

While the ultimate goal of therapy is SVR, there are several early prognostic endpoints that serve as markers to guide patient treatment. These endpoints are summarized in Table 1 below.

TABLE 1

| Endpoint | Definition | Predictive Value |
|---|---|---|
| Rapid Virologic Response (RVR) | Viral negativity at week 4 of IFN therapy | 90-100% of RVRs (prior treatment naïve subjects) will reach SVR[1,2,3] |
| Early Virologic Response (EVR) | >2 log10 reduction in viral load at week 12 of interferon therapy | <3% of non-EVRs will reach SVR[4]; 60-75% of EVRs reach SVR[3,5,6,7] |

TABLE 1-continued

| Endpoint | Definition | Predictive Value |
|---|---|---|
| Complete EVR (cEVR) | Viral negativity at week 12 of IFN therapy | ~90% of cEVRs will reach SVR[5] |
| End of Treatment Response (ETR) | Viral negativity at 48 weeks (genotype 1) | ~80% of ETRs will achieve SVR[8] |
| Sustained Virologic Response (SVR or SVR24) | Viral negativity at 6 months post-ETR | ~98% of subjects achieving SVR24 will remain virus free 5 years out[9] |

[1]Yu et al, RVR and treatment duration in CHC: a randomized trial; Hepatology 2008
[2]Jensen et al, Early ID of HCV G1 patients responding to 24 wks of treatment; Hepatology 2006
[3]Schiffman M L (2007) "New Management Strategies for HCV Nonresponders and Relapsers"
[4]Pegasys prescribing information 2008; Roche
[5]Brandao et al, 24 vs 48 weeks of Pegasys (Riba) in (Geno 1, naives) CHC; J. Viral Hepatitis 2006.
[6]Manns et al, PegIntron (Riba) vs IFN (Riba) in (CHC); Lancet 2001
[7]Poordad et al, RVR in the management of CHC: Clin Inf Dis 2008
[8]Hoofnagel et al, PegInteferon & Riba case study; NEJM 2008
[9]Schering Plough Treatment Outcomes Study Of the endpoints in Table 1, EVR represents the most important negative predictor of outcome. Patients failing to achieve an EVR (>2 log 10 reduction in viral load) by week 12 on interferon therapy have <3% chance of ultimately achieving an SVR. These patients are routinely taken off therapy to spare them from the significant side effects associated with SOC, since it is believed that the native immune response in these patients is incapable of clearing virally infected cells in the context of 48 weeks of viral suppression. RVR and cEVR are positive predictive endpoints, with approximately 90% of patients ultimately achieving SVR after 48 weeks of pegylated-interferon-based therapy.

Patients are categorized by their response at these virologic endpoints. "Null Responders" are patients that cannot achieve at least a 1 log 10 reduction in viral load by week 12 on SOC; it is believed that these patients may have an impaired immune system. "Non-Responders" are patients who receive a 12-week course of therapy and fail to achieve EVR. "Partial Responders" are defined as patients who have >2 log 10 viral load reduction by 12 weeks, but never achieve viral negativity. These patients have a 20-30% chance of responding to a more aggressive regimen. "Relapsers" are patients who achieve viral eradication (negativity) at end of treatment, but whose viral load returns to detectable levels during the 24 week follow up.

The average patient response to 48 weeks of standard of care in genotype 1 patients has been well characterized. For example, of patients with chronic hepatitis C infection (genotype 1) receiving the SOC therapy of pegylated interferon-α2 (PEGASYS® (Peginterferon alfa-2a; Roche Pharmaceuticals)) plus ribavirin, Table 2 shows the typical expected response for these patients.

TABLE 2

| Response | Interferon/Ribavirin Treatment Phenotype of Patient | | |
|---|---|---|---|
| Endpoint | Naïve | Relapser | Non-Responder |
| RVR | 10-15%[1] | | |
| EVR | ~80%[1] | 57%[2] | 33%[2] |
| cEVR | ~43%[3] | | |

TABLE 2-continued

| Response | Interferon/Ribavirin Treatment Phenotype of Patient | | |
|---|---|---|---|
| Endpoint | Naïve | Relapser | Non-Responder |
| ETR | 68-69%[4,5,6] | | |
| SVR24 | 46-52%[4,6,7,8] | | 10-15%[9] |

[1]Schiffman M L (2007) "New Management Strategies for HCV Nonresponders and Relapsers"
[2]Sporea et al, Randomized Study of Pegasys (Riba) vs PegIntron (Riba); J Gastro Liver Disease, June 2006
[3]PROVE 2 study; taken from DM Stakeholder Opinions (Datamonitor Stakeholder Opinions: Hepatitis C "Small molecule antivirals pave the way for triple therapy" December 2007) - 12 wks of triple therapy
[4]Schiffman et al, Pegasys (Riba) v PegIntron (Riba) v Pegasys in CHC; NEJM 2002
[5]Poordad et al, RVR in the management of CHC: Clin Inf Dis 2008
[6]Jensen et al, Early ID of HCV G1 patients responding to 24 wks of treatment; Hepatology 2006
[7]Pegasys prescribing information 2008; Roche
[8]Brandao et al, 24 vs 48 weeks of Pegasys (Riba) in (Geno 1, naives) CHC; J. Viral Hepatitis 2006.
[9]Nevens et al. J Hepatol 2005: 42: A588

Numerous reports suggest that viral replication, the level of viremia, and progression to the chronic state in hepatitis C-infected individuals are influenced directly and indirectly by HCV-specific cellular immunity mediated by $CD4^+$ helper (Th) and $CD8^+$ θcytotoxic T lymphocytes (CTLs) (Cooper et al., *Immunity* 1999; 10:439-449; Gerlac et al., *Gastroenterology* 1999; 117:933-941; Lechner et al., *J Exp Med* 2000; 191:1499-1512; Thimme et al., *J Exp Med* 2001; 194:1395-1406; Shoukry et al., *Annual Rev Microbiol* 2004; 58:391-424). Studies of humans and chimpanzees have revealed that HCV can replicate for weeks before the onset of $CD4^+$ and $CD8^+$ T cell responses can be detected in the liver and in the blood. Moreover, there may be a delay in the acquisition of function by $CD8^+$ (and perhaps $CD4^+$) T cells even after their expansion in blood (Shoukry, ibid.). The appearance of functional $CD8^+$ T cells is kinetically associated with control of viremia and, at least in some cases, with an elevation in serum transaminases, suggesting that liver damage during acute hepatitis C is immunopathological. At highest risk of persistent HCV infection are those individuals who fail to generate a detectable virus-specific T lymphocyte response in the blood, liver, or both. Perhaps most importantly, generation of a cellular immune response does not necessarily ensure that the infection will be permanently controlled. $CD4^+$ and $CD8^+$ T cell responses must be sustained for weeks or months beyond the point of apparent control of virus replication to prevent relapse and establishment of a persistent infection.

While SOC provides the best current treatment for patients chronically infected with HCV, the significant adverse effects of this regimen that can lead to noncompliance, dose reduction, and treatment discontinuation, combined with the percentage of patients who still fail to respond or sustain response to therapy, leaves opportunities for novel therapeutic treatments for HCV.

SUMMARY OF THE INVENTION

One embodiment of the invention relates to a method to treat chronic hepatitis C virus (HCV) infection. The method includes administering to a subject an immunotherapeutic composition comprising at least one HCV antigen or immunogenic domain thereof, and further administering to the subject one or both of at least one interferon and at least one anti-viral compound. In this embodiment, the interferon and anti-viral compound are first administered at least 4 weeks after the immunotherapeutic composition is first administered. In one aspect, the interferon and anti-viral compound are first administered between 4 and 12 weeks after the immunotherapeutic composition is first administered. In another aspect, the interferon and anti-viral compound are first administered at least 12 weeks after the immunotherapeutic composition is first administered.

In any aspect of the above-described embodiment, the interferon can be administered to the subject weekly and the anti-viral compound can be concurrently administered to the subject daily, for a total of between 24 and 48 weeks. Alternatively, the interferon can be administered to the subject every 2, 3 or 4 weeks.

In one aspect of the embodiments described above, additional doses of the immunotherapeutic composition can be administered during the same period as the administration of the interferon and anti-viral compound. In one aspect, the immunotherapeutic composition is administered on the same days as the interferon and/or anti-viral compound. In one aspect, dosing of the immunotherapeutic composition alternates with the administration of the interferon and/or anti-viral compound, and wherein each dose of the immunotherapeutic composition is administered at least 3-4 days after the last dose of interferon and/or anti-viral compound.

In one aspect of the embodiments described above, the immunotherapeutic composition is administered weekly for between 4 and 12 weeks, followed by monthly administration. In one aspect, the immunotherapeutic composition is administered weekly for five weeks, followed by monthly administration.

Another embodiment of the invention relates to a method to treat chronic hepatitis C virus (HCV) infection. The method includes administering to a subject an immunotherapeutic composition comprising at least one HCV antigen or immunogenic domain thereof, and further administering to the subject one or both of an interferon and an anti-viral compound. In this embodiment, the immunotherapeutic composition is administered at least 1 to 4 weeks after the interferon and anti-viral compound are first administered. In one aspect, the immunotherapeutic composition is administered between 4 and 12 weeks after the interferon and anti-viral compound are first administered. In one aspect, the immunotherapeutic composition is administered at least 12 weeks after the interferon and anti-viral compound are first administered. In one aspect, the immunotherapeutic composition administration is initiated over the same time period as the interferon administration is initiated.

Yet another embodiment of the invention relates to a method to treat chronic hepatitis C virus (HCV) infection. The method includes administering to a subject an immunotherapeutic composition comprising at least one HCV antigen or immunogenic domain thereof, and further administering to the subject one or both of an interferon and an anti-viral compound. The immunotherapeutic composition is administered after the final doses of interferon and anti-viral compound are administered.

Another embodiment of the invention relates to a method to treat chronic hepatitis C virus (HCV) infection. The method includes administering to a subject an immunotherapeutic composition comprising at least one HCV antigen or immunogenic domain thereof and an interferon, and further administering to the subject an anti-viral compound. In this embodiment, the anti-viral compound is first administered at least 4 weeks after the immunotherapeutic composition and interferon are first administered.

Yet another embodiment of the invention relates to a method to treat chronic hepatitis C virus (HCV) infection. The method includes administering to a subject an immunotherapeutic composition comprising at least one HCV antigen or immunogenic domain thereof and an anti-viral compound, and further administering to the subject an interferon. In this embodiment, the interferon is first administered at least 4 weeks after the immunotherapeutic composition and anti-viral compound are first administered.

Another embodiment of the invention relates to a method to treat chronic hepatitis C virus (HCV) infection. This method includes administering to a subject an immunotherapeutic composition comprising at least one HCV antigen or immunogenic domain thereof, an interferon, and an anti-viral compound. In this embodiment, the immunotherapeutic composition, the interferon and the anti-viral compound are administered over the same period of time.

Yet another embodiment of the invention relates to a method to increase the frequency of rapid virologic responses (RVR) and/or early virologic responses (EVR/cEVR) in a population of subjects chronically infected with hepatitis C virus (HCV), as compared to RVR and EVR/cEVR in a population of subjects chronically infected with HCV and treated only with combination interferon and anti-viral therapy. The method includes administering to the population of subjects an immunotherapeutic composition that elicits a T cell-mediated immune response against one or more HCV antigens in combination with interferon and an anti-viral compound. In one aspect, the immunotherapeutic composition is first administered at least 4 weeks prior to the first administration of the combination of interferon and anti-viral compound. In another aspect, the immunotherapeutic composition is first administered at least 12 weeks prior to the first administration of the combination of interferon and anti-viral compound.

Yet another embodiment of the invention relates to a method to enhance the conversion of rapid virologic responses (RVR) and/or early virologic responses (EVR/cEVR) to sustained virologic responses (SVR) in a population of subjects chronically infected with hepatitis C virus (HCV), as compared to the conversion of RVR and/or EVR/cEVR to SVR in the same population that is treated only with interferon and anti-viral therapy. The method includes administering to the population of subjects an immunotherapeutic composition that elicits a T cell-mediated immune response against one or more HCV antigens in combination with interferon and an anti-viral compound. In one aspect, the immunotherapeutic composition is first administered at least 4 weeks prior to the first administration of the combination of interferon and anti-viral compound. In another aspect, the immunotherapeutic composition is first administered at least 12 weeks prior to the first administration of the combination of interferon and anti-viral compound.

Another embodiment of the invention relates to a method to increase the number of complete responders in a population of subjects chronically infected with hepatitis C virus (HCV), as compared to the number of complete responders in a population of subjects chronically infected with HCV that is treated only with interferon and anti-viral therapy. The method includes administering to the population of subjects an immunotherapeutic composition that elicits a T cell-mediated immune response against one or more HCV antigens in combination with interferon and an anti-viral compound. In one aspect, the immunotherapeutic composition is first administered at least 4 weeks prior to the first administration of the combination of interferon and anti-viral compound. In one aspect, the immunotherapeutic composition is first administered at least 12 weeks prior to the first administration of the combination of interferon and anti-viral compound.

Yet another embodiment of the invention relates to a method to reduce the number of breakthrough subjects during treatment or the number of relapsers post-treatment in a population of subjects chronically infected with hepatitis C virus (HCV), as compared to the number of breakthroughs during treatment or the number of relapses post-treatment in a population of subjects chronically infected with HCV that is treated only with interferon and anti-viral therapy. The method includes administering to the population of subjects an immunotherapeutic composition that elicits a T cell-mediated immune response against one or more HCV antigens in combination with interferon and an anti-viral compound. In one aspect, the immunotherapeutic composition is first administered at least 4 weeks prior to the first administration of the combination of interferon and anti-viral compound. In one aspect, the immunotherapeutic composition is first administered at least 12 weeks prior to the first administration of the combination of interferon and anti-viral compound.

Another embodiment of the invention relates to a method to inhibit the emergence of drug-resistant HCV mutations. The method includes administering to the population of subjects an immunotherapeutic composition that elicits a T cell-mediated immune response against one or more HCV antigens in combination with interferon and an anti-viral compound. In one aspect, the immunotherapeutic composition is first administered at least 4 weeks prior to the first administration of the combination of interferon and anti-viral compound. In one aspect, the immunotherapeutic composition is first administered at least 12 weeks prior to the first administration of the combination of interferon and anti-viral compound.

Yet another embodiment of the invention relates to a method to treat a subject who is chronically infected with HCV. The method includes: (a) administering an immunotherapeutic composition that elicits a T cell-mediated immune response against one or more HCV antigens to the subject for at least 4 to 12 weeks, followed by administering interferon and anti-viral concurrently with continued administration of the immunotherapeutic composition; (b) determining the rapid virologic response (RVR) of the subject at about 4 weeks after the first administration of interferon and anti-viral compound; and (c) reducing the dosage and/or frequency of interferon-anti-viral compound therapy in subjects with an RVR that is statistically significantly greater or strongly trending toward greater than the expected RVR of a subject treated with combination interferon-anti-viral compound therapy alone.

Another embodiment of the invention relates to a method to continue treatment of a chronically HCV-infected subject who is predicted to fail combination interferon-anti-viral compound therapy. The method includes administering to the subject an immunotherapeutic composition that elicits a T cell-mediated immune response against one or more HCV antigens. In one aspect, the subject continues receiving combination interferon-anti-viral compound therapy during the period of time in which the immunotherapeutic composition is administered.

Yet another embodiment of the invention relates to a method to reduce liver damage and/or improve liver function in a chronically HCV-infected subject. The method includes administering to the subject an immunotherapeutic composition comprising at least one HCV antigen or immunogenic domain thereof, and optionally, an interferon and an anti-viral compound.

Another embodiment of the invention relates to a method to continue treatment of a chronically HCV-infected subject who is intolerant to combination interferon-anti-viral compound therapy. The method includes ceasing the combination therapy and administering to the subject an immunotherapeutic composition that elicits a T cell-mediated immune response against one or more HCV antigens.

In any of the above-described embodiments, the immunotherapeutic composition elicits a T cell-mediated immune response against one or more HCV antigens. In a preferred embodiment, the immunotherapeutic composition is a yeast-based immunotherapeutic composition.

In one aspect of any of the embodiments of the invention described herein, the subject is naïve to any prior treatment for HCV. In one aspect, the subject is naïve to any prior interferon-based treatment for HCV. In one aspect, the subject is naïve to any prior interferon-based treatment for HCV and has a high viral titer at baseline (>600,000 IU/ml HCV RNA levels). In one aspect, the subject is a prior non-responder or partial responder to a treatment for HCV.

In one aspect of any of the embodiments of the invention described herein, the method improves at least one parameter of liver function in the subject. In one aspect, the method decreases liver damage in the subject.

One embodiment of the invention relates to the use of an immunotherapeutic composition comprising at least one HCV antigen or immunogenic domain thereof in the preparation of a medicament for use with one or both of an interferon and an anti-viral compound to reduce liver damage or improve liver function in a chronically HCV-infected subject. The immunotherapeutic composition elicits a T cell-mediated immune response against one or more HCV antigens. In one aspect of this embodiment, the immunotherapeutic composition is a yeast-based immunotherapeutic composition. In one aspect, the HCV-infected subject is a prior non-responder or partial responder to a treatment for HCV. In one aspect, the HCV-infected subject is naïve to any prior interferon-based treatment for HCV. In another aspect, the HCV-infected subject is naïve to any prior interferon-based treatment for HCV and has a high viral titer at baseline (>600,000 IU/ml HCV RNA levels).

Yet another embodiment of the invention relates to the use of an immunotherapeutic composition comprising at least one HCV antigen or immunogenic domain thereof in the preparation of a medicament for use with one or both of an interferon and an anti-viral compound for the treatment of chronic hepatitis C virus (HCV) in a subject. In one aspect of this embodiment, the subject is naïve to any prior treatment for HCV. In one aspect of this embodiment, the subject is naïve to any prior interferon-based treatment for HCV. In another aspect, the subject is naïve to any prior interferon-based treatment for HCV and has a high viral titer at baseline (>600,000 IU/ml HCV RNA levels). The immunotherapeutic composition elicits a T cell-mediated immune response against one or more HCV antigens. In one aspect of this embodiment, the immunotherapeutic composition is a yeast-based immunotherapeutic composition.

Another embodiment of the invention relates to the use of an immunotherapeutic composition comprising at least one HCV antigen or immunogenic domain thereof in the preparation of a medicament for use with one or both of an interferon and an anti-viral compound to increase the frequency of rapid virologic responses (RVR) and/or early virologic responses (EVR/cEVR) in a population of subjects chronically infected with hepatitis C virus (HCV), as compared to RVR and EVR/cEVR in a population of subjects chronically infected with HCV and treated only with combination interferon and anti-viral therapy. The immunotherapeutic composition elicits a T cell-mediated immune response against one or more HCV antigens. In one aspect of this embodiment, the immunotherapeutic composition is a yeast-based immunotherapeutic composition.

Yet another embodiment of the invention relates to the use of an immunotherapeutic composition comprising at least one HCV antigen or immunogenic domain thereof in the preparation of a medicament for use with one or both of an interferon and an anti-viral compound to enhance the conversion of rapid virologic responses (RVR) and/or early virologic responses (EVR/cEVR) to sustained virologic responses (SVR) in a population of subjects chronically infected with hepatitis C virus (HCV), as compared to the conversion of RVR and/or EVR/cEVR to SVR in the same population that is treated only with interferon and anti-viral therapy. The immunotherapeutic composition elicits a T cell-mediated immune response against one or more HCV antigens. In one aspect of this embodiment, the immunotherapeutic composition is a yeast-based immunotherapeutic composition.

Another embodiment of the invention relates to the use of an immunotherapeutic composition comprising at least one HCV antigen or immunogenic domain thereof in the preparation of a medicament for use with one or both of an interferon and an anti-viral compound to increase the number of complete responders in a population of subjects chronically infected with hepatitis C virus (HCV), as compared to the number of complete responders in a population of subjects chronically infected with HCV that is treated only with interferon and anti-viral therapy. The immunotherapeutic composition elicits a T cell-mediated immune response against one or more HCV antigens. In one aspect of this embodiment, the immunotherapeutic composition is a yeast-based immunotherapeutic composition.

Another embodiment of the invention relates to the use of an immunotherapeutic composition comprising at least one HCV antigen or immunogenic domain thereof in the preparation of a medicament for use with one or both of an interferon and an anti-viral compound to reduce the number of breakthrough subjects during treatment or the number of relapsers post-treatment in a population of subjects chronically infected with hepatitis C virus (HCV), as compared to the number of breakthroughs during treatment or the number of relapses post-treatment in a population of subjects chronically infected with HCV that is treated only with interferon and anti-viral therapy. The immunotherapeutic composition elicits a T cell-mediated immune response against one or more HCV antigens. In one aspect of this embodiment, the immunotherapeutic composition is a yeast-based immunotherapeutic composition.

Yet another embodiment of the invention relates to the use of an immunotherapeutic composition comprising at least one HCV antigen or immunogenic domain thereof in the preparation of a medicament for use with one or both of an interferon and an anti-viral compound to inhibit the emergence of drug-resistant HCV mutations. The immunotherapeutic composition elicits a T cell-mediated immune response against one or more HCV antigens. In one aspect of this embodiment, the immunotherapeutic composition is a yeast-based immunotherapeutic composition.

Another embodiment of the invention relates to the use of an immunotherapeutic composition comprising at least one HCV antigen or immunogenic domain thereof in the preparation of a medicament for use with one or both of an interferon and an anti-viral compound to continue treatment of a chronically HCV-infected subject who is predicted to fail combination interferon-anti-viral compound therapy. The immunotherapeutic composition elicits a T cell-mediated immune response against one or more HCV antigens. In one aspect of this embodiment, the immunotherapeutic composition is a yeast-based immunotherapeutic composition.

Yet another embodiment of the invention relates to the use of an immunotherapeutic composition comprising at least one HCV antigen or immunogenic domain thereof in the preparation of a medicament to continue treatment of a chronically HCV-infected subject who is intolerant to combination interferon-anti-viral compound therapy. The immunotherapeutic composition elicits a T cell-mediated immune response against one or more HCV antigens. In one aspect of this embodiment, the immunotherapeutic composition is a yeast-based immunotherapeutic composition.

Another embodiment of the invention relates to a pharmaceutical composition comprising a yeast-based immunotherapeutic composition comprising (a) at least one HCV antigen or immunogenic domain thereof, (b) an interferon and (c) an anti-viral compound. The yeast-based immunotherapeutic composition comprises a yeast vehicle, wherein the HCV antigen or immunogenic domain thereof is expressed by, attached to, or mixed with the yeast vehicle, and wherein the immunotherapeutic composition elicits a T cell-mediated immune response against one or more HCV antigens.

Yet another embodiment of the invention relates to a kit for treating chronic hepatitis C virus (HCV) infection. The kit includes: (a) a yeast-based immunotherapeutic composition comprising at least one HCV antigen or immunogenic domain thereof, wherein the yeast-based immunotherapeutic composition comprises a yeast vehicle, wherein the HCV antigen or immunogenic domain thereof is expressed by, attached to, or mixed with the yeast vehicle, and wherein the immunotherapeutic composition elicits a T cell-mediated immune response against one or more HCV antigens; (b) at least one interferon; (c) at least one anti-viral compound; and (d) directions for administering each of (a), (b), and (c).

In one aspect, the directions specify first administering the interferon and anti-viral compound at least 4 weeks after the immunotherapeutic composition is first administered. In one aspect, the directions specify first administering the interferon and anti-viral compound between 4 and 12 weeks after the immunotherapeutic composition is first administered. In one aspect, the directions specify first administering the interferon and anti-viral compound at least 12 weeks after the immunotherapeutic composition is first administered.

In another aspect, the directions specify first administering the immunotherapeutic composition at least 1 to 4 weeks after the interferon and anti-viral compound are first administered. In one aspect, the directions specify first administering the immunotherapeutic composition at least 4 to 12 weeks after the interferon and anti-viral compound are first administered. In one aspect, the directions specify first administering the immunotherapeutic composition at least 12 weeks after the interferon and anti-viral compound are first administered.

In one aspect, the directions specify first administering the immunotherapeutic composition after the final doses of interferon and anti-viral compound are administered.

In another aspect, the directions specify first administering the anti-viral compound at least 4 weeks after the immunotherapeutic composition and interferon are first administered.

In another aspect, the directions specify first administering the interferon at least 4 weeks after the immunotherapeutic composition and anti-viral compound are first administered.

In one aspect, the directions specify administering the immunotherapeutic composition, the interferon and the anti-viral compound over the same period of time.

In one aspect, the directions specify administering interferon weekly with concurrent administration of the anti-viral compound daily, for a total of between 24 and 48 weeks.

In one aspect, the directions specify administering interferon every 2, 3 or 4 weeks.

In one aspect, the directions specify administering additional doses of the immunotherapeutic composition during the same period as the administration of the interferon and anti-viral compound.

In one aspect, the directions specify administering the immunotherapeutic composition on the same days as the interferon or anti-viral compound.

In another aspect, the directions specify administering the immunotherapeutic composition alternating with administration of the interferon or anti-viral compound, and that each dose of the immunotherapeutic composition is administered at least 3-4 days after the last dose of interferon and/or anti-viral compound.

In one aspect, the directions specify administering the immunotherapeutic composition weekly for between 4 and 12 weeks, followed by monthly administration.

In yet another aspect, the directions specify administering the immunotherapeutic composition weekly for five weeks, followed by monthly administration.

In one aspect of any of the embodiments of the invention described herein, including any described above, the anti-viral compound is ribavirin or a functional analog thereof, an NS3 protease inhibitor, an NS5b polymerase inhibitor, or a host enzyme inhibitor.

In one aspect of any of the embodiments of the invention described herein, including any described above, the immunotherapeutic composition elicits a CD8+ T cell response. In one aspect, the immunotherapeutic composition elicits a CD4+ T cell response. In one aspect, the immunotherapeutic composition elicits production of interferon-γ by cells. In one aspect, the immunotherapeutic composition has one or more of the following characteristics: (a) stimulates one or more pattern recognition receptors effective to activate an antigen presenting cell; (b) upregulates adhesion molecules, co-stimulatory molecules, and MHC class I and/or class II molecules on antigen presenting cells; (c) induces production of proinflammatory cytokines by antigen presenting cells; (d) induces production of Th1-type cytokines by T cells; and (e) elicits MHC Class I and/or MHC Class II, antigen-specific immune responses. Proinflammatory cytokines include, but are not limited to: interleukin-6 (IL-6), IL-12, IL-1 and tumor necrosis factor-α (TNF-α). Th1-type cytokines include, but are not limited to: IL-2, IL-5, granulocyte macrophage-colony stimulating factor (GM-CSF) and interferon-γ (IFN-γ).

In one aspect of any of the embodiments of the invention described herein, including any described above, the immunotherapeutic composition comprises an adjuvant. In another aspect, the immunotherapeutic composition further comprises at least one biological response modifier.

In one aspect of any of the embodiments of the invention described herein, including any described above, the interferon is pegylated interferon-α.

In one aspect of any of the embodiments of the invention described herein, including any described above, the anti-viral compound may include, but is not limited to: ribavirin or a functional analog thereof, an NS3 protease inhibitor, an NS5b polymerase inhibitor, or a host enzyme inhibitor.

In one aspect of any of the embodiments of the invention described herein, including any described above, the immunotherapeutic composition comprises a yeast vehicle. In any of the embodiments of the invention described herein, in one aspect, a yeast-based immunotherapeutic composition includes a yeast vehicle, wherein the HCV antigen or immunogenic domain thereof is expressed by, attached to, or mixed with the yeast vehicle. In a preferred embodiment, the HCV antigen or immunogenic domain thereof is expressed by the yeast vehicle. The yeast vehicle can, in one aspect, be selected from: a whole yeast, a yeast spheroplast, a yeast cytoplast, a yeast ghost, or a subcellular yeast membrane extract or fraction thereof. In one preferred aspect, the yeast vehicle is a whole yeast or a yeast spheroplast, with whole yeast being particularly preferred. In one aspect, the yeast vehicle is a heat-inactivated yeast. In one aspect, the yeast vehicle is from *Saccharomyces*, with *Saccharomyces cerevisiae* being particularly preferred.

In one aspect of any of the embodiments of the invention described herein, including any described above, the immunotherapeutic composition can include an HCV fusion protein comprising HCV sequences. In this aspect of the invention, the HCV sequences consist of between one and five HCV proteins and/or immunogenic domains thereof. The HCV proteins can include, but are not limited to: HCV Core (positions 1 to 191 of SEQ ID NO:20); HCV E1 envelope glycoprotein (positions 192 to 383 of SEQ ID NO:20); HCV E2 envelope glycoprotein (positions 384 to 746 of SEQ ID NO:20); HCV P7 ion channel (positions 747 to 809 of SEQ ID NO:20); HCV NS2 metalloprotease (positions 810 to 1026 of SEQ ID NO:20); HCV NS3 protease/helicase (positions 1027 to 1657 of SEQ ID NO:20); HCV NS4a NS3 protease cofactor (positions 1658 to 1711 of SEQ ID NO:20); HCV NS4b (positions 1712 to 1972 of SEQ ID NO:20); HCV NS5a (positions 1973 to 2420 of SEQ ID NO:20); or HCV NS5b RNA-dependent RNA polymerase (positions 2421 to 3011 of SEQ ID NO:20). The immunotherapeutic composition elicits an immune response against each of the HCV proteins or immunogenic domains thereof in the HCV fusion protein.

The HCV sequences can consist of an HCV NS3 protease sequence or at least one immunogenic domain thereof linked to an HCV Core sequence or at least one immunogenic domain thereof, wherein the HCV NS3 protease sequence lacks the catalytic domain of a natural HCV NS3 protease, wherein the composition elicits an HCV NS3-specific immune response and an HCV Core-specific immune response. In one aspect, the HCV NS3 protease consists of the 262 amino acids of HCV NS3 following the initial N-terminal 88 amino acids of the full-length NS3 protein (positions 1115 to 1376 with respect to SEQ ID NO:20). In one aspect, the HCV Core sequence consists of amino acid positions 2 through 140 of the full-length HCV Core sequence (positions 2 to 140, with respect to SEQ ID NO:20). In one aspect, the hydrophobic C-terminal sequence of the HCV Core is truncated. One preferred fusion protein consists of SEQ ID NO:2.

The HCV sequences can consist of a full-length, inactivated HCV NS3 protein, or at least one immunogenic domain thereof, wherein the composition elicits an HCV NS3-specific immune response. In one aspect, the HCV NS3 protein comprises a mutation at residue 1165 of the HCV polyprotein sequence, with respect to SEQ ID NO:20, that results in inactivation of the proteolytic activity of the protein. One preferred fusion protein consists of SEQ ID NO:4.

The HCV sequences can consist of an HCV E1 protein or at least one immunogenic domain thereof fused to an HCV E2 protein or at least one immunogenic domain thereof, wherein the composition elicits an HCV E1-specific immune response and an HCV E2-specific immune response. In one aspect, the HCV E1 protein is a full-length protein and wherein the HCV E2 protein is a full-length protein. In one aspect, the fusion protein consists of SEQ ID NO:12. In one aspect, the HCV E1 protein is a truncated E1 protein consisting of amino acids 1 to 156 of HCV E1 (positions 192 to 347, with respect to SEQ ID NO:20). In one aspect, the HCV E2 protein is a truncated E2 protein consisting of amino acids 1 to 334 of HCV E2

(positions 384 to 717, with respect to SEQ ID NO:20). In one aspect, the fusion protein consists of SEQ ID NO:6.

The HCV sequences can consist of a transmembrane domain-deleted HCV NS4b protein or at least one immunogenic domain thereof, wherein the composition elicits an HCV NS4b-specific immune response. In one aspect, the transmembrane domain-deleted HCV NS4b protein consists of amino acids 1 to 69 of HCV NS4b (positions 1712 to 1780, with respect to SEQ ID NO:20) linked to amino acids 177 to 261 of HCV NS4b (positions 1888 to 1972, with respect to SEQ ID NO:20). In one aspect, the fusion protein consists of SEQ ID NO:8.

The HCV sequences can consist of a truncated HCV Core protein or at least one immunogenic domain thereof fused to an HCV E1 protein with deleted transmembrane domain or at least one immunogenic domain thereof fused to an HCV E2 protein with deleted transmembrane domain or at least one immunogenic domain thereof, wherein the composition elicits an HCV Core-specific immune response, an HCV E1-specific immune response, and an HCV E2-specific immune response. In one aspect, the truncated HCV Core protein consists of positions 2 to 140 of HCV Core protein (positions 2 to 140, with respect to SEQ ID NO:20), wherein the HCV E1 protein with deleted transmembrane domain consists of positions 1 to 156 of HCV E1 protein (positions 192 to 347, with respect to SEQ ID NO:20), and wherein the HCV E2 protein with deleted transmembrane domain consists of positions 1 to 334 of HCV E2 protein (positions 384 to 717, with respect to SEQ ID NO:20). In one aspect, the fusion protein consists of SEQ ID NO:14.

The HCV sequences can consist of inactivated HCV NS3 or at least one immunogenic domain thereof fused to HCV NS4a or at least one immunogenic domain thereof fused to HCV NS4b lacking a transmembrane domain or at least one immunogenic domain thereof, wherein the composition elicits an HCV NS3-specific immune response, an HCV NS4a-specific immune response, and an HCV NS4b-specific immune response. In one aspect, the HCV NS3 protein consists of positions 1 to 631 of HCV HS3 (positions 1027 to 1657, with respect to SEQ ID NO:20), wherein the serine at position 1165 with respect to SEQ ID NO:20 has been substituted with alanine, to inactivate the protease; wherein the HCV NS4a protein consists of positions 1 to 54 of the HCV NS4a protein (positions 635 to 691, with respect to SEQ ID NO:20); and wherein the HCV NS4b protein consists of positions 1 to 69 of HCV NS4b (positions 1712 to 1780, with respect to SEQ ID NO:20) fused to positions 177 to 261 of HCV NS4b (positions 1888 to 1972, with respect to SEQ ID NO:20). In one aspect, the fusion protein consists of SEQ ID NO:16.

The HCV sequences can consist of an HCV NS5a protein or at least one immunogenic domain thereof fused to an HCV NS5b protein containing an inactivating deletion of NS5b C-terminus or at least one immunogenic domain thereof, wherein the composition elicits an HCV NS5a-specific immune response. In one aspect, the HCV NS5a protein consists of 1 to 448 of HCV NS5a (positions 1973 to 2420, with respect to SEQ ID NO:20); and wherein the HCV NS5b protein consists of positions 1 to 539 of HCV NS5b (positions 2421 to 2959, with respect to SEQ ID NO:20). In one aspect, the fusion protein consists of SEQ ID NO:18.

BRIEF DESCRIPTION OF THE DRAWINGS OF THE INVENTION

FIG. 1 is a schematic drawing showing the design of a phase II trial combining immunotherapy with Standard of Care therapy for chronic HCV infection.

FIG. 2 is a bar graph showing the Rapid Virologic Response (RVR) rates of patients chronically infected with HCV who have received Standard of Care (SOC) alone versus SOC plus immunotherapy with GI-5005 (5005+SOC). Rates are shown for all patients (Overall (ITT)), those who were previously naïve to treatment with interferon (IFN Naïve), and those who began treatment with a viral load >600,000 IU/ml at baseline (High Viral Load).

FIG. 3 is a graph showing that prior Non-Responders to Standard of Care (SOC) who were treated with immunotherapy plus SOC (GI-5005+SOC) show a trend to enhanced second phase viral kinetics as compared to prior Non-Responders treated with SOC alone.

FIG. 4 is a bar graph showing Rapid Virologic Response (RVR) for all subjects in the clinical trial who completed the first 4 weeks of triple therapy (SOC plus immunotherapy with GI-5005) versus those who completed 4 weeks of SOC alone. Rates are shown for all patients on study (Overall), all patients who were previously naïve to treatment with interferon (IFN Naïve), and IFN-naïve patients who began treatment with a viral load >600,000 IU/ml at baseline (High Viral Load (Naïve)).

Figure 9:
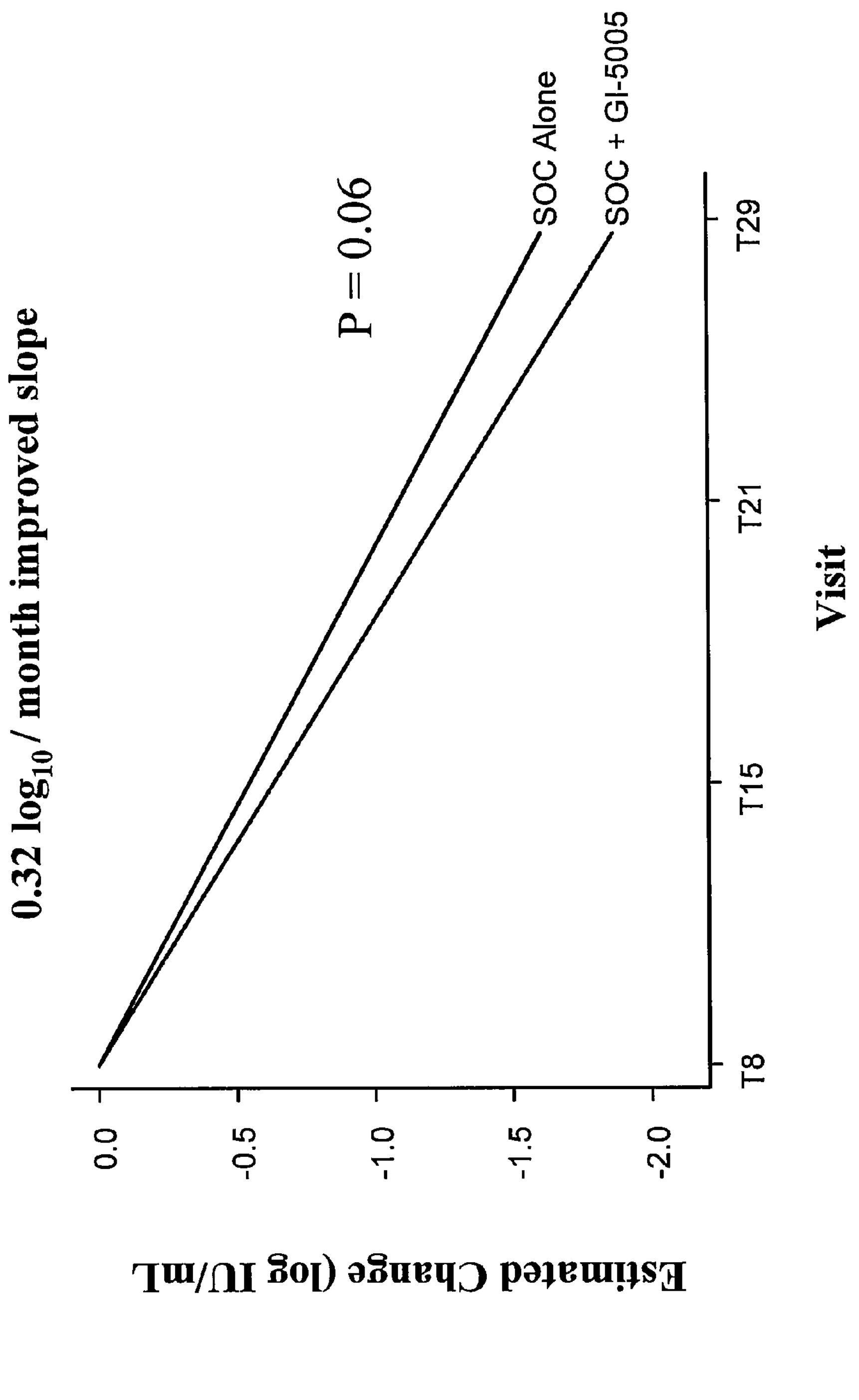

FIG. 9 is a graph showing that, as a group, subjects who were interferon-naïve and had a high viral load at baseline of the study (Interferon Naïve & High Viral Load at Baseline), who completed the first 4 weeks of triple therapy showed a strong trend toward increased (enhanced) second phase kinetics for peripheral viral reduction as compared to subjects treated with SOC alone who were interferon-naïve and had a high viral load at baseline of the study.

Figure 10A:
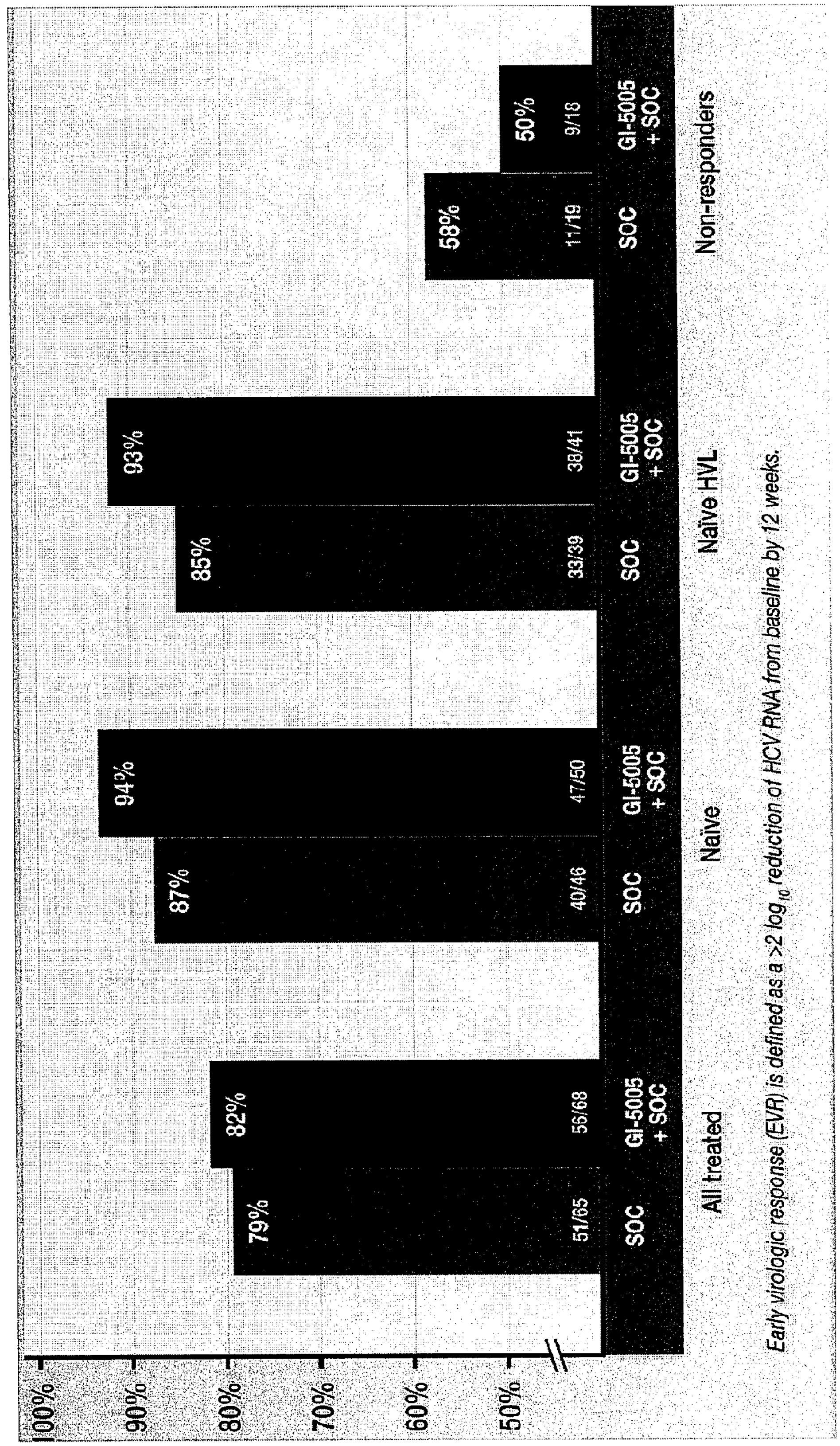

FIG. 10A is a graph showing that, as a group, subjects completing 12 weeks of triple therapy who were interferon-naïve (Naïve), and the subgroup of subjects completing 12 weeks of triple therapy who were interferon-naïve and had a high viral load at baseline of the study (Naïve HVL), showed a strong trend toward improved EVR rates as compared to the comparable groups of patients receiving SOC alone.

Figure 10B:
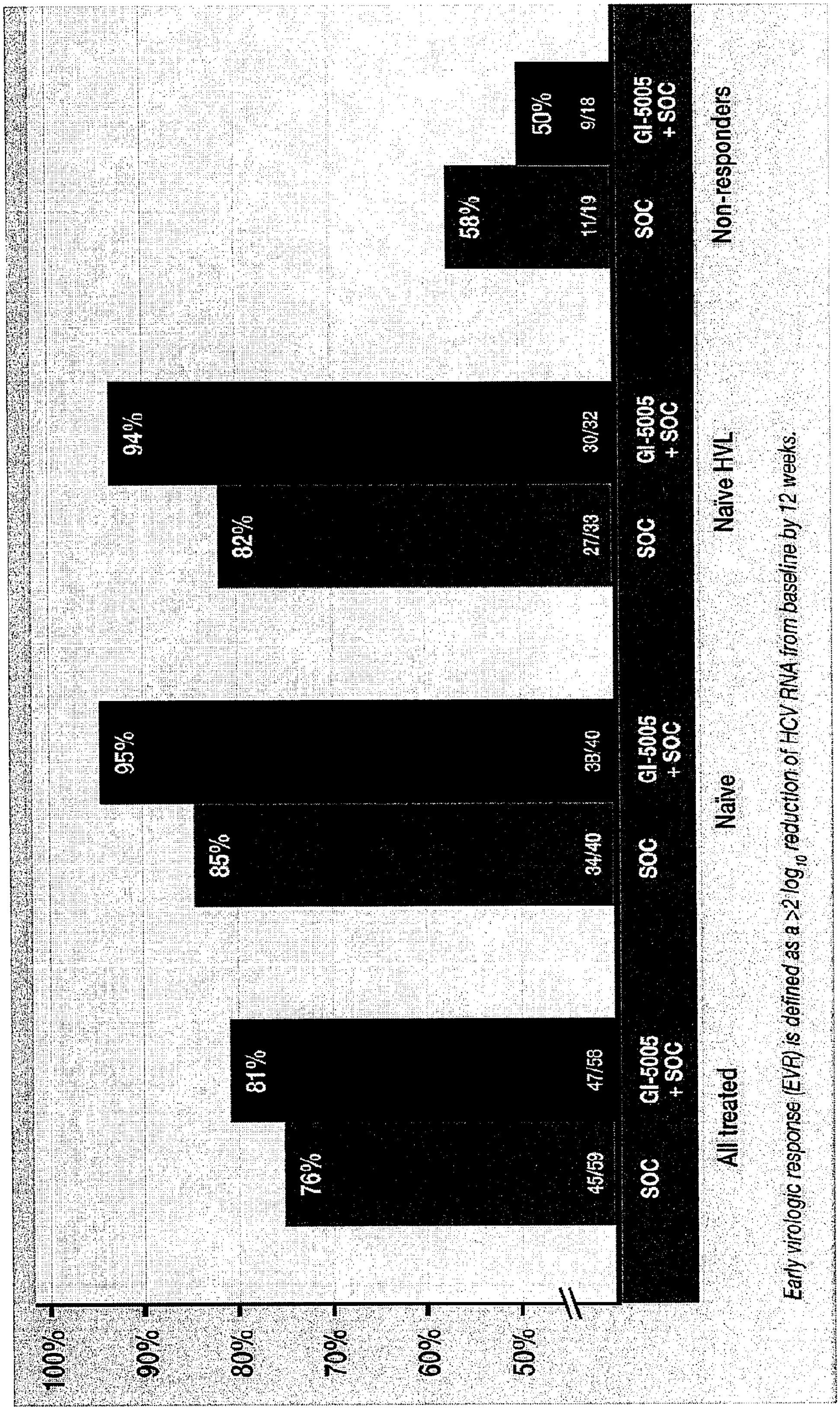

FIG. 10B is a graph showing the same results as in FIG. 10A, but limited to only those patients from clinical trial sites in the United States.

Figure 11A:
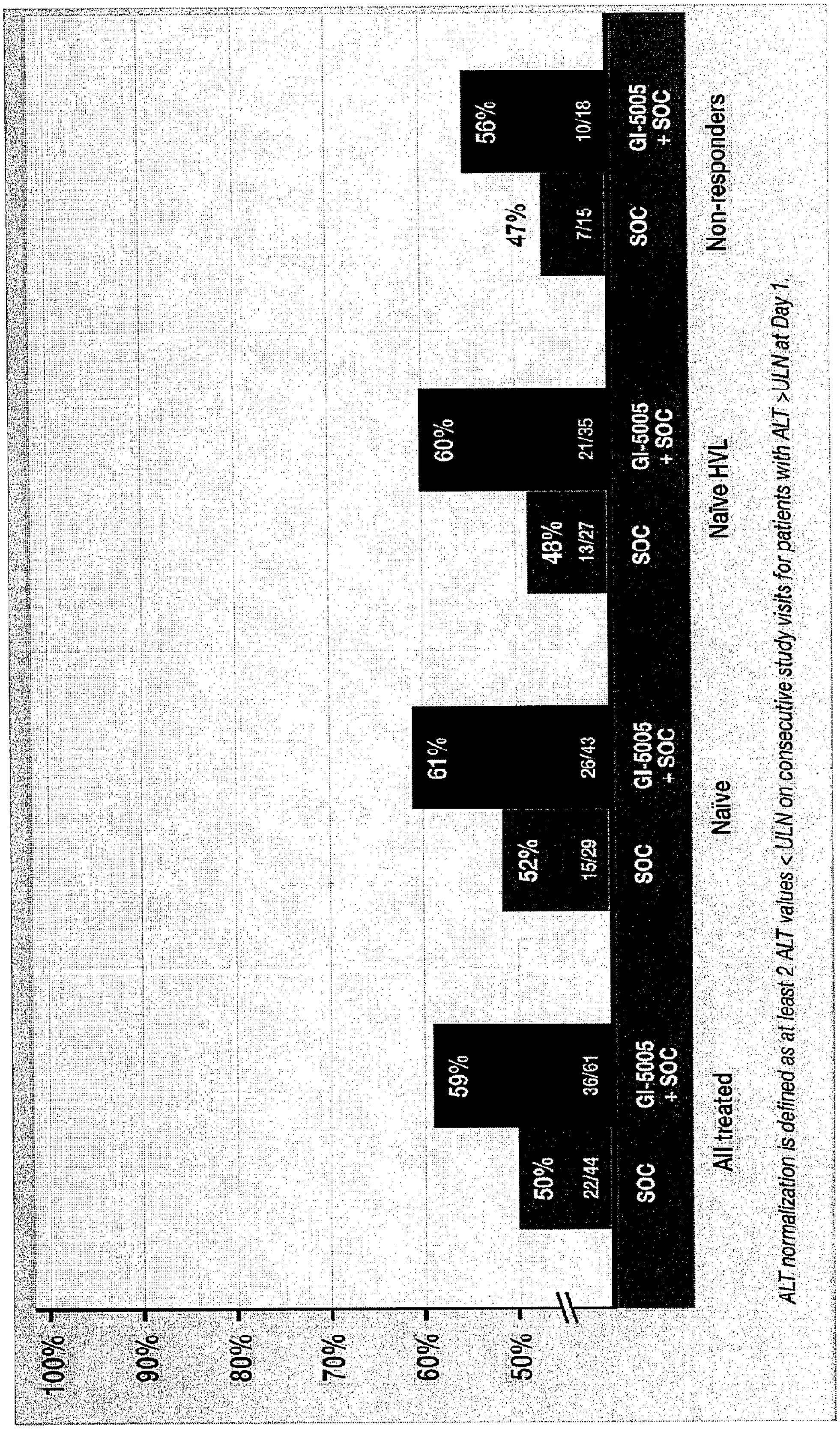

FIG. 11A is a graph showing that triple therapy demonstrated an improvement in ALT normalization at 12 weeks in treatment naïve groups (Naïve and Naïve HVL) as compared to SOC.

Figure 11B:
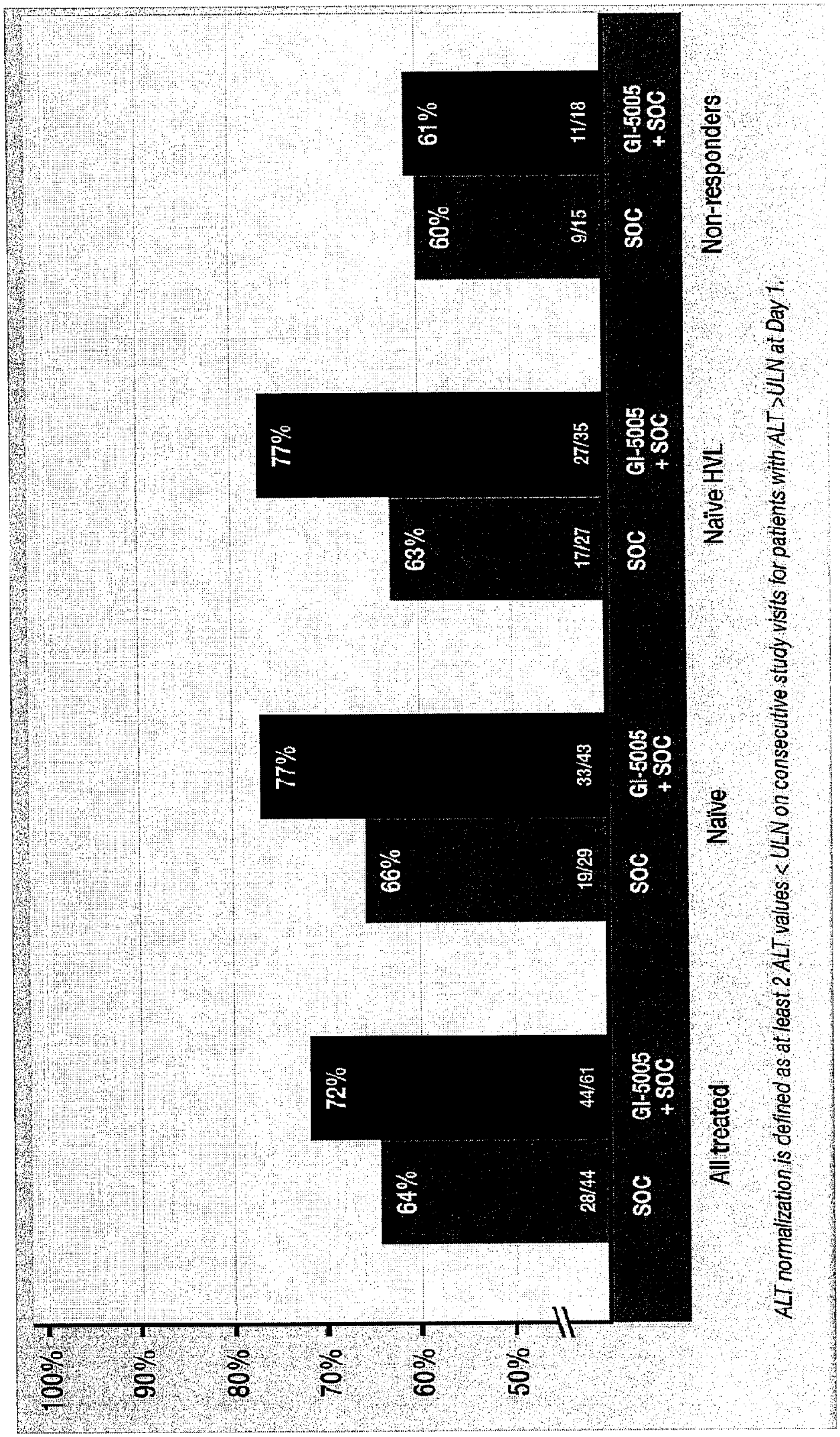

FIG. 11B is a graph showing that triple therapy demonstrated an improvement in ALT normalization at 24 weeks in all treatment naïve groups (Naïve and Naïve HVL) as compared to SOC.

Figure 12A:
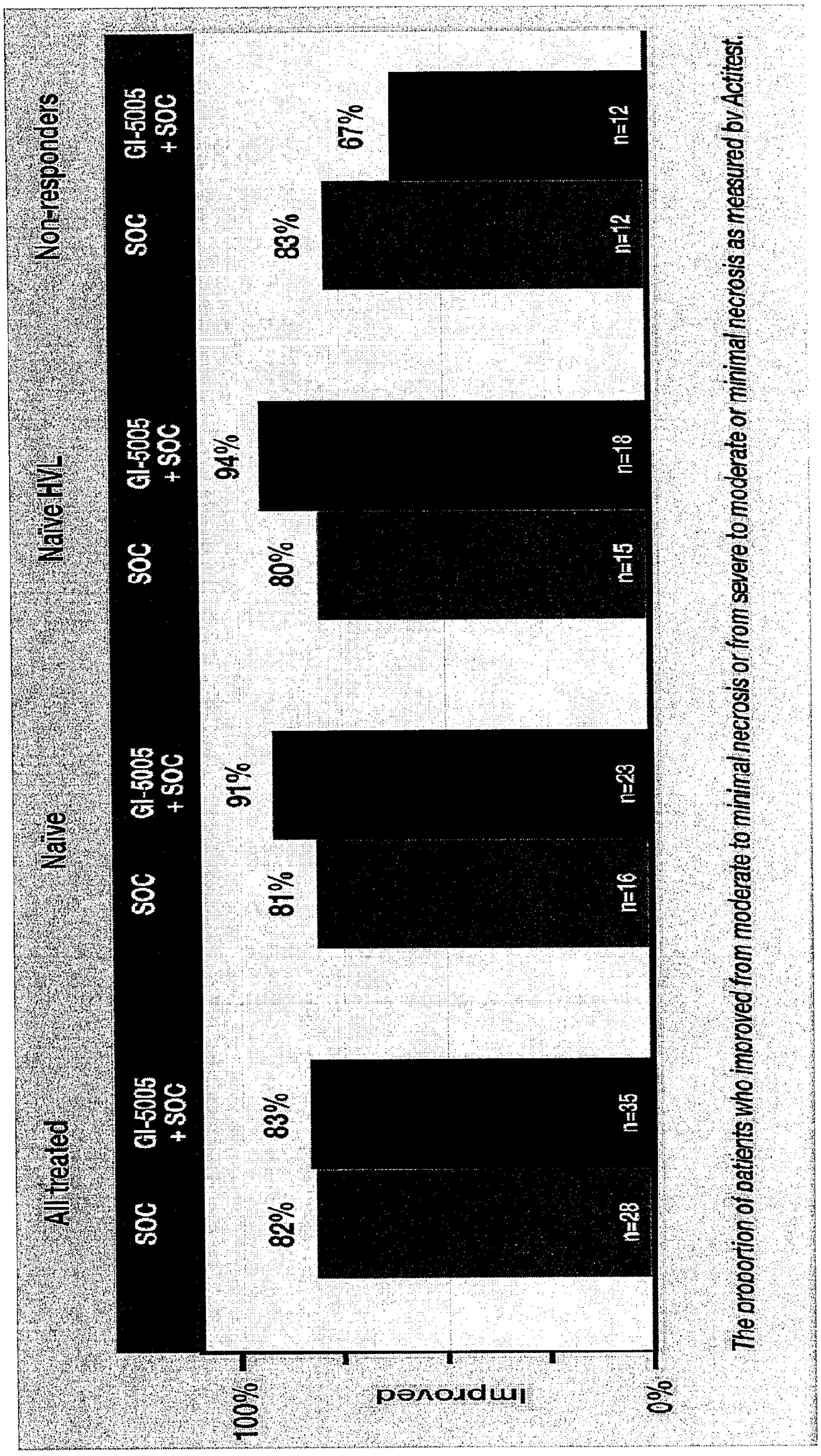

FIG. 12A is a graph showing that triple therapy demonstrated an improvement in Actitest scores at 24 weeks in all treatment naïve groups (Naïve and Naïve HVL) as compared to SOC.

Figure 12B:
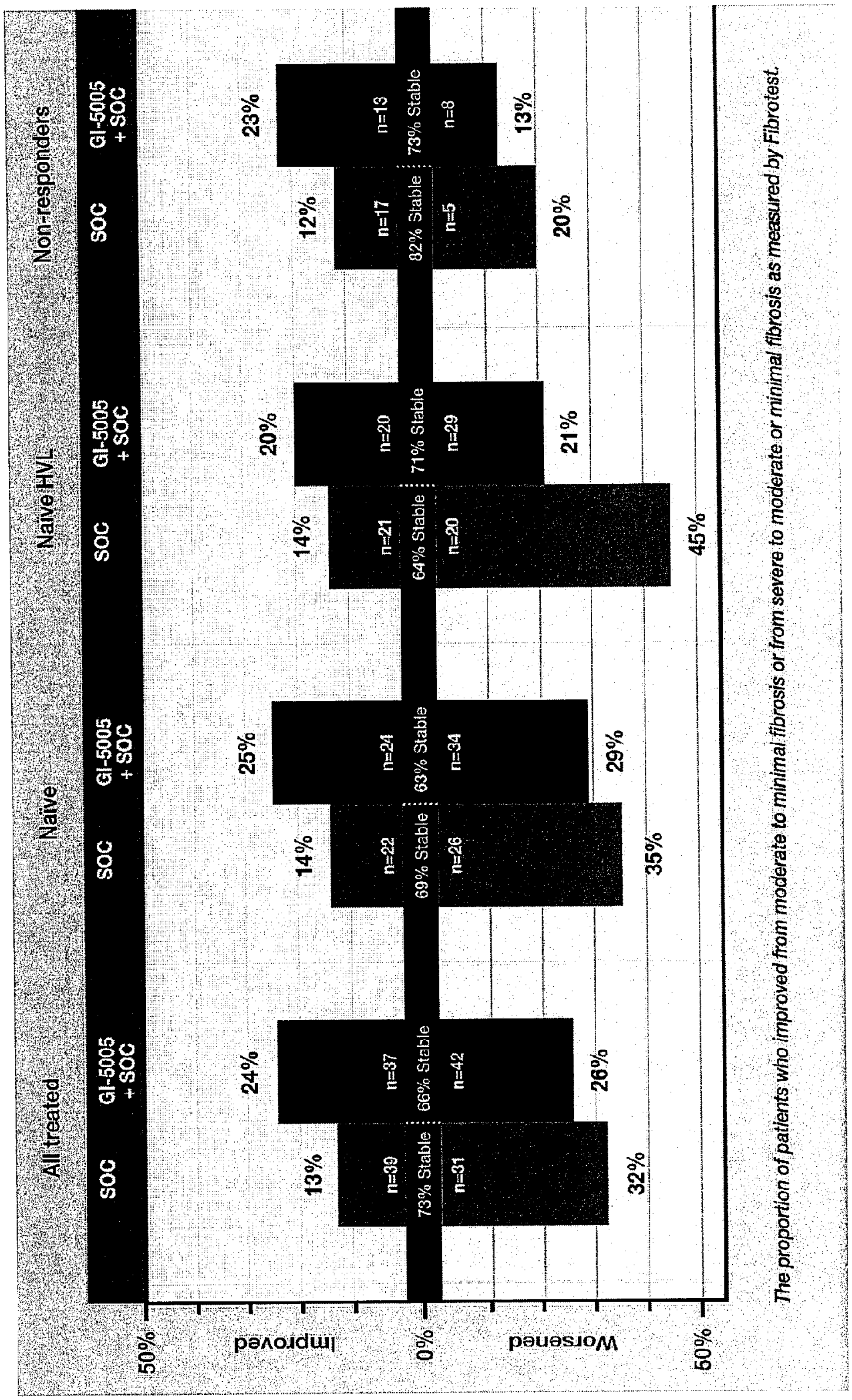

FIG. 12B is a graph showing that triple therapy demonstrated an improvement in Fibrotest scores at 24 weeks in all treatment naïve groups (Naïve and Naïve HVL) as compared to SOC.

Figure 13:
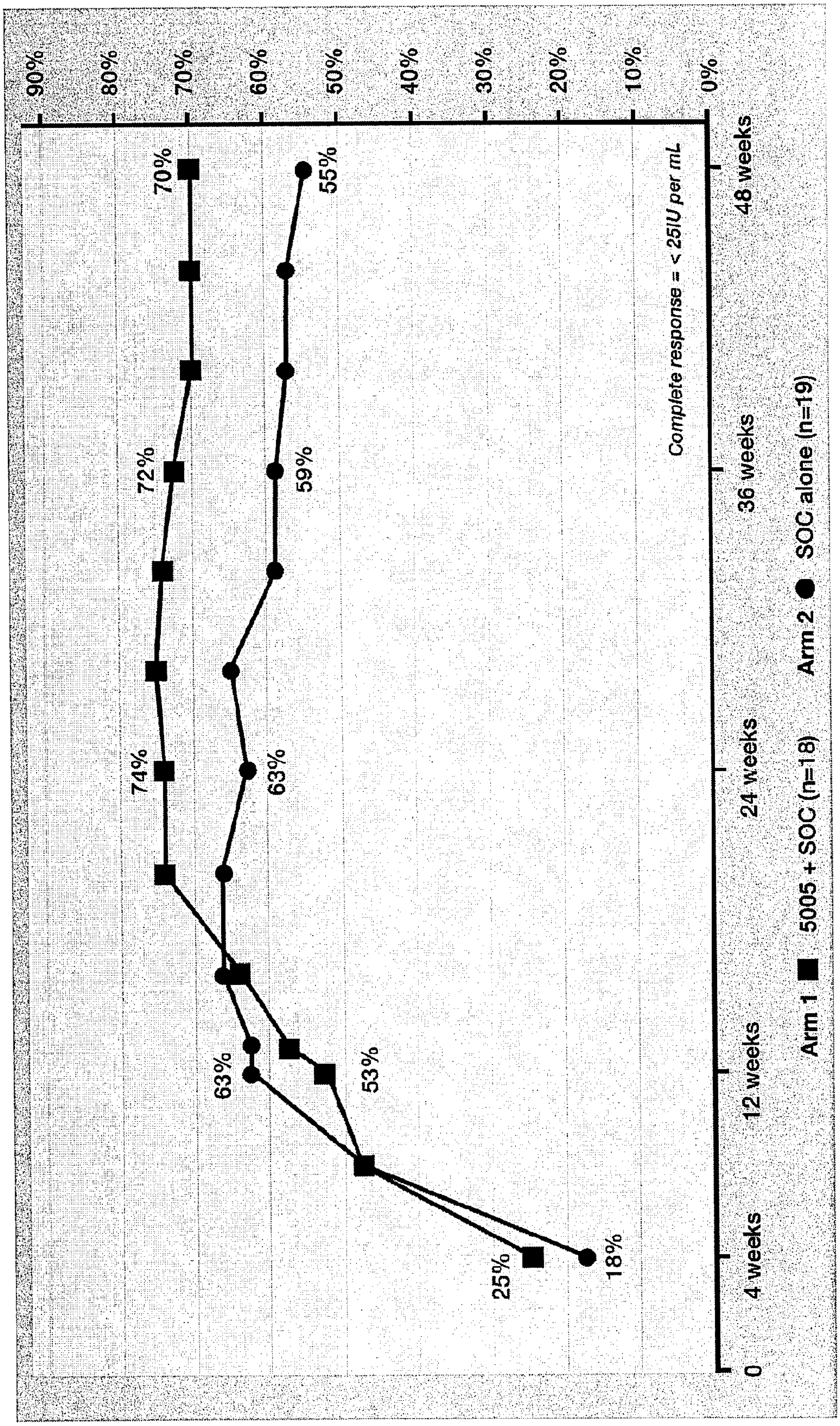

FIG. 13 is a graph showing that, at 48 weeks after start of triple therapy (ETR), improvement in end of treatment response (HCV RNA<25 IU/mL by PCR assay at 48 weeks) was observed in naïve genotype 1 patients in the triple therapy group compared to SOC alone (all randomized); Triple—37/53 (70%) vs SOC—27/49 (55%), one-tailed Fisher's exact test p=0.09.

Figure 14A:
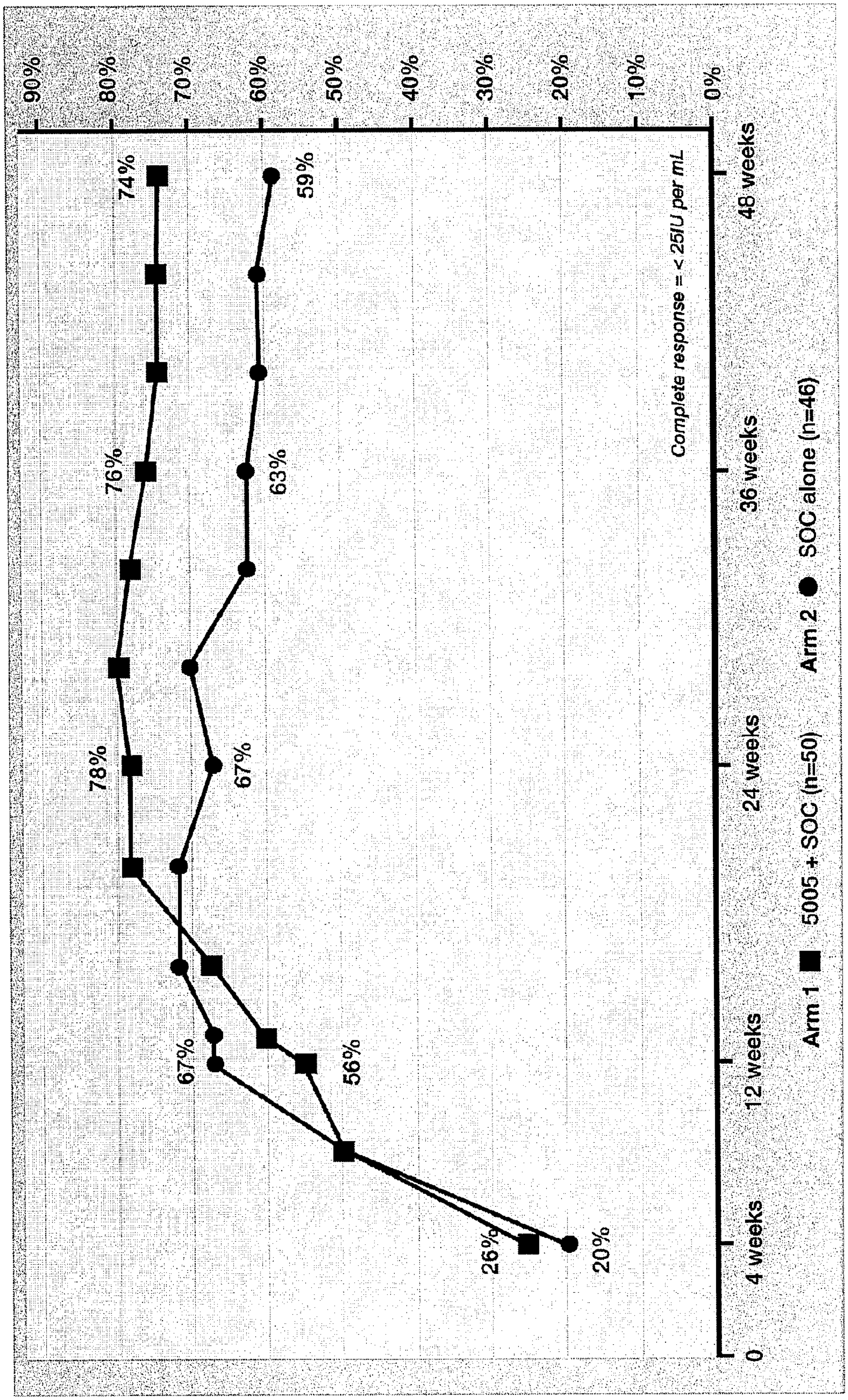

FIG. 14A is a graph reflecting the mITT (modified Intent to Treat) analysis, showing that, at 48 weeks after start of triple therapy improvement in end of treatment response (HCV RNA<25 IU/mL by PCR assay at 48 weeks) was observed in naïve genotype 1 patients in the triple therapy group compared to SOC alone (mITT; Triple 37/50 (74%) vs. SOC 27/46 (59%)).

Figure 14B:
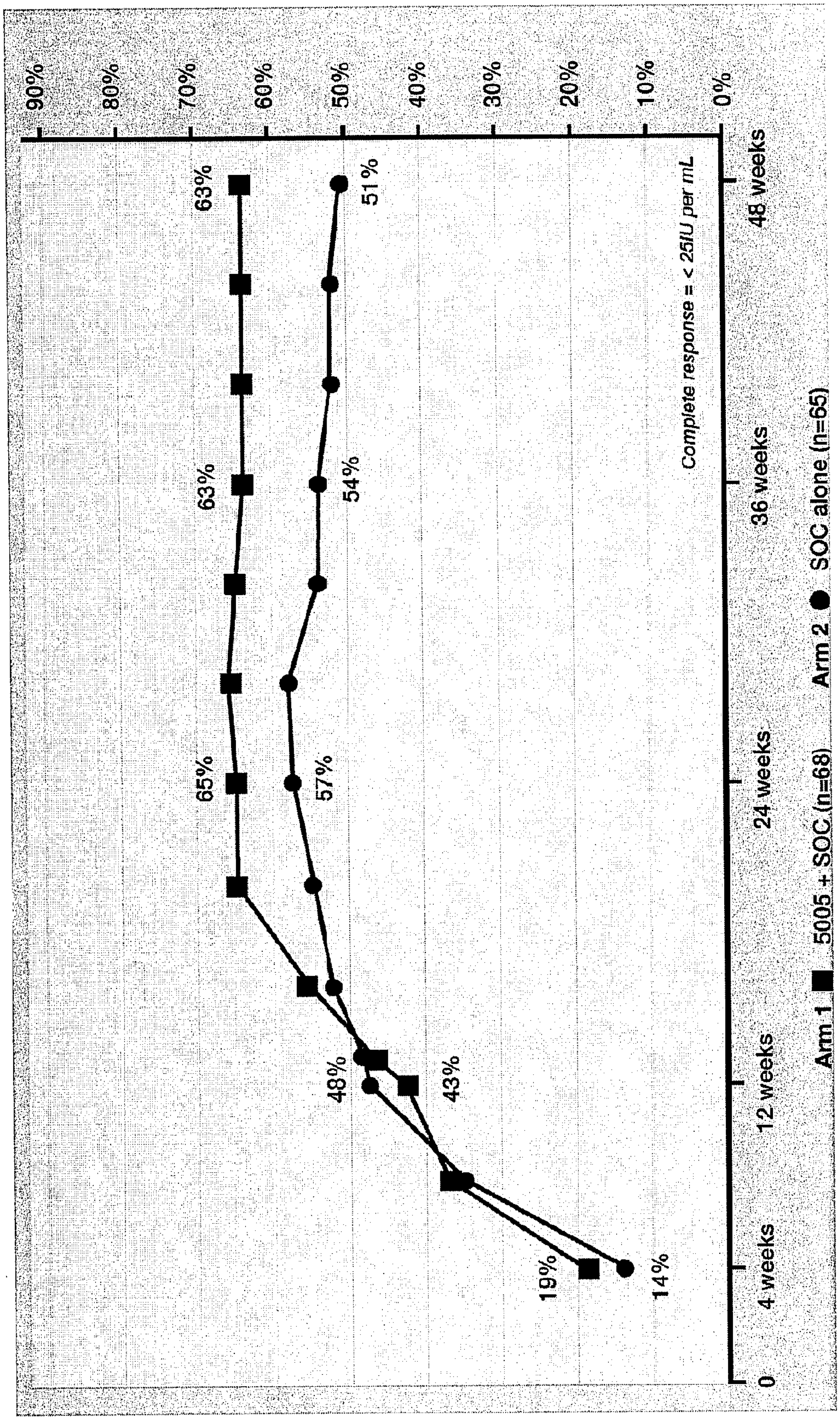

FIG. 14B is a graph reflecting the mITT (modified Intent to Treat) analysis, showing that, at 48 weeks after start of triple therapy improvement in end of treatment response (HCV RNA<25 IU/mL by PCR assay at 48 weeks) was observed in all patients in the triple therapy group (naïve and non-responders) compared to SOC alone (mITT; Triple 63% vs. SOC 51%).

Figure 15A:
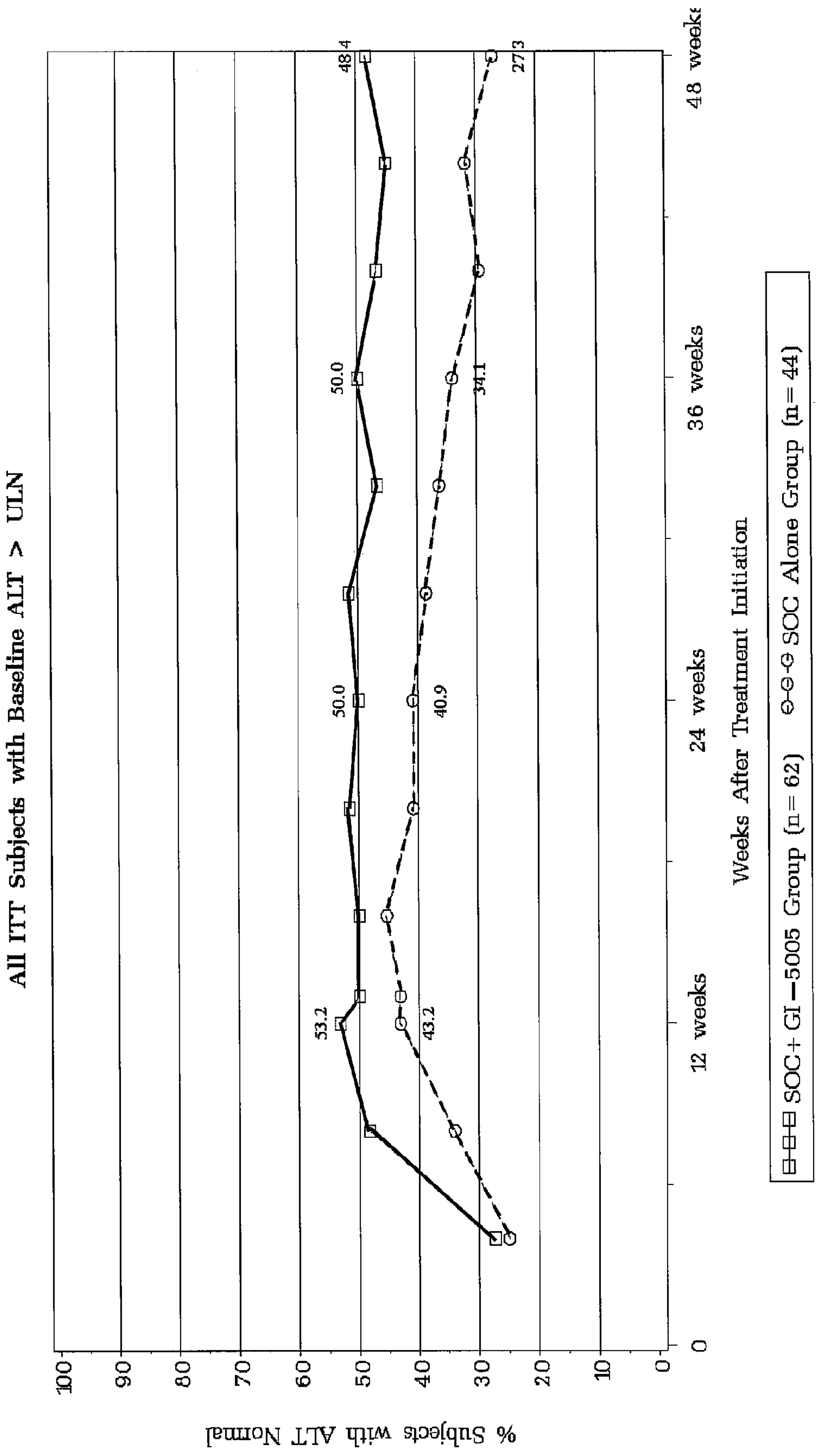

FIG. 15A is a graph showing that, at 48 weeks, triple therapy demonstrated an improvement in ALT normalization in the group of all subjects as compared to SOC.

Figure 15B:
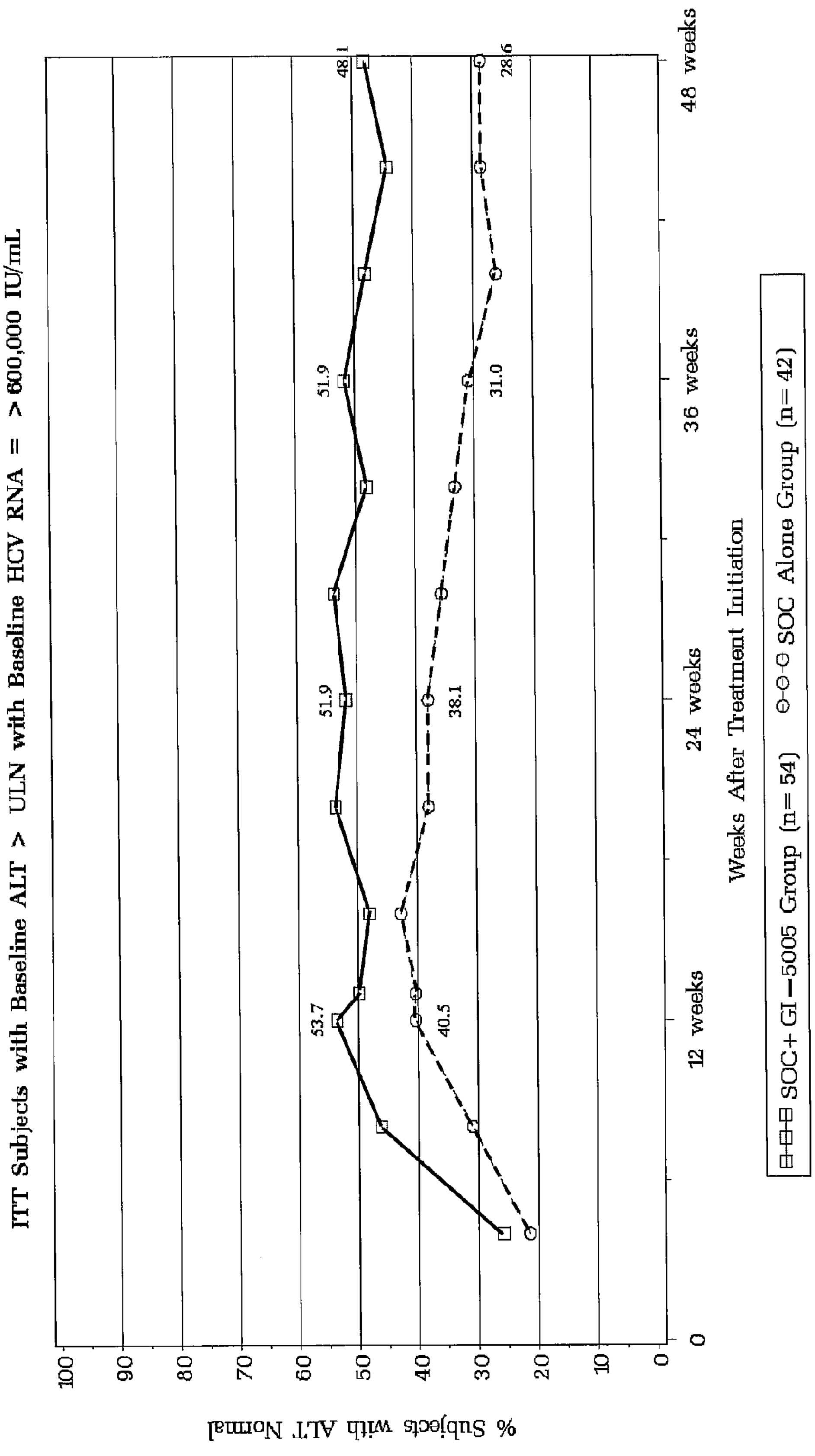

FIG. 15B is a graph showing that, at 48 weeks, triple therapy demonstrated an improvement in ALT normalization in the group of all subjects with a high viral load at baseline as compared to SOC.

Figure 15C:
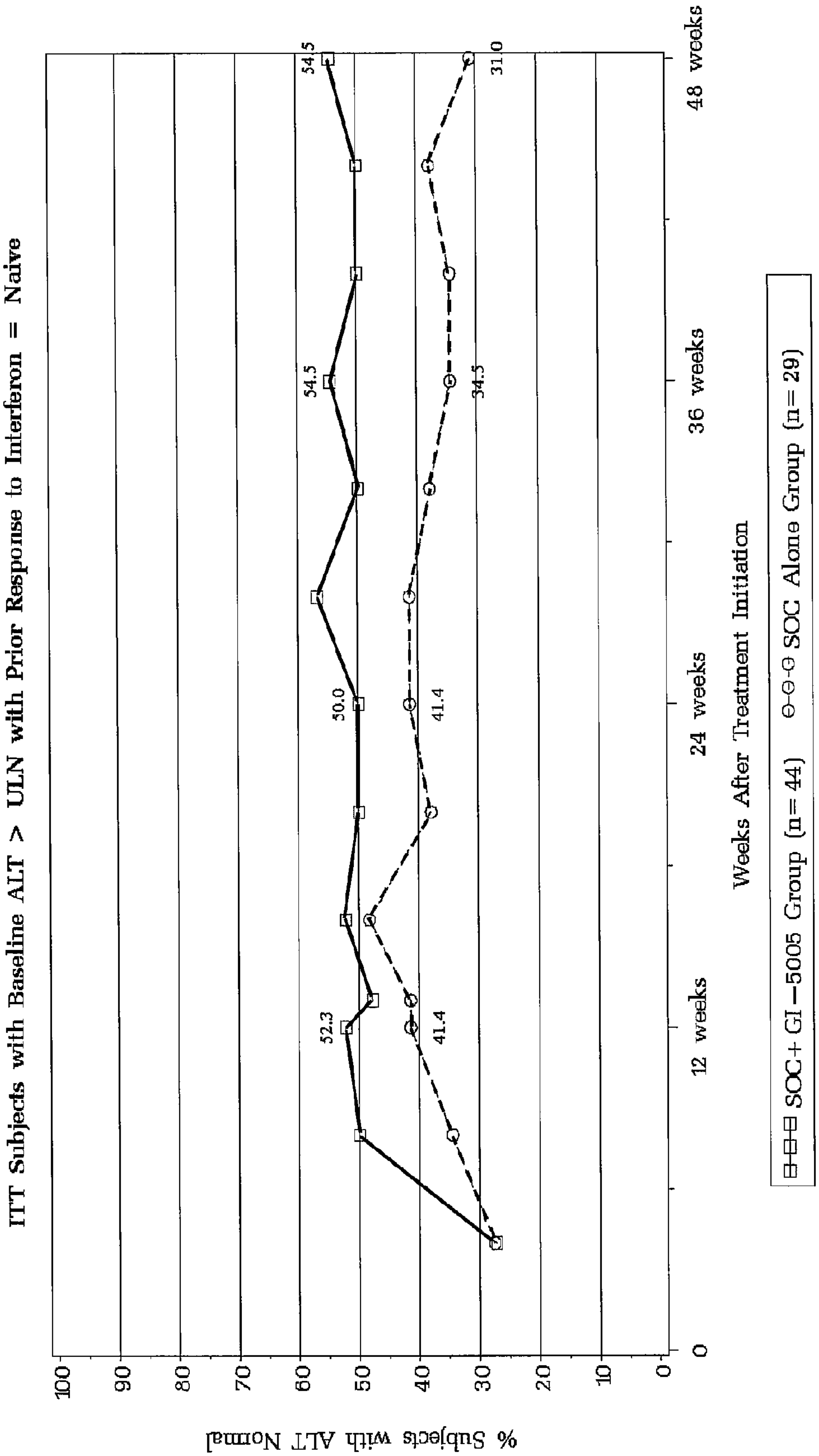

FIG. 15C is a graph showing that, at 48 weeks, triple therapy demonstrated an improvement in ALT normalization in the group of interferon-naïve subjects as compared to SOC.

Figure 15D:
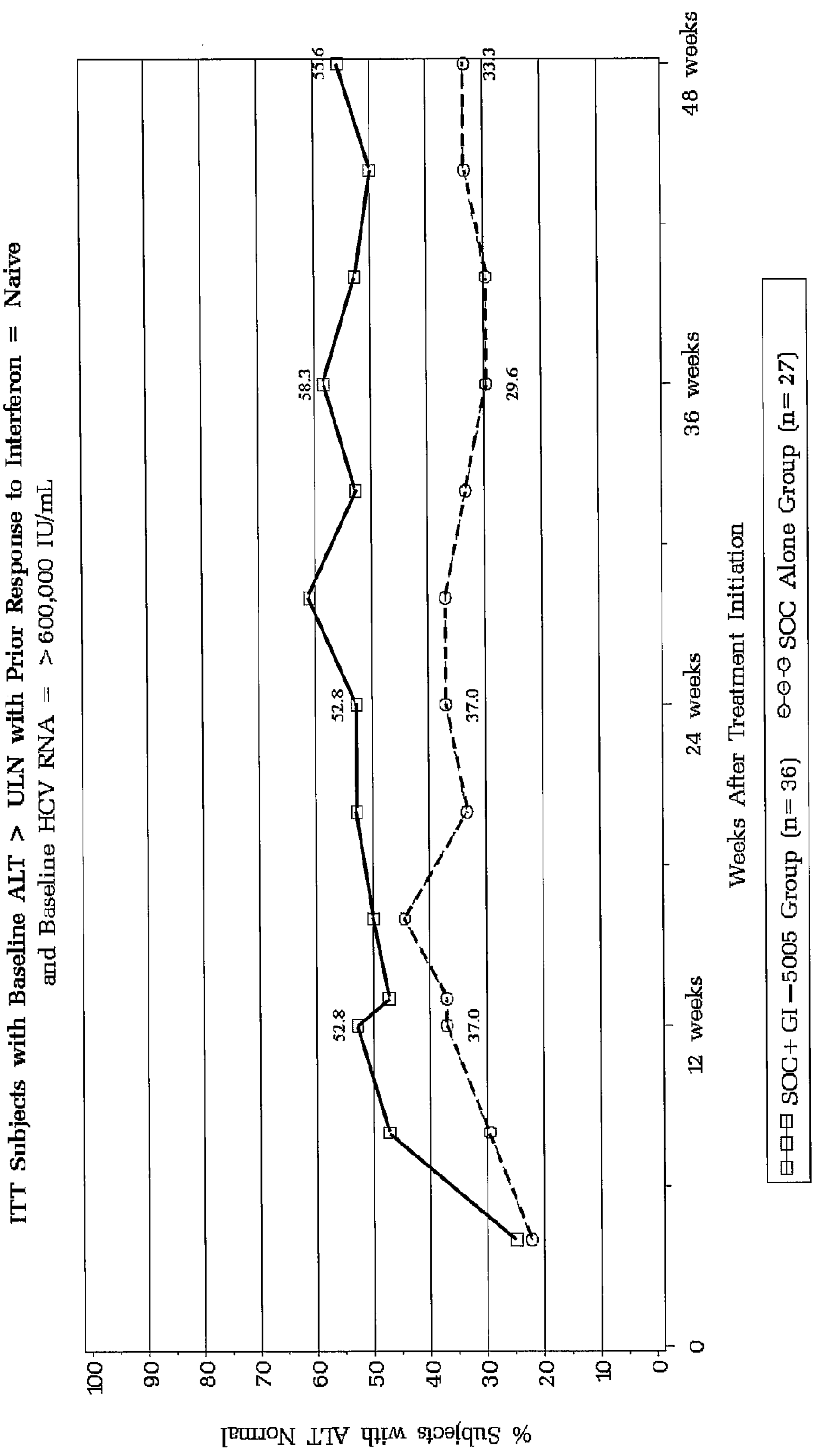

FIG. 15D is a graph showing that, at 48 weeks, triple therapy demonstrated an improvement in ALT normalization in the group of interferon-naïve subjects who had a high viral load at baseline as compared to SOC.

Figure 15E:
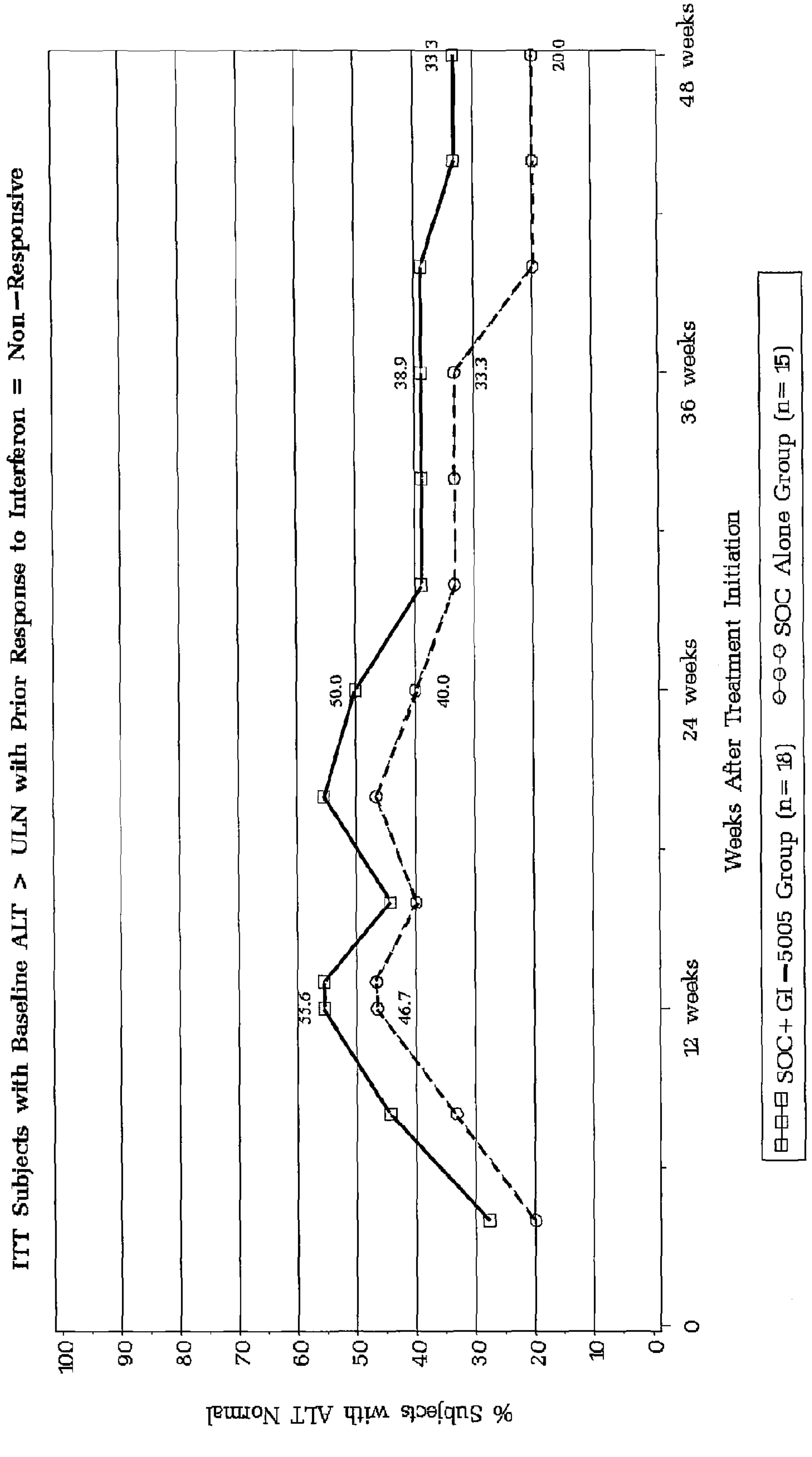

FIG. 15E is a graph showing that, at 48 weeks, triple therapy demonstrated an improvement in ALT normalization in the group of prior non-responders as compared to SOC.

DETAILED DESCRIPTION OF THE INVENTION

The present invention generally relates to a novel method for therapy for chronic hepatitis C virus (HCV) infection, which combines current Standard of Care Therapy (SOC; interferon therapy combined with anti-viral therapy) with immunotherapy (e.g., administration of an immunotherapeutic composition) in a manner that, as compared to SOC alone: improves the rate of early response to therapy as measured by early virologic markers (e.g., RVR and EVR), enlarges the pool of patients who will have sustained responses to therapy over the long term, offers shortened courses of therapy for certain patients, enables "rescue" of patients who are non-responders or intolerant to SOC therapy, improves liver function and/or reduces liver damage in patients, and enables the personalization of HCV therapy for a patient, which can result in dose sparing, improved patient compliance, reduced side effects, and improved long term therapeutic outcomes. Importantly, without being bound by theory, the inventors believe that the novel therapeutic protocol described herein will convert the current rate of Sustained Virologic Response (SVR) of patients infected with genotype I HCV and treated with SOC toward a rate more similar to that of patients infected with genotypes 2 or 3 HCV. Indeed, at ETR (48 weeks), genotype 1 naïve patients receiving the therapeutic protocol of the present invention had a higher complete response/preserved response (see Examples), as compared to the equivalent group receiving SOC alone. When extrapolated out to SVR, the inventors expect that the population of patients receiving the therapeutic protocol of the invention will have fewer post treatment relapses and improved SVR rates as compared to patients who received SOC only.

More particularly, in a phase 2 study (clinical trial) of the combination of immunotherapy plus SOC (triple therapy), the inventors have discovered that the triple therapy approach described herein results in improved viral kinetics and improved complete response rates in various patient groups during the 48 weeks of treatment, as well as improvements in liver function and/or reduced liver damage, as compared to SOC alone. In this study (FIG. 1), GI-5005, a whole, heat-killed *S. cerevisiae* immunotherapy product expressing high levels of HCV NS3 and Core antigens, was used in conjunction with peg-IFN/ribavirin (SOC) to treat subjects with genotype 1 chronic HCV infection. Patients (140 total enrolled) were randomized 1:1, and stratified by virologic response during their prior course of treatment in this open label trial. Arm 1 patients received a GI5005 monotherapy run-in consisting of five weekly followed by 2 monthly subcutaneous (SC) doses of 40 YU (1 YU=10,000,000 yeast) GI-5005 over 12 weeks (administered as 10 YU doses to four separate sites on the patient), followed by triple therapy consisting of monthly 40 YU GI-5005 doses plus pegIFN/ribavirin (administered for 48 weeks in naïve patients, 72 weeks in prior non-responders). Arm 2 patients received treatment with SOC alone (without antecedent GI-5005 monotherapy).

Four Week Treatment Endpoint (RVR)

The present inventors have discovered that administration of an immunotherapeutic composition in conjunction with a Standard of Care therapeutic approach (also referred to herein as "triple therapy") surprisingly resulted in a trend toward or statistically improved Rapid Virologic Response (RVR) rates in interferon-naïve patients (also referred to herein as "naïve" patients, i.e., patients who had not been previously treated with interferon or SOC) receiving triple therapy as compared to patients receiving SOC alone. At an interim timepoint, when most of the SOC subjects had reached the 4 week point after start of SOC, and when nearly half of the triple therapy subjects had reached the 4 week point after start of interferon/ribavirin therapy (i.e., following a 12 week run-in of immunotherapy alone, and then continuing immunotherapy once interferon/ribavirin was initiated), interferon-naïve patients treated with triple therapy had statistically improved RVR rates (47% RVR versus 20% RVR; p=0.03) as compared to patients receiving SOC alone. At this interim analysis, in patients who were prior non-responders to SOC (i.e., prior non-responders are patients who had previously failed to achieve EVR, or >2 log reduction in viral load, after 12 weeks of SOC), combined immunotherapy and SOC (i.e., triple therapy) indicated a trend toward an improved EVR and/or cEVR rate, as measured by statistically significant differences in second phase viral clearance kinetics (−1.16 log 10/mo. versus −0.88 log 10/mo; p=0.02). If these differences were modeled forward through 12 weeks (projecting to a 0.80 log 10 reduction advantage at 12 weeks), better EVR and cEVR rates were expected for patients receiving triple therapy.

Upon completion of all patients in both arms (SOC alone and triple therapy) through four weeks of interferon/ribavirin therapy, it was discovered that administration of an immunotherapeutic composition in conjunction with a Standard of Care therapeutic approach (triple therapy) resulted in improved 4 week kinetics for interferon-naïve and prior non-responder patients, and improved Rapid Virologic Response (RVR) rates in interferon-naïve patients, as compared to patients receiving SOC alone.

More specifically, at completion of four weeks of interferon/ribavirin therapy, among all patients receiving triple therapy, triple therapy resulted in a strong trend toward improved RVR rates (19.1% RVR versus 13.8% RVR; p=0.28), including in interferon-naïve patients (i.e., patients who had not been previously treated with SOC) as compared to patients receiving SOC alone (26.0% RVR versus 19.6% RVR; p=0.31). In addition, a 2.6-fold advantage favoring triple therapy was observed in the group of patients who were interferon-naïve and who began the trial with a baseline high viral load (high viral load is defined herein as >600,000 IU/ml HCV RNA levels) (20.0% RVR versus 7.7% RVR; p=0.1). The majority of naïve/low viral load patients achieved RVR in both treatment groups (triple therapy and SOC alone), contributing to the smaller observed advantage for triple therapy in the interferon-naïve group as a whole (which combined naïve patients having high or low viral loads at baseline). Moreover, there were no observed RVRs in the non-responder patients from either treatment arm, thereby producing lower absolute RVR rates in the analysis of all patients as a single group.

Moreover, upon completion of all patients in both arms through four weeks of interferon/ribavirin therapy, the trend toward favorable EVR, ETR and SVR rates resulting from triple therapy, as measured by second phase viral clearance kinetics, continued. More specifically, several patient subgroups showed an increased rate of second phase viral clearance which favored triple therapy at the four week point. In particular, three subgroups achieved statistical significance: (1) all patients, (2) prior non-responders; and (3) patients having a high viral load at baseline (with p=0.02, p=0.008, and p=0.02, respectively). Two subgroups showed strong trends favoring triple therapy: (1) interferon-naïve patients, and (2) patients who were both interferon-naïve and had a high viral load at baseline. Taken together, triple therapy demonstrated a ~2-fold improvement over four weeks in the linear rate of viral clearance (0.24-0.32 $\log_{10}$/month) compared with SOC alone in all relevant subgroups, including prior non-responders to interferon-based therapy. This improved rate of clearance projected to a 3 to 4 $\log_{20}$ improved reduction of virus if sustained for the full 48-72 week regimen. The improved rate of second phase viral kinetic clearance supports a role for the proposed mechanism of immunotherapy-induced, improved elimination of infected hepatic cells.

12 Week Treatment Endpoint (EVR) and 12 and 24 Week Liver Function Data

Upon completion of all patients in both arms (SOC alone and triple therapy) through 12 weeks of interferon/ribavirin therapy (EVR endpoint), triple therapy demonstrated an 8-12% improvement in EVR rates as compared to SOC alone in treatment naïve (interferon-naïve) patient subgroups. In particular, triple therapy EVR rates were improved in the subgroup containing all naïve subjects (67% achieving complete response for triple therapy versus 56% achieving complete response for SOC) and in the subgroup of those naïve subjects who also had a high baseline viral load (>600,000 IU/mL).

In addition, evaluation of markers of liver function or liver damage after all patients completed 12 weeks of therapy and after all patients completed 24 weeks of therapy demonstrated very strong trends toward liver function improvement and/or reduced liver damage in patients receiving triple therapy, as compared to those receiving SOC alone.

More specifically, naïve patient subgroups (all naïve and naïve/high viral load) receiving triple therapy demonstrated a 10-15% improvement in ALT normalization at both 12 and 24 weeks of therapy as compared to the same SOC subgroups (ALT normalization is defined as at least 2 ALT values<ULN on consecutive study visits for patients with ALT>ULN at Day 1). ALT is a well-validated measure of hepatic injury and serves as a surrogate for hepatic inflammation. In prior large hepatitis trials, reductions and/or normalization of ALT levels have been shown to correlate with improved liver function and reduced liver fibrosis as determined by serial biopsy.

In addition, after 24 weeks of therapy, triple therapy demonstrated increased proportions (up to 2-fold) of patients with categorically improved serum fibrotest scores and a decreased proportion (as much as 50% reduction) of patients with categorically worsened serum fibrotest scores compared to SOC (Fibrotest scores show the proportion of patients who improved from moderate to minimal fibrosis or from severe to moderate or minimal fibrosis, as measured by Fibrotest). These trends were reflected in all groups as shown in FIG. 11B (All treated, Naïve, Naïve HVL, and Non-responders).

Triple therapy at 24 weeks also demonstrated up to a 14% advantage in naïve patient subgroups (all Naïve and Naïve/HVL) with categorically improved serum Actitest scores, as compared to SOC (Acitest scores reflect the proportion of patients who improved from moderate to minimal necrosis or from severe to moderate or minimal necrosis, as measured by Actitest).

At the completion of both 12 and 24 weeks of therapy, GI-5005 triple therapy continued to be well tolerated, with triple therapy showing comparable discontinuation rates compared to SOC.

48 Week Treatment Endpoint (ETR)

Upon completion of all patients in both arms (SOC alone and triple therapy) through 48 weeks of interferon/ribavirin therapy, which is end of treatment (ETR endpoint), a higher percentage of naïve patients in the triple therapy group achieved or maintained a complete response as compared to patients receiving SOC alone. Specifically, an improvement in end of treatment response (ETR) (HCV RNA<25 IU/mL by PCR assay) was observed in treatment naïve (interferon-naïve) genotype 1 patients in the triple therapy group compared to SOC alone (Triple—37/53 (70%) vs SOC—27/49 (55%) (FIG. 13). A similar treatment effect was observed in all patients (Interferon-Naïve and Non-Responder) (data not shown). Complete response (HCV RNA<25 IU/mL) was also assessed in non-responders as a group at week 48 (all randomized); Triple-6/19 (32%) vs SOC-6/19 (32%). The mITT (modified Intent To Treat) analysis (analysis of only those patients enrolled in the study who actually received at least one treatment dose in the study) shows a consistent treatment effect of 15%; Triple 37/50 (74%) vs. SOC 27/46 (59%) (FIG. 14A) with week 48 complete virologic response rates that are comparable to those of recently reported protease inhibitor triple therapy regimens. A similar treatment effect was observed in all patients (naïve and non-responders) using mITT analysis (FIG. 14B; Triple 63% vs. SOC 51%).

These results demonstrate a substantial improvement in complete virologic response at week 48 in patients receiving GI-5005 triple therapy compared to SOC alone. This is the first example of a therapeutic vaccine delivering a substantial difference in a long term, clinically meaningful virologic endpoint such as complete virologic response. Furthermore, based on the immune-mediated mechanism of action of GI-5005, patients receiving GI-5005 triple therapy are expected to experience continued benefit in the post treatment period and should experience better ETR to SVR conversion.

Of interest by 48 weeks of treatment, viewing the complete responses over the course of the treatment period, is the observation (see FIG. 13) that patients receiving triple therapy, as a group, continued to gain complete responders past the time point at which the SOC alone group begins to lose responders. Without being bound by theory, the inventors believe that an additional positive effect of the use of immunotherapy with SOC is the ability to gain and/or sustain control of virally infected cells over a longer term via activation of the immune system against HCV. This is expected to result in fewer post-treatment relapses and accordingly, improved SVR rates, in the triple therapy groups as compared to the groups receiving SOC alone.

Accordingly, results of the phase 2 clinical trial at 48 weeks after therapy indicate improvements in viral kinetics, RVR, EVR, and ETR in genotype 1 patients, and particularly in interferon-naïve patient groups, which are expected to lead to an advantage in virologic response (complete response) for triple therapy compared to SOC, as measured by SVR. In addition, the demonstrated improvements in ALT normalization, Fibrotest, and Actitest scores are expected to lead to an advantage for liver histology for triple therapy compared to SOC as measured by paired biopsy assessment. In addition, triple therapy is expected to be useful to rescue patients who would otherwise fail therapy under SOC alone. Finally, the use of immunotherapy with SOC as described herein is expected to reduce or eliminate viral mutational escape that is known to result from the use of various anti-viral small molecule drugs.

The results described herein are surprising, because while the use of an agent that stimulates an adaptive cellular immune response was expected to improve later stage endpoints as compared to SOC alone, including Sustained Virologic Response (SVR) rates, it was not predictable that the addition of immunotherapy to interferon-anti-viral therapy would show significant improvement in patient responses at early virologic endpoints (i.e., in phase 1 viral kinetics, which reflect the efficiency of inhibition of viral replication (driven by rapid peripheral viral clearance), as compared to SOC alone. It was expected that the stimulation of the HCV-specific cellular immune response would have the most significant effects later in the course of treatment, favoring improved clearance of the virus-infected hepatic cells (the rate limiting portion of the viral dynamics profile), while the interferon/anti-viral therapy would be primarily responsible for early viral load reduction by inhibiting viral replication directly; thus, the immunotherapy would complement the direct anti-viral effects of the interferon/anti-viral-based therapy and substantially improve SVR. The impact of immune system stimulation during early clearance of the virus (pre-RVR) by interferon/anti-viral therapy (phase 1 viral clearance) was not expected to be statistically significant or show strong trends favoring the addition of immunotherapy as compared to that of SOC alone.

However, the effect of the added immunotherapy was striking and surprising, because the effect on early virologic markers appeared extremely early during the course of interferon/anti-viral therapy, in some cases being detected just 8 days after the commencement of the interferon/anti-viral therapy. This result indicates that the addition of immunotherapy to an HCV SOC protocol is likely to be synergizing with the SOC interferon/anti-viral therapy, and can be expected to have a greater impact on early viral kinetics than SOC alone, as well as leading to improved second phase viral kinetics and improved sustained viral clearance. These results can lead to dose sparing regimens of SOC therapy (i.e., reducing or eliminating SOC components) for at least some patients, and is expected to allow at least some patients who would otherwise fail SOC therapy to remain on therapy, perhaps a modified therapy, and achieve a positive outcome.

Moreover, it was unexpected that the combination of immunotherapy with SOC would result in a gain in complete responders over a longer period of time than is achieved using SOC alone, and it was also unexpected that the combination of immunotherapy with SOC would be able to sustain complete responses through the end of treatment to such a greater degree than SOC alone.

The observed complete response rates with the addition of immunotherapy to SOC indicate the ability to reduce on-treatment relapse (breakthrough) and post-treatment relapse (relapse) as compared to the rates using SOC alone. Moreover, given that the immunotherapy component of the triple therapy protocol of the invention is believed to control hepatic clearance in part through activation of the immune response against HCV, and particularly the cellular immune response, emergence of mutational escape is expected to be lower or absent in patients receiving triple therapy as described herein, as compared to patients receiving other small molecule anti-viral therapies. Small molecule therapies are known to "pressure" a virus to mutate, resulting in the emergence of viral escape mutants against which the small molecule therapies are not effective.

In addition, the improvements in liver function, ALT normalization, Fibrotest, and Actitest scores in patients receiving triple therapy as compared to SOC therapy are expected to lead to an advantage for liver histology for triple therapy compared to SOC as measured by paired biopsy assessment. As discussed above, sequelae to chronic HCV infection can include liver cirrhosis, hepatic failure and liver cancer; therefore, a reduction in liver damage resulting from HCV infection (or improved liver function during or after treatment for HCV infection) is an important clinical benefit to a patient suffering from chronic HCV infection.

Finally, the immunotherapy approach described herein is well-tolerated and is expected to have lower discontinuation rates and fewer non-compliance issues than expected from small molecule approaches to treating HCV infection. For example, some small molecule anti-viral approaches report toxicities due to anemia and rash, or require such frequent dosing when used under current protocols, that non-compliance is a real issue. The immunotherapy protocol of the invention can be administered in convenient monthly doses, and has few reported immunotherapy product-related safety issues, dose limiting toxicities, or discontinuations. In addition, the immunotherapy component of the invention may lead to the use of dose-sparing regimens of SOC and other drugs, thereby improving patient tolerance and compliance of treatment for HCV.

Without being bound by theory, the inventors believe that the results presented herein at both early and later virologic endpoints are due to the combined and complementary or synergistic effects of the three components of the triple therapy, which, in one aspect of the invention, may be enhanced by the timing of administration of the three components to the patient. Specifically, the inventors believe that an initial period of immunotherapy as a monotherapy, followed by the addition of treatment with interferon and/or anti-viral therapy (triple therapy), is one effective protocol for this triple therapy, and results in the improvement in early virologic endpoints. In this protocol, the immune system is initially primed and boosted to respond to HCV antigens by administration of an immunotherapeutic composition that elicits T cell-mediated immune responses against HCV antigens. While monotherapy with an immunotherapeutic composition has previously been shown by the inventors to result in decreased viral loads and improved liver function in patients over time (based on phase Ib clinical trial data), the impact of this type of immunotherapy on phase 1 viral kinetics when provided in combination with additional therapeutic agents was not previously known or expected to be significant.

Accordingly, the inventors believe that combination of immunotherapy with Standard of Care (SOC) represents a novel triple therapy approach that is expected to result in improved SVR rates and can also serve as an optimized backbone therapy to which other antiviral agents could be added. Indeed, combination of immunotherapy with different inhibitors of viral replication, such as small molecule polymerase and protease inhibitors is expected to result in the ability to spare or completely eliminate components of the current SOC (interferon or ribavirin), as well as spare dosing of the small molecules, resulting in better patient tolerance of therapy for HCV infection and better patient compliance.

By commencing patient treatment with an initial period of immunotherapy using a composition such as that described in detail herein, the immune system is activated and T cell responses (i.e., CD4+ responses and/or CD8+ responses) to HCV viral antigens are elicited, in the absence of additional factors that might inhibit or retard the expansion of such responses. After several rounds of boosting the immune system against HCV antigens, the interferon/anti-viral therapy is introduced; however, in one embodiment (discussed below), it may be desirable to begin the interferon therapy at the same time as the immunotherapy (to enhance the effects of the immunotherapy) and introduce anti-viral therapy at a later timepoint.

Type I interferons are secreted by host cells in response to abnormally large amounts of dsRNA in a cell (e.g., as a result of infection of a cell by an RNA virus, such as HCV). As a result of activation of Toll Like Receptor 3 (TLR3), interferon production is triggered in cells of the innate immune system, which in turn causes cells to activate genes and produce proteins that prevent viral replication and inhibit normal cell ribosome function, thus killing the virus and likely also the infected host cell. Therefore, administration of type I interferon has immediate anti-viral effects on HCV infection. However, type I interferons have also been associated with immune system effects that are believed by the present inventors to be synergistic with the cell mediated immunity elicited by immunotherapeutic compositions of the invention, including upregulation of major histocompatibility genes in antigen presenting cells and target cells, as well as upregulation of dendritic cells, natural killer cells, and $CD8^+$ cytotoxic T lymphocytes (Caruntu and Benea, *J Gastrointestin Liver Dis* 2006; 15:249-256). Administration of interferon gives the already primed and boosted immune system (as a result of immunotherapy as discussed above), now poised to eliminate virally infected cells, additional assistance by enhancing antigen presenting cell function, among other mechanisms.

Ribavirin is a nucleoside antimetabolite drug that interferes with viral replication. Therefore, administration of this anti-viral drug (or other drugs that interfere with viral life cycle) complements the anti-viral activity of interferons in the current SOC for HCV. Other anti-viral drugs are also known and have anti-protease, anti-polymerase, or other anti-viral effects. However, ribavirin is also known to enhance host T cell-mediated immunity against viral infection by switching the type of immune response in the host from a Th2-type response to a Th1-type response (Tam et al., *J. Hepatol* 1999; 30:376-382; Hultgren et al.; *J. Gen. Virol.* 1998; 79:2381-2391). Administration of anti-virals having similar functional characteristics as ribavirin would therefore also be expected to enhance the primed and boosted immune system by enhancing the anti-viral Th1-type response that favors T cell immunity and improved viral clearance. Because the immunotherapeutic compositions useful in the present invention are characterized by a Th1-type response, the additional effects of ribavirin therapy are expected to be additive or even synergistic.

In an additional embodiment of the invention, the triple therapy commences immediately (all three components are administered over the same time period). In this protocol, the complementary effects of immunotherapy, interferon therapy, and anti-viral therapy are expected to occur, and second phase viral kinetics are expected to be significantly improved or strongly trend toward improved as compared to current SOC alone. Under this protocol, the early the enhanced and possibly synergistic effects of immunotherapy on later virologic endpoints is expected.

In another embodiment, immunotherapy is commenced in combination with interferon therapy, which is followed at least 4-12 weeks later with the addition of anti-viral therapy. In this embodiment, the combination of interferon to increase the adaptive immune response and upregulate immune system effects that are believed by the present inventors to be synergistic with cell mediated immunity is combined with a highly effective immunotherapy that will elicit a T cell-mediated immune response. After the initial period of priming and boosting of the immune system, the additional effects of anti-viral treatment are added (via ribavirin and/or another anti-viral agent).

Finally, the present inventors believe that the surprising potent and early effects of the present method have additional advantages over current SOC alone. Under current SOC therapy, patients who fail to achieve EVR at 12 weeks of therapy are typically removed from therapy, due to the extremely poor prospects of reaching SVR versus the side effects of continued interferon/anti-viral treatment. Such patients can be referred to herein as patients who are "predicted to fail" combination interferon/anti-viral therapy, or "non-responders". Because the method of the invention results in improved viral kinetics, it is expected that not only will fewer patients be removed from therapy, the ability to screen patients for continued or modified therapy, or rescue patients who would otherwise fail therapy, versus discontinuation of therapy, will improve. In other words, during a triple therapy protocol including immunotherapy as described herein, the inventors believe that some patients who would otherwise have failed therapy under current SOC guidelines will now be identified as being likely to respond under a longer and/or modified course of therapy, rather than being immediately removed from therapy. This is because the addition of immunotherapy to the protocol not only achieves improved viral kinetics that can be detected in a larger number of patients, but also provides additional markers by which patient response can be evaluated, including, but not limited to, anti-HCV T cell responses and improvements in liver function (and/or decrease in liver damage). Moreover, as illustrated by complete response data provided herein (e.g., see FIG. 13), patients on triple therapy may be able to continue therapy beyond the "predicted to fail" cut-off point for SOC (e.g., 12 weeks), since the triple therapy method described herein appears to result in a continued gain of complete responders at time points beyond which the numbers of complete responders under SOC alone typically wane.

Indeed, the method of the invention enables the "personalization" of HCV therapy via the addition of a therapy (immunotherapy) that provides novel markers for evaluating efficacy, improved early responses, a higher incidence of complete responses which is expected to result in a higher incidence of SVR and fewer relapses, fewer breakthroughs during therapy, improved liver function/decreased liver damage, and importantly, few reported immunotherapy product-related safety issues, dose limiting toxicities, or discontinuations. More specifically, patients can be evaluated at early virologic endpoints during triple therapy as described herein, and possibly further evaluated for immunological responses to identify those patients for whom reductions in dose amounts, dosing frequency, and/or length of treatment, with respect to any of the immunotherapy, interferon therapy, and/or anti-viral compound therapy, can be prescribed. It is expected that the efficacy of the immunotherapy, which is well-tolerated to date, will allow certain patients to substantially reduce the dosing and/or the course of the current SOC components or other anti-viral components (e.g., small molecules, such as protease inhibitors), thereby reducing the side effects that accompany SOC and other small molecule therapies. Other patients may require a longer course of therapy to achieve results, but will be able to tolerate the therapy due to reduced dosing or even elimination of the interferon and/or anti-viral arms of the therapy.

In some patients, and particularly those who are identified as intolerant to interferon therapy, a modified schedule of therapy can be prescribed which may include continued immunotherapy alone, or a double therapy protocol of immunotherapy and anti-viral therapy. Intolerance to interferon, while somewhat subjective, is defined herein as side effects of interferon therapy that are sufficiently severe that it is determined that lower dose or removal from therapy is advisable. Symptoms of intolerance can range from severe flu-like symptoms, loss of libido, depression, suicidal ideation, to severe pancytopenia. Accordingly, the methods of the invention offer new salvage or rescue opportunities for patients who would currently be removed from therapy altogether, as well as possibilities to tailor the treatment of a patient to achieve the optimal viral response using the most tolerable course of therapy.

One embodiment of the invention relates to a method to treat chronic hepatitis C virus (HCV) infection, which includes the step of administering to a subject an immunotherapeutic composition including at least one HCV antigen or immunogenic domain thereof; and further administering to the subject at least one or more additional therapies. In one aspect, the one or more additional therapies include administering one or both of at least one interferon and at least one anti-viral compound. In this embodiment, the additional therapies, such as the interferon and anti-viral compound, are first administered at least 4 weeks after the immunotherapeutic composition is first administered. In other aspects of this embodiment, the additional therapies such as interferon and anti-viral compound are first administered at least 4 to 12 weeks after the immunotherapeutic composition is first administered, and in another aspect, at least 12 weeks after the immunotherapeutic composition is first administered. Preferably, interferon is administered to the subject weekly for between 24 and 48 weeks, or longer, and over the same period of time, the anti-viral compound is administered daily. In one aspect, the anti-viral compound is ribavirin. In another aspect, the interferon is administered to the subject during concurrent anti-viral therapy every 2, 3 or 4 weeks, for at least 24 weeks, 48 weeks, or longer. In one embodiment, the dosing of anti-viral compound is daily, every 2 days, every 3 days, every 4 days, every 5 days, every 6 days, or weekly, with daily being one preferred embodiment.

Ribavirin is an example of an anti-viral compound useful in the invention, although the invention is not limited to this anti-viral compound. Ribavirin is a synthetic nucleoside analogue. Ribavirin is commercially available in 200 mg tablets or capsules, although any suitable form of dose or delivery type is encompassed by the invention. The dose can be varied according to the preferences and recommendations of the physician, and whether the ribavirin is combined interferon, and it is within the abilities of those of skill in the art to determine the proper dose. A suitable dose of ribavirin, when used in conjunction with interferon, can range from approximately 800 mg to approximately 1200 mg daily, including any increment in between these doses (e.g., 900 mg, 1000 mg, 1100 mg, etc.). Typically, dosing is determined based on body weight, where persons of higher weight take a higher dose of ribavirin. In a preferred embodiment, ribavirin is administered daily at between 1000 mg (subject<75 kg) to 1200 mg (subject≥75 kg), administered orally in two divided doses. The dose is preferably individualized to the patient depending on baseline weight and tolerability of the regimen (according to product directions).

Interferon is typically administered by intramuscular or subcutaneous injection, and can be administered in a dose of between 3 and 10 million units, with 3 million units being preferred in one embodiment. In another embodiment, the recommended dose of interferon when used in combination with ribavirin for chronic hepatitis C is 180 μg (1.0 mL vial or 0.5 mL prefilled syringe) once weekly (e.g., for PEGASYS®).

Doses of interferon are administered on a regular schedule, which can vary from 1, 2, 3, 4, 5, or 6 times a week, to weekly, biweekly, every three weeks, or monthly. A typical dose of interferon that is currently available is provided weekly, and that is a preferred dosing schedule for interferon, according to the present invention. The dose amount and timing can be varied according to the preferences and recommendations of the physician, as well as according to the recommendations for the particular interferon being used, and it is within the abilities of those of skill in the art to determine the proper dose.

Preferably, when the course of interferon and anti-viral compound therapy begins, additional doses of the immunotherapeutic composition are administered over the same period of time, or for at least a portion of that time, and may continue to be administered once the course of interferon and anti-viral compound has ended. However, the dosing schedule for the immunotherapy over the entire period may be, and is preferably, different than that for the interferon and/or anti-viral compound. For example, the immunotherapeutic composition may be administered on the same days or at least 3-4 days after the last given (most recent) dose of interferon (or any suitable number of days after the last dose), and may be administered weekly, biweekly, monthly, bimonthly, or every 3-6 months. During the initial period of monotherapy administration of the immunotherapeutic composition, the composition is preferably administered weekly for between 4 and 12 weeks, followed by monthly administration (regardless of when the additional interferon/anti-viral therapy is added into the protocol). In one aspect, the immunotherapeutic composition is administered weekly for five weeks, followed by monthly administration thereafter, until conclusion of the complete treatment protocol.

Another embodiment of the invention relates to a method to treat chronic hepatitis C virus (HCV) infection, comprising administering to a subject an immunotherapeutic composition comprising at least one HCV antigen or immunogenic domain thereof, and further administering to the subject at least one additional therapy, which may include administering one or both of at least one interferon and at least one anti-viral compound. In this embodiment, the immunotherapeutic composition is administered at least 1 to 4 weeks after the additional therapies (e.g., interferon and/or anti-viral compound) are first administered, and in one aspect, between 4 and 12 weeks after the additional therapies (e.g., interferon and/or anti-viral compound) are first administered, and in another aspect, at least 12 weeks after the additional therapies (e.g., interferon and/or anti-viral compound) are first administered. In this embodiment, a patient can begin combined interferon and anti-viral therapy (SOC) or monotherapy (e.g., interferon therapy alone) and then begin immunotherapy at a later timepoint. For example, the patient may be determined to be intolerant to or likely to fail SOC alone and be moved onto immunotherapy as a monotherapy or as a double or triple therapy with interferon and/or anti-viral therapy. In the latter case, the continued administration of interferon and/or anti-viral therapy can be prescribed in a dose sparing manner, if desired, to reduce the side effects that accompany these therapeutic approaches. In addition, initial monotherapy with interferon alone may enhance the later addition of immunotherapy, by activating the innate immune response and further activating antigen presenting cells to respond more readily to the adaptive immune response.

In another aspect, administration of the immunotherapeutic composition and an interferon can be administered together (concurrently) initially, followed by a monotherapy of immunotherapeutic composition, or followed by the addition of an anti-viral compound for triple therapy. As used herein, concurrent use does not necessarily mean that all doses of all compounds are administered on the same day at the same time. Rather, concurrent use means that each of the therapy components (e.g., immunotherapy and interferon therapy, and the anti-viral therapy, if added) are started at approximately the same period (within hours, or up to 1-7 days of each other), noting that each component may have a different dosing schedule (e.g., interferon weekly and immunotherapy monthly, with addition of daily doses of ribavirin, etc.).

Yet another embodiment of the invention relates to a method to treat chronic hepatitis C virus (HCV) infection, comprising administering to a subject an immunotherapeutic composition comprising at least one HCV antigen or immunogenic domain thereof, and further administering to the subject at least one or more additional therapies, such as administering one or both of at least one interferon and at least one anti-viral compound. In this embodiment, the immunotherapeutic composition is administered after the final doses of additional therapies (e.g., interferon and/or anti-viral compound) are administered. This method is expected to be primarily useful for the patient who is intolerant to current SOC (e.g., interferon and ribavirin). Removal of the patient from SOC followed by immunotherapy using an immunotherapeutic composition of the invention is expected to be useful to salvage or rescue such patients from total HCV treatment failure.

In yet another embodiment, the invention includes a method to treat chronic hepatitis C virus (HCV) infection, comprising administering to a subject an immunotherapeutic composition comprising at least one HCV antigen or immunogenic domain thereof and at least one interferon, and further administering to the subject at least one anti-viral compound. In this embodiment, the anti-viral compound is first administered at least 4 weeks after the immunotherapeutic composition and interferon are first administered.

The invention also includes a method to treat chronic hepatitis C virus (HCV) infection, comprising administering to a subject an immunotherapeutic composition comprising at least one HCV antigen or immunogenic domain thereof, at least one interferon, and at least one anti-viral compound, wherein the immunotherapeutic composition, the at least one interferon and the at least one anti-viral compound are administered over the same period of time (concurrently).

One embodiment of the invention relates to a method to increase the frequency of rapid virologic responses (RVR) and/or early virologic responses (EVR) in a population of subjects chronically infected with hepatitis C virus (HCV), as compared to RVR and EVR in a population of subjects chronically infected with HCV and treated only with combination interferon and anti-viral therapy. The method includes administering to the population of subjects an immunotherapeutic composition that elicits a T cell-mediated immune response against one or more HCV antigens in combination with administration of at least one interferon and at least one anti-viral compound. Preferably, the immunotherapeutic composition is first administered at least 4 weeks prior to the first administration of the combination of interferon and anti-viral compound, and in one aspect, the immunotherapeutic composition is first administered at least 12 weeks prior to the first administration of the combination of interferon and anti-viral compound. In another aspect, the immunotherapeutic composition is first administered after the first administration of the combination of interferon and anti-viral compound, and in one aspect, is administered after the administration of the interferon and/or anti-viral therapy has ended or is discontinued.

Another embodiment of the invention relates to a method to enhance the conversion of rapid virologic responses (RVR) and/or early virologic responses (EVR) to sustained virologic responses (SVR) in a population of subjects chronically infected with hepatitis C virus (HCV), as compared to the conversion of RVR and/or EVR to SVR in the same population that is treated only with interferon and anti-viral therapy, the method comprising administering to the population of subjects an immunotherapeutic composition that elicits a T cell-mediated immune response against one or more HCV antigens in combination with at least one interferon and at least one anti-viral compound. In one aspect, the immunotherapeutic composition is first administered at least 4 weeks prior to the first administration of the combination of interferon and anti-viral compound, and in one aspect, the immunotherapeutic composition is first administered at least 12 weeks prior to the first administration of the combination of interferon and anti-viral compound. In this aspect of the invention, the method can increase the number of patients who achieve SVR in a population of patients with chronic HCV infection. In another aspect, the immunotherapeutic composition is first administered after the first administration of the interferon and/or anti-viral compound, and in one aspect, is administered after the administration of the interferon and/or anti-viral therapy has ended or is discontinued.

Yet another embodiment of the invention relates to a method to increase the number of complete responders in a population of subjects chronically infected with hepatitis C virus (HCV), as compared to the number of complete responders in a population of subjects chronically infected with HCV that is treated only with interferon and anti-viral therapy. The method includes administering to the population of subjects an immunotherapeutic composition that elicits a T cell-mediated immune response against one or more HCV antigens in combination with at least one interferon and at least one anti-viral compound. In one aspect, the immunotherapeutic composition is first administered at least 4 weeks prior to the first administration of the combination of interferon and anti-viral compound, and in one aspect, the immunotherapeutic composition is first administered at least 12 weeks prior to the first administration of the combination of interferon and anti-viral compound. In another aspect, the immunotherapeutic composition is first administered after the first administration of the interferon and/or anti-viral compound, and in one aspect, is administered after the administration of the interferon and/or anti-viral compound has ended or is discontinued.

Another embodiment of the invention relates to a method to reduce the number of breakthrough subjects during treatment or the number of relapsers post-treatment in a population of subjects chronically infected with hepatitis C virus (HCV), as compared to the number of breakthroughs during treatment or the number of relapses post-treatment in a population of subjects chronically infected with HCV that is treated only with interferon and anti-viral therapy. The method includes administering to the population of subjects an immunotherapeutic composition that elicits a T cell-mediated immune response against one or more HCV antigens in combination with at least one interferon and at least one anti-viral compound. In one aspect, the immunotherapeutic composition is first administered at least 4 weeks prior to the first administration of the combination of interferon and anti-viral compound, and in one aspect, the immunotherapeutic composition is first administered at least 12 weeks prior to the first administration of the combination of interferon and anti-viral compound. In another aspect, the immunotherapeutic composition is first administered after the first administration of the interferon and/or anti-viral compound, and in one aspect, is administered after the administration of the interferon and/or anti-viral compound has ended or is discontinued.

Another embodiment of the invention relates to a method to inhibit the emergence of drug-resistant HCV mutations, the method comprising administering to the population of subjects an immunotherapeutic composition that elicits a T cell-mediated immune response against one or more HCV antigens in combination with at least one or more additional therapies. In one aspect, the additional therapies include interferon and an anti-viral compound. In one aspect, the immunotherapeutic composition is first administered at least 4 weeks prior to the first administration of the combination of the additional therapies, and in one aspect, the immunotherapeutic composition is first administered at least 12 weeks prior to the first administration of the additional therapies. In another aspect, the immunotherapeutic composition is first administered after the first administration of the additional therapies, and in one aspect, is administered after the administration of the additional therapies has ended or is discontinued.

Yet another embodiment of the invention relates to a method to treat a subject who is chronically infected with HCV, the steps including: (a) administering an immunotherapeutic composition that elicits a T cell-mediated immune response against one or more HCV antigens to the subject for at least 4 to 12 weeks, followed by administering interferon and anti-viral concurrently with continued administration of the immunotherapeutic composition; (b) determining the rapid virologic response (RVR) of the subject at about 4 weeks after the first administration of interferon and anti-viral compound; and (c) reducing the dosage and/or frequency and/or length of interferon/anti-viral compound therapy in subjects with an RVR that is statistically significantly greater than the expected RVR of a subject treated with combination interferon-anti-viral compound therapy alone. In another embodiment, if the subject has an RVR that is not statistically significantly greater than the expected RVR of a subject treated with combination interferon-anti-viral compound therapy alone, then step (c) includes the process of either: (1) continuing the dosage and/or frequency and/or length of immunotherapy and/or interferon/anti-viral compound therapy in such subjects; or (2) increasing the dosage and/or frequency and/or length of immunotherapy and/or interferon/anti-viral compound therapy in such subjects. In one aspect, it may be preferable to increase the immunotherapy dosage and/or frequency and/or length of time for administration for such subjects, while allowing the interferon/anti-viral therapy to be discontinued.

Another embodiment of the invention relates to a method to continue treatment of a chronically HCV-infected subject who is predicted to fail combination interferon-anti-viral compound therapy, comprising administering to the subject an immunotherapeutic composition that elicits a T cell-mediated immune response against one or more HCV antigens. In one aspect, the subject continues receiving combination interferon-anti-viral compound therapy during the period of time in which the immunotherapeutic composition is administered.

Yet another embodiment of the invention relates to a method to continue treatment of a chronically HCV-infected subject who is intolerant to combination interferon-anti-viral compound therapy, comprising ceasing the combination therapy and administering to the subject an immunotherapeutic composition that elicits a T cell-mediated immune response against one or more HCV antigens. In one embodiment, instead of ceasing the combination therapy, the dosage and/or frequency of dosing of the combination therapy is reduced to a level that is tolerated by the subject, while immunotherapy is concurrently administered.

The immunotherapeutic compositions useful in all of the methods of the present invention include at least one HCV antigen or immunogenic domain thereof, which is formulated in a composition such that the composition elicits a T cell-mediated immune response against one or more HCV antigens. Preferably, the composition has one or more of, and more preferably, 2, 3, 4, or all of, the following characteristics: (a) stimulates one or more pattern recognition receptors effective to activate an antigen presenting cell; (b) upregulates adhesion molecules, co-stimulatory molecules, and MHC class I and class II molecules on antigen presenting cells; (c) induces production of proinflammatory cytokines by antigen presenting cells; (d) induces production of Th1-type cytokines by T cells; (e) elicits MHC Class I and/or MHC Class II, antigen-specific immune responses. Exemplary proinflammatory cytokines include, but are not limited to: interleukin-6 (IL-6), IL-12, IL-1 and tumor necrosis factor-$\alpha$ (TNF-$\alpha$). Th1 cytokines preferably include, but are not limited to, IL-2, IL-5, granulocyte macrophage-colony stimulating factor (GM-CSF) and interferon-γ (IFN-γ), and most preferably include IFN-γ.

Antigen presenting cells (APCs), including macrophages and dendritic cells, preferentially phagocytose damaged proteins and cells as well as bacteria, yeast and other substances that get into the body, because they express receptors that are collectively referred to as pattern recognition receptors (PRRs) that recognize pathogen associated molecular patterns (PAMPs). PAMPs represent organism-specific differences in glycosylation patterns, lipoproteins and nucleic acid composition. Hence, APCs have receptors for microbial mannoproteins, peptidoglycans, glucans, lipoproteins, double-stranded RNA and CpG island-containing DNA (Underhill, *Eur J Immunol* 2003; 33:1767-1775; Ozinsky et al., *Proc Natl Acad Sci USA* 2000; 97:13766-13771; Akira et al., *Nat Immunol* 2001; 2:675-680). Engagement of these receptors results in what has been termed a "danger" signal leading to dendritic cell maturation, activation, enhanced phagocytosis, and efficient presentation of antigens that were associated with the engaging material (Medzhitov and Janeway, *Science* 2002; 296:298-300). Examples of PRRs include Toll-like receptors (TLRs) (Kawai and Akira, *Cell Death Differ* 2006; 13:816-825).

While the present inventors have described the use of a yeast-based composition in the method of the present invention, other immunotherapeutic compositions having similar characteristics may also be used. In particular, any composition that includes one or more HCV antigens or immunogenic domains thereof in a formulation that, as a composition, elicits an HCV-specific, a T cell-mediated immune response (e.g., resulting in activation and expansion of HCV-specific CD4+ and/or CD8+ T cells), is expected to be useful in the present invention. More preferably, the composition will have the characteristics (a)-(e) listed above, or any subcombination thereof.

For example, in one aspect, the composition is formulated with an adjuvant that has such characteristics. In one aspect, the invention includes the use of a yeast-based immunotherapeutic composition comprising a yeast vehicle and an HCV antigen that is selected to elicit an immune response against HCV in an animal. Such compositions are described in more detail below, including in the Definitions section below.

The nucleic acid and amino acid sequence for HCV polyprotein genes and the polyproteins encoded thereby are known in the art. For example, the nucleic acid sequence of the polyprotein gene for Hepatitis C Virus strain 1177 is described in Database Accession No. AF011753 (gi: 2327074) and is represented herein by SEQ ID NO:19. SEQ ID NO:19 encodes the HCV strain H77 polyprotein, which has an amino acid sequence represented herein by SEQ ID NO:20. Within SEQ ID NO:20, the HCV proteins comprise the following positions: HCV Core (positions 1 to 191 of SEQ ID NO:20); HCV E1 envelope glycoprotein (positions 192 to 383 of SEQ ID NO:20); HCV E2 envelope glycoprotein (positions 384 to 746 of SEQ ID NO:20); HCV P7 ion channel (positions 747 to 809 of SEQ ID NO:20); HCV NS2 metalloprotease (positions 810 to 1026 of SEQ ID NO:20); HCV NS3 protease/helicase (positions 1027 to 1657 of SEQ ID NO:20); HCV NS4a NS3 protease cofactor (positions 1658 to 1711 of SEQ ID NO:20); HCV NS4b (positions 1712 to 1972 of SEQ ID NO:20); HCV NS5a (positions 1973 to 2420 of SEQ ID NO:20); and HCV NS5b RNA-dependent RNA polymerase (positions 2421 to 3011 of SEQ ID NO:20). Strains of HCV display high amino acid identity. Therefore, using the guidance provided herein and the reference to the exemplary HCV strain, one of skill in the art will readily be able to a variety of HCV-based proteins and peptides from any HCV strain for use in the compositions of the present invention.

One embodiment of the present invention relates to an immunotherapeutic composition comprising: (a) a yeast vehicle; and (b) at least one HCV antigen or immunogenic domain thereof expressed by, attached to, or mixed with the yeast vehicle. In some embodiments, the antigen is a fusion protein. In one aspect of the invention, fusion protein can include two or more antigens. In one aspect, the fusion protein can include two or more immunogenic domains or two or more epitopes of one or more antigens (e.g., NS3 and Core). Such a composition provides HCV-specific immunization in a broad range of patients, generating an immune response that will spread to other HCV epitopes. In one aspect, the immunotherapeutic composition is referred to as GI-5005, which is a whole, heat-killed *S. cerevisiae* immunotherapy product that recombinantly expresses high levels of immunogenic portions of HCV NS3 and Core antigens.

In one embodiment, fusion proteins that are used as a component of the yeast-based composition of the present invention are produced using constructs that are particularly useful for the expression of heterologous antigens in yeast or in some embodiments, attachment to the yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides significantly enhanced stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein). In addition, the present invention includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but is more preferably at least 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-$X_2$-$X_3$-$X_4$-$X_5$-$X_6$, wherein M is methionine; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine, lysine or arginine. In one embodiment, the $X_6$ residue is a proline. An exemplary synthetic sequence that enhances the stability of expression of an antigen in a yeast cell and/or prevents post-translational modification of the protein in the yeast includes the sequence M-A-D-E-A-P (SEQ ID NO:1). In addition to the enhanced stability of the expression product, this fusion partner does not appear to negatively impact the immune response against the vaccinating antigen in the construct. In addition, the synthetic fusion peptides can be designed to provide an epitope that can be recognized by a selection agent, such as an antibody.

In another embodiment of the invention, the nucleic acids that encode the translation start site of a synthetic peptide used in the invention are A-C-C-A-T-G-G, in accordance with Kozak translation sequence rules, where the ATG in this sequence is the initial translation start site and encodes the methionine of M-A-D-E-A-P (SEQ ID NO:1). It is to be understood that various embodiments of the invention as described herein may also be combined. For example, in one aspect of the invention, when the synthetic peptide is MA-D-E-A-P (SEQ ID NO:1), the nucleic acids encoding the start site for this peptide can be A-C-C-A-T-G-G. Various other combinations of embodiments of the invention will be apparent to those of skill in the art.

In one aspect of the invention, the yeast vehicle is manipulated such that the antigen is expressed or provided by delivery or translocation of an expressed antigen product, partially or wholly, on the surface of the yeast vehicle (extracellular expression). One method for accomplishing this aspect of the invention is to use a spacer arm for positioning one or more antigen(s) on the surface of the yeast vehicle. One way to use a spacer arm is to create a fusion protein of the antigen(s) of interest with a protein that targets the antigen(s) of interest to the yeast cell wall. For example, one protein that can be used is a yeast protein (e.g., cell wall protein 2 (cwp2), Aga2, Pir4 or Flo1 protein) that enables the antigen(s) to be targeted to the yeast cell wall such that the antigen is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) to be exposed on the yeast surface is to use signal sequences such as glycosylphosphatidyl inositol (GPI) to anchor the target to the yeast cell wall. Alternatively, positioning can be accomplished by appending signal sequences that target the antigen(s) of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length.

In another embodiment, the yeast protein stabilizes the expression of the fusion protein in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

In another aspect of the invention, other sequences can be used to target, retain and/or stabilize the protein to other parts of the yeast vehicle, for example, in the cytosol or the mitochondria. Examples of suitable yeast protein that can be used for any of the embodiments above include, but are not limited to, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

As discussed above, the compositions of the invention include at least one HCV antigen and/or at least one immunogenic domain of at least one HCV antigen for immunizing a subject. The composition can include, one, two, a few, several or a plurality of HCV antigens, including one or more immunogenic domains of one or more HCV antigens, as desired. For example, any protein, including any fusion protein, described herein can include at least one or more portions of any one or more HCV proteins selected from: HCV E1 envelope glycoprotein, HCV E2 envelope glycoprotein, HCV P7 ion channel, HCV NS2 metalloprotease, HCV NS3 protease/helicase, HCV NS4a NS3 protease cofactor, HCV NS4b, HCV NS5a, HCV NS5b RNA-dependent RNA polymerase, and HCV Core sequence. In one aspect, the fusion protein comprises at least one or more immunogenic domains of one or more HCV antigens.

In one preferred aspect of the invention, the HCV antigen is an HCV protein consisting of HCV NS3 protease and Core sequence. In another aspect, the HCV antigen consists of an HCV NS3 protein lacking the catalytic domain of the natural NS3 protein which is linked to HCV Core sequence. In another aspect, the HCV antigen consists of the 262 amino acids of HCV NS3 following the initial N-terminal 88 amino acids of the natural NS3 protein (i.e., positions 89-350 of HCV NS3; SEQ ID NO:20) linked to HCV Core sequence. In one aspect, the HCV Core sequence lacks the hydrophobic C-terminal sequence. In another aspect, the HCV Core sequence lacks the C-terminal two amino acids, glutamate and aspartate. In a preferred aspect, the HCV Core sequence consists of amino acid positions 2 through 140 of the natural HCV Core sequence.

In this embodiment, a yeast (e.g., *Saccharomyces cerevisiae*) was engineered to express a HCV NS3-Core fusion protein under the control of the copper-inducible promoter, CUP1. The fusion protein is a single polypeptide with the following sequence elements fused in frame from N- to C-terminus (HCV polyprotein (SEQ ID NO:20) numbering in parentheses, with the amino acid sequence of the fusion protein being represented herein by SEQ ID NO:2): 1) the sequence MADEAP (SEQ ID NO:9) to impart resistance to proteasomal degradation (positions 1 to 6 of SEQ ID NO:2); 2) amino acids 89 to 350 of (1115 to 1376 of SEQ ID NO:20) of the HCV NS3 protease protein (positions 6 to 268 of SEQ ID NO:2); 3) a single threonine amino acid residue introduced in cloning (position 269 of SEQ ID NO:2); 4) amino acids 2 to 140 (2 to 140 of SEQ ID NO:20) of the HCV Core protein (positions 270 to 408 of SEQ ID NO:2); and 5) the sequence E-D to increase the hydrophilicity of the Core variant (positions 409 to 410 of SEQ ID NO:2). A nucleic acid sequence encoding the fusion protein of SEQ ID NO:2 is represented herein by SEQ ID NO:1. SEQ ID NO:2 is the fusion protein expressed by the yeast-based immunotherapy product referred to herein as GI-5005.

In another preferred aspect of the invention, the HCV antigen is an inactivated full-length HCV NS3 that is part of a fusion protein according to the invention. In this embodiment, a yeast (e.g., *Saccharomyces cerevisiae*) was engineered to express an inactivated full-length HCV NS3 fusion protein under the control of the copper-inducible promoter, CUP1. The fusion protein comprising the full-length HCV NS3 is a single polypeptide with the following sequence elements fused in frame from N- to C-terminus (HCV polyprotein numbering in parentheses, with the amino acid sequence of the fusion protein being represented herein by SEQ ID NO:4): 1) the sequence MADEAP (SEQ ID NO:9) to impart resistance to proteasomal degradation (positions 1 to 6 of SEQ ID NO:4); and 2) amino acids 1 to 631 (1027 to 1657 of SEQ ID NO:20) of the HCV NS3 protease protein (positions 7 to 637 of SEQ ID NO:4) (note that the amino acid at HCV polypeptide residue 1165 has been changed from a serine to an alanine in order to inactivate the proteolytic activity). A nucleic acid sequence encoding the fusion protein of SEQ ID NO:4 is represented herein by SEQ ID NO:3.

In another preferred aspect of the invention, the yeast composition comprises a truncated HCV E1-E2 fusion protein. In this embodiment, a yeast (e.g., *Saccharomyces cerevisiae*) is engineered to express an E1-E2 fusion protein as a single polypeptide having the following sequence elements fused in frame from N- to C-terminus (HCV polyprotein numbering in parentheses, where the amino acid sequence of the fusion protein is represented herein by SEQ ID NO:6): 1) The sequence MADEAP (SEQ ID NO:9) to impart resistance to proteasomal degradation (positions 1 to 6 of SEQ ID NO:6); 2) amino acids 1 to 156 (192 to 347 of SEQ ID NO:20) of HCV protein E1 (positions 7 to 162 of SEQ ID NO:6); and 3) amino acids 1 to 334 (384 to 717 of SEQ ID NO:20) of HCV protein E2 (positions 163 to 446 of SEQ ID NO:6). It is noted that in this particular fusion protein, 36 C-terminal hydrophobic amino acids of E1 and 29 C-terminal hydrophobic amino acids of E2 were omitted from the fusion protein to promote cytoplasmic accumulation in yeast. A nucleic acid sequence encoding the fusion protein of SEQ ID NO:6 is represented herein by SEQ ID NO:5.

In yet another preferred aspect of the invention, the yeast composition comprises a transmembrane (TM) domain-deleted HCV NS4b fusion protein. The fusion protein is a single polypeptide with the following sequence elements arranged in tandem, in frame, from N- to C-terminus (polyprotein numbering in parentheses, with the amino acid sequence of the fusion protein being represented herein by SEQ ID NO:8): 1) The sequence MADEAP (SEQ ID NO:9) to impart resistance to proteosomal degradation (positions 1 to 6 of SEQ ID NO:8); 2) amino acids 1 to 69 (1712 to 1780 of SEQ ID NO:20) of HCV protein NS4b (positions 7 to 75 of SEQ ID NO:8); and 3) amino acids 177 to 261 (1888 to 1972 of SEQ ID NO:20) of HCV protein NS4b (positions 76 to 160 of SEQ ID NO:8). A 107 amino acid region corresponding to NS4b amino acids 70 to 176 (1781 to 1887 of SEQ ID NO:20) that contains multiple membrane spanning domains was omitted to promote cytoplasmic accumulation in yeast. A nucleic acid sequence encoding the fusion protein of SEQ ID NO:8 is represented herein by SEQ ID NO:7.

In yet another preferred aspect of the invention, the yeast composition comprises a Core-E1-E2 fusion protein. The fusion protein is a single polypeptide with the following sequence elements arranged in tandem, in frame, from N- to C-terminus (polyprotein numbering in parentheses, with the amino acid sequence of the fusion protein being represented herein by SEQ ID NO:12): 1) The sequence MADEAP (SEQ ID NO:9) to impart resistance to proteosomal degradation (positions 1-6 of SEQ ID NO:12); and 2) amino acids 1 to 746 (2 to 746 of SEQ ID NO:20) of unmodified HCV polyprotein encoding full-length Core, E1, and E2 proteins (positions 7 to 751 of SEQ ID NO:12: Core spanning from position 7 to 196; E1 spanning from positions 197 to 387; and E2 spanning from positions 388 to 751). A nucleic acid sequence encoding the fusion protein of SEQ ID NO:12 is represented herein by SEQ ID NO:11.

In another preferred aspect of the invention, the yeast composition comprises a Core-E1-E2 fusion protein with transmembrane domains deleted. The fusion protein is a single polypeptide with the following sequence elements fused in frame from N- to C-terminus (polyprotein numbering in parentheses, with the amino acid sequence of the fusion protein being represented herein by SEQ ID NO:14): 1) The sequence MADEAP (SEQ ID NO:9) to impart resistance to proteasomal degradation, 2) amino acids 2 to 140 (2 to 140 of SEQ ID NO:20) of HCV Core protein (positions 7 to 145 of SEQ ID NO:14), 3) amino acids 1 to 156 (192 to 347 of SEQ ID NO:20) of HCV protein E1 (positions 146 to 301 of SEQ ID NO:14), and 4) amino acids 1 to 334 (384 to 717 of SEQ ID NO:20) of HCV protein E2 (positions 302 to 635 of SEQ ID NO:14). The 51 C-terminal hydrophobic amino acids of Core protein, the 36 C-terminal hydrophobic amino acids of E1 and the 29 C-terminal hydrophobic amino acids of E2 were omitted from the fusion protein to promote cytoplasmic accumulation in yeast. A nucleic acid sequence encoding the fusion protein of SEQ ID NO:14 is represented herein by SEQ ID NO:13.

In yet another preferred aspect of the invention, the yeast composition comprises an NS3-NS4a-NS4b fusion protein wherein the NS3 protease is inactivated and the NS4b lacks a transmembrane domain. The NS3-NS4a-NS4b fusion protein is a single polypeptide with the following sequence elements fused in frame from N- to C-terminus (polyprotein numbering in parentheses, with the amino acid sequence of the fusion protein being represented herein by SEQ ID NO:16): 1) The sequence MADEAP (SEQ ID NO:9) to impart resistance to proteasomal degradation (positions 1 to 6 of SEQ ID NO:16); 2) amino acids 1 to 631 (1027 to 1657 of SEQ ID NO:20) corresponding to full-length HCV NS3 protein (note: Serine 139 (position 1165, with respect to SEQ ID NO:20) is changed to alanine to inactivate the proteolytic potential of NS3) (positions 7 to 634 of SEQ ID NO:16); 3) amino acids 1 to 54 (1658 to 1711 of SEQ ID NO:20) of NS4a protein (positions 635 to 691 of SEQ ID NO:16); 4) amino acids 1 to 69 (1712 to 1780 of SEQ ID NO:20) of HCV protein NS4b (positions 692 to 776 of SEQ ID NO:16); and 5) amino acids 177 to 261 (1888 to 1972 of SEQ ID NO:20) of HCV protein NS4b (positions 777 to 845 of SEQ ID NO:16). A 107 amino acid region corresponding to NS4b amino acids 70 to 176 (1781 to 1887 of SEQ ID NO:20) that contains multiple membrane spanning domains was omitted to promote cytoplasmic accumulation in yeast. A nucleic acid sequence encoding the fusion protein of SEQ ID NO:16 is represented herein by SEQ ID NO:15.

In another preferred aspect of the invention, the yeast composition comprises a NS5a-NS5b fusion protein with an inactivating deletion of NS5b C-terminus. This NS5a-NS5b fusion protein is a single polypeptide with the following sequence elements fused in frame from N- to C-terminus (polyprotein numbering in parentheses, with the amino acid sequence of the fusion protein being represented herein by SEQ ID NO:18): 1) The sequence MADEAP (SEQ ID NO:9) to impart resistance to proteasomal degradation (positions 1 to 6 of SEQ ID NO:18); 2) the entirety of NS5a protein corresponding to amino acids 1 to 448 (1973 to 2420 of SEQ ID NO:20) (positions 7 to 454 of SEQ ID NO:18); and 3) amino acids 1 to 539 (2421 to 2959 of SEQ ID NO:20) of NS5b (positions 455 to 993 of SEQ ID NO:18). The 52 C-terminal residues that are required for the activity of NS5b in HCV replication were deleted to inactivate the protein. A nucleic acid sequence encoding the fusion protein of SEQ ID NO:18 is represented herein by SEQ ID NO:17.

In a particular aspect of the invention, the above-described fusion proteins contain one or more heterologous linker sequences between two HCV proteins (e.g., the HCV NS3 sequence and the HCV Core sequence). In a preferred embodiment, the heterologous linker sequence consists of a single heterologous amino acid residue. In a more preferred embodiment, the heterologous linker sequence consists of a single threonine residue.

In any of the above-described compositions of the present invention, the following aspects related to the yeast vehicle are included in the invention. In one embodiment, yeast vehicle is selected from the group consisting of a whole yeast, a yeast spheroplast, a yeast cytoplast, a yeast ghost, a subcellular yeast membrane extract or fraction thereof, or any other yeast particle, including yeast in which a portion of the cell wall or cell wall proteins is removed, and including yeast in which the cytoplasm is removed. In one aspect, a yeast cell or yeast spheroplast used to prepare the yeast vehicle was transformed with a recombinant nucleic acid molecule encoding the antigen(s) such that the antigen is recombinantly expressed by the yeast cell or yeast spheroplast. In this aspect, the yeast cell or yeast spheroplast that recombinantly expresses the antigen(s) is used to produce a yeast vehicle comprising a yeast cytoplast, a yeast ghost, or a subcellular yeast membrane extract or fraction thereof. In one aspect, the yeast vehicle is from a non-pathogenic yeast. In another aspect, the yeast vehicle is from a yeast selected from the group consisting of: *Saccharomyces, Schizosaccharomyces, Kluveromyces, Hansenula, Candida* and *Pichia*. In one aspect, the *Saccharomyces* is *S. cerevisiae*.

In general, the yeast vehicle and antigen can be associated by any technique described herein. In one aspect, the yeast vehicle was loaded intracellularly with the HCV antigen. In another aspect, the HCV antigen was covalently or non-covalently attached to the yeast vehicle (i.e., expression is not required in this embodiment). In yet another aspect, the yeast vehicle and the HCV antigen were associated by mixing. In another aspect, the antigen is expressed recombinantly by the yeast vehicle or by the yeast cell or yeast spheroplast from which the yeast vehicle was derived.

More specifically, according to the present invention, a yeast vehicle is any yeast cell (e.g., a whole or intact cell) or a derivative thereof (see below) that can be used in conjunction with an antigen in a composition or therapeutic composition of the invention, or as an adjuvant. The yeast vehicle can therefore include, but is not limited to, a live intact yeast microorganism (i.e., a yeast cell having all its components including a cell wall), a killed (dead) or inactivated (e.g., by heat, exposure to a base, boiling, etc.) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a subcellular yeast membrane extract or fraction thereof (also referred to previously as a subcellular yeast particle).

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety. Yeast cytoplasts are typically produced by enucleation of yeast cells. Such a method is described, for example, in Coon, 1978, *Natl. Cancer Inst. Monogr.* 48, 45-55 incorporated herein by reference in its entirety. Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety. A subcellular yeast membrane extract or fraction thereof refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane extracts that contain yeast membrane portions and, when the antigen was expressed recombinantly by the yeast prior to preparation of the yeast membrane extract, the antigen of interest.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof can be used in accordance with the present invention, nonpathogenic yeast strains are preferred. Preferred genera of yeast strains include *Saccharomyces, Candida* (which can be pathogenic), *Cryptococcus, Hansenula, Kluyveromyces, Pichia, Rhodotorula, Schizosaccharomyces* and *Yarrowia*, with *Saccharomyces,*

*Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. More preferred yeast species include *S. cerevisiae, C. albicans*, H polymorpha, *P. pastoris* and *S. pombe. S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain.

In one embodiment, a preferred yeast vehicle of the present invention is capable of fusing with the cell type to which the yeast vehicle and antigen is being delivered, such as a dendritic cell or macrophage, thereby effecting particularly efficient delivery of the yeast vehicle, and in many embodiments, the antigen(s), to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. Yeast vehicles of the present invention are readily taken up by dendritic cells (as well as other cells, such as macrophages).

Yeast vehicles can be formulated into compositions of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, prior to loading into a dendritic cell, or other type of administration with an antigen, yeast vehicles can also be mixed with a pharmaceutically acceptable excipient, such as an isotonic buffer that is tolerated by the host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment (covalent or non-covalent) of the antigen to the yeast, and mixing of the yeast and antigen together, such as in a buffer or other solution or formulation. These types of complexes are described in detail below.

In one embodiment, a yeast cell used to prepare the yeast vehicle is transformed with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed (inactivated), or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen. Subsequently, the yeast vehicle, which now contains the antigen intracellularly, can be administered to the patient or loaded into a carrier such as a dendritic cell (described below). As used herein, a peptide comprises an amino acid sequence of less than or equal to about 30-50 amino acids, while a protein comprises an amino acid sequence of more than about 30-50 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically;

such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism, by the loading of a mammalian tumor cell, or portions thereof, for example.

In another embodiment of the present invention, an antigen is physically attached to the yeast vehicle. Physical attachment of the antigen to the yeast vehicle can be accomplished by any method suitable in the art, including covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen is expressed on or physically attached to the surface of the yeast, spacer arms may be carefully selected to optimize antigen expression or content on the surface. The size of the spacer arm(s) can affect how much of the antigen is exposed for binding on the surface of the yeast. Thus, depending on which antigen(s) are being used, one of skill in the art will select a spacer arm that effectuates appropriate spacing for the antigen on the yeast surface. In one embodiment, the spacer arm is a yeast protein of at least 450 amino acids. Spacer arms have been discussed in detail above.

Another consideration for optimizing antigen surface expression is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

One of skill in the art can optimize the performance of the yeast vehicle (with and without heterologous antigen expression), both on the surface of the yeast vehicle and in the cytosol, by growing the yeast cells at a pH level which is higher than 5.5 (i.e., neutral pH). The use of neutral pH helps to optimize the antigen accessibility and surface presentation, allows the yeast cell wall to be in a more pliable state, and trigger the immune cells binding the yeast to generate an optimized immune response including secreting beneficial cytokines (e.g., INF-gamma) and optimized activation responses.

Another method that one of skill in the art can use to optimize the placement and/or expression of antigen on yeast vehicles is to control the amount of yeast glycosylation. The amount of yeast glycosylation can affects the immunogenicity and antigenicity of the antigen expressed on the surface, since sugar moieties tend to be bulky. As such, the existence of sugar moieties on the surface of yeast and its impact on the three-dimensional space around the target antigen(s) should be considered. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g. *Pichia*. One can also treat the yeast using methods that reduce or alter the glycosylation.

Another consideration with respect to the provision of antigen on the surface of a yeast is how the yeast is inactivated and its potential effects on how this affects the antigenicity of the antigen expressed on the surface. Heat inactivation of yeast is a standard way of inactivating yeast, and one of skill in the art can monitor the structural changes of the target antigen by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the optimization strategies used should take the secondary, tertiary or quaternary structure of the target antigen into consideration and preserve such structure as to optimize its immunogenicity.

In yet another embodiment, the yeast vehicle and the antigen are associated with each other by a more passive, non-specific or non-covalent binding mechanism, such as by gently mixing the yeast vehicle and the antigen together in a buffer or other suitable formulation. Yet another embodiment of the present invention relates to a nucleic acid-based composition, such as a DNA composition or viral vector composition, comprising a nucleic acid construct (e.g., a viral vector or other recombinant nucleic acid molecule) encoding an HCV fusion protein as described herein (with or without the various N- and C-terminal modifications described herein). The composition can further include any pharmaceutically acceptable delivery vehicle (which can include a pharmaceutically acceptable excipient or adjuvant), and the composition as a whole should have the characteristic of being able to elicit an MHC Class I cellular immune response against HCV.

Another embodiment of the present invention relates to a pseudovirion which is composed of various HCV fusion proteins of the invention.

In one embodiment of the present invention, a composition can also include biological response modifier compounds, or the ability to produce such modifiers (i.e., by transfection with nucleic acid molecules encoding such modifiers). Such modifiers can be the element of the composition that provides one or more of the characteristics of an immunotherapeutic composition of the invention. Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma), interferon alpha (IFN-alpha), insulinlike growth factor I (IGF-I), transforming growth factor beta (TGF-β), steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity Other suitable biological response modifiers include, but are not limited to, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®), anti-CD4, anti-CD25, anti-PD-1, anti-PD-L1, anti-PD-L2 or agents that block FOXP3 (e.g., to abrogate the activity/kill CD4+/CD25+ T regulatory cells); Flt3 ligand, imiquimod (Aldara™), GM-CSF, sargramostim (Leukine®), Toll-like receptor (TLR)-7 agonists, or TLR-9 agonists (e.g., agents that increase the number of, or increase the activation state, of dendritic cells, macrophages and other professional antigen-presenting cells). Such biological response modifiers are well known in the art and are publicly available.

An adjuvant can also be considered to be a biological response modifier. According to the present invention, adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). As discussed above, preferred adjuvants induce a Th1-type immune response and preferably, a T cell-mediated immune response (CD4+ and/or CD8+).

Compositions and therapeutic compositions of the invention can further include any other compounds that are useful for protecting a subject from HCV infection or that treats or ameliorates any symptom of such an infection.

As used herein, a pharmaceutically acceptable carrier refers to any substance or vehicle suitable for delivering an HCV fusion protein useful in a method of the present invention to a suitable in vivo or ex vivo site. Such a carrier can include, but is not limited to, an adjuvant, an excipient, or any other type of delivery vehicle or carrier.

Carriers are typically compounds that increase the half-life of a therapeutic composition in the treated animal. Suitable carriers include, but are not limited to, polymeric controlled release formulations, biodegradable implants, liposomes, oils, esters, and glycols.

Therapeutic compositions of the present invention can also contain one or more pharmaceutically acceptable excipients. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a composition (or a yeast vehicle or dendritic cell comprising the yeast vehicle) in a form that, upon arrival of the composition at a target cell, tissue, or site in the body, the composition is capable of eliciting an immune response at the target site (noting that the target site can be systemic). Suitable excipients of the present invention include excipients or formularies that transport, but do not specifically target the composition to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

The immunotherapeutic composition preferably elicits an immune response in a subject such that the subject obtains a benefit from the composition and is preferably treated. As used herein, the phrase "treated" with respect to HCV infection refers to reducing one or more symptoms of the disease; reducing the occurrence of the disease, and/or reducing the severity of the disease. In particular, the immunotherapeutic composition can provide one or more benefits to a subject that is infected with HCV, including, but not limited to, elicitation of cellular immune responses against HCV (including MHC Class I and/or MHC Class II responses, and preferably, CD4+ and/or CD8+ T cell responses), reduction in viral load, achievement of Rapid Virologic Response (RVR), achievement of Enhanced Virologic Response (EVR), achievement of complete Enhanced Virologic Response (cEVR), achievement of Sustained Virologic Response (SVR), improvement of liver function, reduction of liver inflammation, normalization of alanine aminotransferase (ALT) levels, and/or reduced liver damage. The term, "disease" refers to any deviation from the normal health of an animal and includes a state when disease symptoms are present, as well as conditions in which a deviation (e.g., infection, gene mutation, genetic defect, etc.) has occurred, but symptoms are not yet manifested.

The present invention includes the delivery of a composition of the invention to an animal. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle and antigen are loaded into the cell, and returning the cells to the patient. The therapeutic composition of the present invention can be returned to a patient, or administered to a patient, by any suitable mode of administration.

Administration of a composition of the invention can be systemic, mucosal and/or proximal to the location of the target site. The preferred routes of administration will be apparent to those of skill in the art. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

In accordance with the present invention, a suitable single dose size is a dose that is capable of eliciting an antigen-specific immune response in an animal when administered one or more times over a suitable time period. Doses can vary depending upon the disease or condition being treated. For example, in one embodiment, a single dose of a yeast vehicle of the present invention is from about $1\times10^5$ to about $5\times10^7$ yeast cell equivalents per kilogram body weight of the organism being administered the composition. In a preferred embodiment, the yeast cells per dose are not adjusted for weight of the organism. In this embodiment, a single dose of a yeast vehicle of the present invention is from about $1\times10^4$ to about $1\times10^9$ yeast cells per dose. More preferably, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). This range of doses can be effectively used in any organism of any size, including mice, monkeys, humans, etc.

"Boosters" or "boosts" of a therapeutic composition are preferably administered when the immune response against the antigen has waned or as needed to provide an immune response or induce a memory response against a particular antigen or antigen(s). Boosters can be administered from about 1 or 2 weeks to monthly to annually to several years after the original administration. In one embodiment, an administration schedule is one in which from about $1\times10^5$ to about $5\times10^7$ yeast cell equivalents of a composition per kg body weight of the organism is administered from about one to about 4 times over a time period of from about 1 month to about 6 months.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, goats, sheep, cattle, horses and pigs, with humans being particularly preferred. According to the present invention, the term "patient" or "subject" can be used to describe any animal that is the subject of a diagnostic, prophylactic, or therapeutic treatment as described herein.

DEFINITIONS

"Standard Of Care (SOC)" refers to the current standard of care for the treatment of hepatitis C virus, which consists essentially of the administration of a combination of interferon (preferably interferon-α2, and more preferably, pegylated interferon-α) with the anti-viral compound, ribavirin. The combination is typically administered by subcutaneous injection of interferon once weekly for 24 weeks (HCV genotypes 2 and 3) or 48 weeks (HCV genotypes 1 and 4), with concurrent administration of ribavirin, typically administered orally on a daily dosing schedule.

"Viral negativity" or "complete response", which terms may be capitalized, can be used interchangeably herein and are defined as HCV RNA<25 IU/ml, which includes undetectable virus. A "complete responder" is a subject who has achieved a complete response.

"Rapid Virologic Response (RVR)" is defined as viral negativity after 4 weeks of interferon-based therapy.

"Early Virologic Response (EVR)" is defined as >2 log 10 reduction in viral load by week 12 of interferon-based therapy.

"Complete EVR (cEVR)" is defined as viral negativity by week 12 of interferon-based therapy.

"End of Treatment Response (ETR)" is defined as viral negativity by 48 weeks of interferon-based therapy (for genotype 1 patients).

"Sustained Virologic Response (SVR or SVR24)" is defined as viral negativity at 6 months post ETR.

"Naïve" or "Interferon-naïve" subjects (patients) are subjects who have not been previously treated with interferon or SOC (interferon plus ribavirin).

"Null Responders" are HCV infected subjects that cannot achieve at least a 1 log 10 reduction in viral load by week 12 on SOC.

"Non-Responders" are subjects who receive a 12-week course of therapy and fail to achieve EVR.

"Partial Responders" are defined as subjects who have >2 log 10 viral load reduction by 12 weeks, but never achieve viral negativity.

"Breakthrough" subjects are subjects who achieve viral negativity during treatment, but whose viral loads return to detectable levels before end of treatment (ETR endpoint).

"Relapsers" are subjects who achieve viral eradication (negativity) by end of treatment (ETR endpoint), but whose viral load returns to detectable levels during the 24 week follow up.

As used herein, the term "interferon" refers to a cytokine that is typically produced by cells of the immune system and by a wide variety of cells in response to the presence of double-stranded RNA. Interferons assist the immune response by inhibiting viral replication within host cells, activating natural killer cells and macrophages, increasing antigen presentation to lymphocytes, and inducing the resistance of host cells to viral infection. Type I interferons include interferon-α. Interferons useful in the methods of the present invention include any type I interferon, and preferably interferon-α, and more preferably, interferon-α2, and more preferably, longer lasting forms of interferon, including, but not limited to, pegylated interferons, interferon fusion proteins (interferon fused to albumin), and controlled-release formulations comprising interferon (e.g., interferon in microspheres or interferon with polyaminoacid nanoparticles). One interferon, PEGASYS®, peginterferon alfa-2a, is a covalent conjugate of recombinant alfa-2a interferon (approximate molecular weight [MW] 20,000 daltons) with a single branched bis-monomethoxy polyethylene glycol (PEG) chain (approximate MW 40,000 daltons). The PEG moiety is linked at a single site to the interferon alfa moiety via a stable amide bond to lysine. Peginterferon alfa-2a has an approximate molecular weight of 60,000 daltons. Interferon alfa-2a is produced using recombinant DNA technology in which a cloned human leukocyte interferon gene is inserted into and expressed in *Escherichia coli.*

As used herein, the term "anti-viral compound" refers to any compound, typically a small-molecule inhibitor or antibody, that targets one or more various steps in the HCV life cycle with direct antiviral therapeutic effects. Anti-viral compounds for HCV treatment are sometimes called "Specifically Targeted Antiviral Therapy for Hepatitis C" or "STAT-C". Examples of anti-viral compounds include, but are not limited to, viral protease inhibitors (e.g., TELAPREVIR™, an NS3 protease inhibitor from Vertex/Johnson & Johnson/Mitsubishi; BOCEPREVIR™, an NS3 protease inhibitor from Schering-Plough), polymerase inhibitors (e.g., R-1728, an NS5b polymerase inhibitor from Roche/Pharmasset), or other viral inhibitors (e.g., TARIBAVIRIN™ (viramidine) from Valeant). Ribavirin is a preferred anti-viral compound. The term "anti-viral compound" as used herein also includes host enzyme inhibitors.

"Host Enzyme Inhibitors" act indirectly, as they target neither the virus nor the immune system. These molecules work by inhibiting a host cell function exploited by a virus. Examples of such inhibitors include, but are not limited to, cyclophilin B inhibitors, alpha glucosidase inhibitors, PFOR inhibitors, and IRES inhibitors. Exemplary host enzyme inhibitors include, but are not limited to, DEBIO-025™ (Debiopharma), a cyclophilin B inhibitor; CELGOSIVIR™ (Migenix), an oral alpha glucosidase inhibitor; NIM811™ (Novartis), a cyclophilin B inhibitor; ALINIA™ (nitazoxanide, by Romark), a PFOR inhibitor; and VGX-410C™ (VGX Pharma), an oral IRES inhibitor.

"Ribavirin" is an ribosyl purine analogue with an incomplete purine 6-membered ring. The chemical name of ribavirin is 1-(beta)-D-ribofuranosyl-1H-1,2,4-triazole-3-carboxamide. The empirical formula of ribavirin is $C_8H_{12}N_4O_5$ and the molecular weight is 244.2. Ribavirin is a white to off-white powder. It is freely soluble in water and slightly soluble in anhydrous alcohol. Ribavirin's carboxamide group can make the native nucleoside drug resemble adenosine or guanosine, depending on its rotation. Ribavirin is a prodrug that is activated by cellular kinases, which change it into the 5' triphosphate nucleotide. In this form, it interferes with aspects of RNA metabolism related to viral replication. Derivatives of ribavirin are well-known in the art and are marketed as (COPEGUS™; REBETOL™; RIBASPHERE™; VILONA™, VIRAZOLE™, also generics from Sandoz, Teva, Warrick).

An "immunotherapeutic composition" is a composition that elicits an immune response sufficient to achieve at least one therapeutic benefit in a subject.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound has at least one detectable activity that has an effect on the metabolic or other processes of a cell or organism, as measured or observed in vivo (i.e., in a natural physiological environment) or in vitro (i.e., under laboratory conditions).

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens can include carbohydrates, which can be loaded into a yeast vehicle or into a composition of the invention. It will be appreciated that in some embodiments (i.e., when the antigen is expressed by the yeast vehicle from a recombinant nucleic acid molecule), the antigen is a protein, fusion protein, chimeric protein, or fragment thereof, rather than an entire cell or microorganism.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An epitope is defined herein as a single immunogenic site within a given antigen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions).

An "individual" or a "subject" or a "patient", which terms may be used interchangeably, is a vertebrate, preferably a mammal, more preferably a human. Mammals include, but are not limited to, farm animals, sport animals, pets, primates, mice and rats.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived.

According to the present invention, reference to a "heterologous" protein or "heterologous" antigen, including a heterologous fusion protein, in connection with a yeast vehicle of the invention means that the protein or antigen is not a protein or antigen that is naturally expressed by the yeast, although a fusion protein may include yeast sequences or proteins or portions thereof that are naturally expressed by yeast.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. As discussed above, according to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

Reference to an isolated protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the results of a phase 1b clinical trial of human subjects treated using immunotherapy as a monotherapy.

In a completed phase Ib clinical trial of GI-5005 monotherapy in human subjects, administration of GI-5005 resulted in dose dependent biochemical (ALT) normalization, decreases in viral load up to 1.4 $log_{10}$, and induction of HCV-specific T cell responses, including both HCV NS3- and HCV Core-specific T cell responses. Importantly, none of these results were observed in the placebo controls. The phase 1b trial was a randomized, double-blind, placebo-controlled, multi-center, dose cohort-escalation, therapeutic trial evaluating the subcutaneous administration of 7 doses of GI-5005 monotherapy compared to placebo dosing in human subjects. The enrolled subjects had chronic HCV infection with high circulating virus levels and were either treatment naïve, or partial responders or relapsers to an interferon-based regimen (pegylated or non-pegylated interferon-α with or without ribavirin). GI-5005 was delivered subcutaneously weekly for 5 doses, followed by 2 additional monthly doses. The initial dose of GI-5005 was 0.05 YU (Yeast Units: 1 YU=$10^7$ yeast cells) injected subcutaneously once per week for four consecutive weeks (5 immunization days) followed by two additional monthly doses. The subsequent dose groups were escalated to 0.5 YU, 2.5 YU, 10.0 YU, 20 YU and 40 YU (see Table 1 for dose levels and planned group sizes).

TABLE 1

| Dose Group | Number of Subjects (active:placebo) | GI-5005 Yeast Units (YU) |
|---|---|---|
| 1 | 6:2 | 0.05 |
| 2 | 6:2 | 0.5 |
| 3 | 6:2 | 2.5 |
| 4 | 12:4 | 10.0 |
| 5 | 12:4 | 20.0 |
| 6 | 12:4 | 40.0 |

Immunology assays (ELISpot) were performed at baseline and days 36 (post weekly dosing), 92 (post monthly dosing) and 225 (5 months post last dose). ELISpot measures the number of subject T cells activated in response to HCV antigens ex vivo. Viral load and alanine aminotransferase (ALT) levels were measured on every subject visit (baseline and days 8, 15, 22, 29, 36, 43, 57, 64, 71, 85, 92, 99, 169, 225, 336). ALT is a well-validated measure of hepatic injury and serves as a surrogate for hepatic inflammation. In prior large hepatitis trials, reductions and/or normalization of ALT levels have been shown to correlate with improved liver function and reduced liver fibrosis as determined by serial biopsy.

ELISpot Results

Of those people that become infected with hepatitis C virus, approximately 20% of individuals clear the virus without medical intervention (acute infection); the remaining 80% of individuals become chronically infected. More specifically, while acutely infected patients have a broad, HCV-specific T cell response, chronically infected patients are characterized by weak cellular immune responses, as well as attenuated and narrow immune responses to HCV epitopes. The inventors believed that administration of GI-5005 would convert HCV-specific immune responses in chronically infected individuals to resemble those immune responses that correlate with clearance of HCV infection without medical intervention.

An ELISpot assay was run on peripheral blood mononuclear cells (PBMCs) from subjects at select study visits. The PBMCs were mixed with HCV peptides ex vivo and analyzed for interferon-γ (IFNγ) production, a hallmark of antigen-specific T cell activation. Pools of non-optimized HCV peptides and pools of optimized HCV peptides were used for ex vivo stimulation of subject PBMCs. PBMCs were then harvested after ex vivo peptide stimulation and the number of cells (or "spots") per million PBMCs that produce IFNγ was measured using the enzyme-linked immunosorbant (ELISpot) assay.

The ELISpot results revealed a treatment-emergent HCV specific immune response in GI-5005 treated subjects, but not in placebo subjects. More particularly, treatment with GI-5005 can convert a subject with a weak ELISpot response to a broad and strong ELISpot response that is consistent with the type of response observed in acutely infected patients (data not shown). Of 39 treated subjects with sufficient blood sampling, 9 subjects (23%) met the definition of responder for the non-optimized peptide conditions and/or the optimized peptide conditions (data not shown). Importantly, none of the placebo subjects met these criteria for a positive immunologic response by the ELISpot assay.

Moreover, the responses in the GI-5005 treated subjects were from HCV-specific T cells, as the T cells from the responder subjects did not respond to any peptides in a peptide pool from human immunodeficiency virus (HIV) (data not shown).

Viral Load Results

Examination of viral load in the subjects from all cohorts revealed that 6 subjects (13%) had decreases in viral load ranging from −0.75 $log_{10}$ to −1.4 $log_{10}$ (data not shown). None of the placebo-treated subjects had near $log_{10}$ reductions.

ALT Normalization Results

Alanine aminotransferase (ALT) is an enzyme expressed in liver cells and is a well-validated measure of hepatic injury (i.e. rupture of liver cells by necrosis or damage releases ALT into the blood stream). A dose response for ALT normalization was observed in patients receiving GI-5005, reaching 50% in the 40 YU dose cohort, with normalization defined as at least 2 consecutive visits with ALT within normal limits in those patients with a baseline ALT greater than the upper limit of normal. None of the placebo-treated subjects normalized ALT values. These results demonstrated that GI-5005 immunization in chronic HCV-infected individuals improved liver function (reduced ongoing liver damage) for treated subjects. This parameter for improved outcome on treatment is significant in that chronic HCV-infected individuals commonly develop liver cancer or require liver transplant.

Summary

In summary, the results from the phase Ib trial of GI-5005 monotherapy showed that a short course of GI-5005 monotherapy is capable of generating an HCV-specific immune response that is associated with viral load reductions of up to 1.4 $log_{10}$, as well as ALT normalization (demonstrating reduction in ongoing liver damage). No placebo-treated subjects experienced any of these results. Accordingly, the composition demonstrated significant efficacy as in vivo monotherapy in human subjects, in the face of ongoing viral replication.

Example 2

The following example shows results from an interim analysis of a phase 2 clinical trial in humans, demonstrating that administration of an immunotherapeutic composition to patients chronically infected with HCV prior to combination therapy with interferon and ribavirin significantly improves the rapid viral response (RVR) in treatment naïve patients, and shows an advantage in prior non-responders and patients with high titer HCV RNA.

GI-5005 is a whole heat-killed *S. cerevisiae* immunotherapy expressing high levels of HCV NS3 and Core antigens. GI-5005 has been designed to elicit antigen-specific host CD4 and CD8 T-cell responses with the goal of improving the rate of immune clearance of HCV. The GI-5005-02 phase 2 study evaluates the efficacy and safety of GI-5005 plus peg-IFN/ribavirin (SOC) in subjects with genotype 1 chronic HCV infection.

Figure 1:
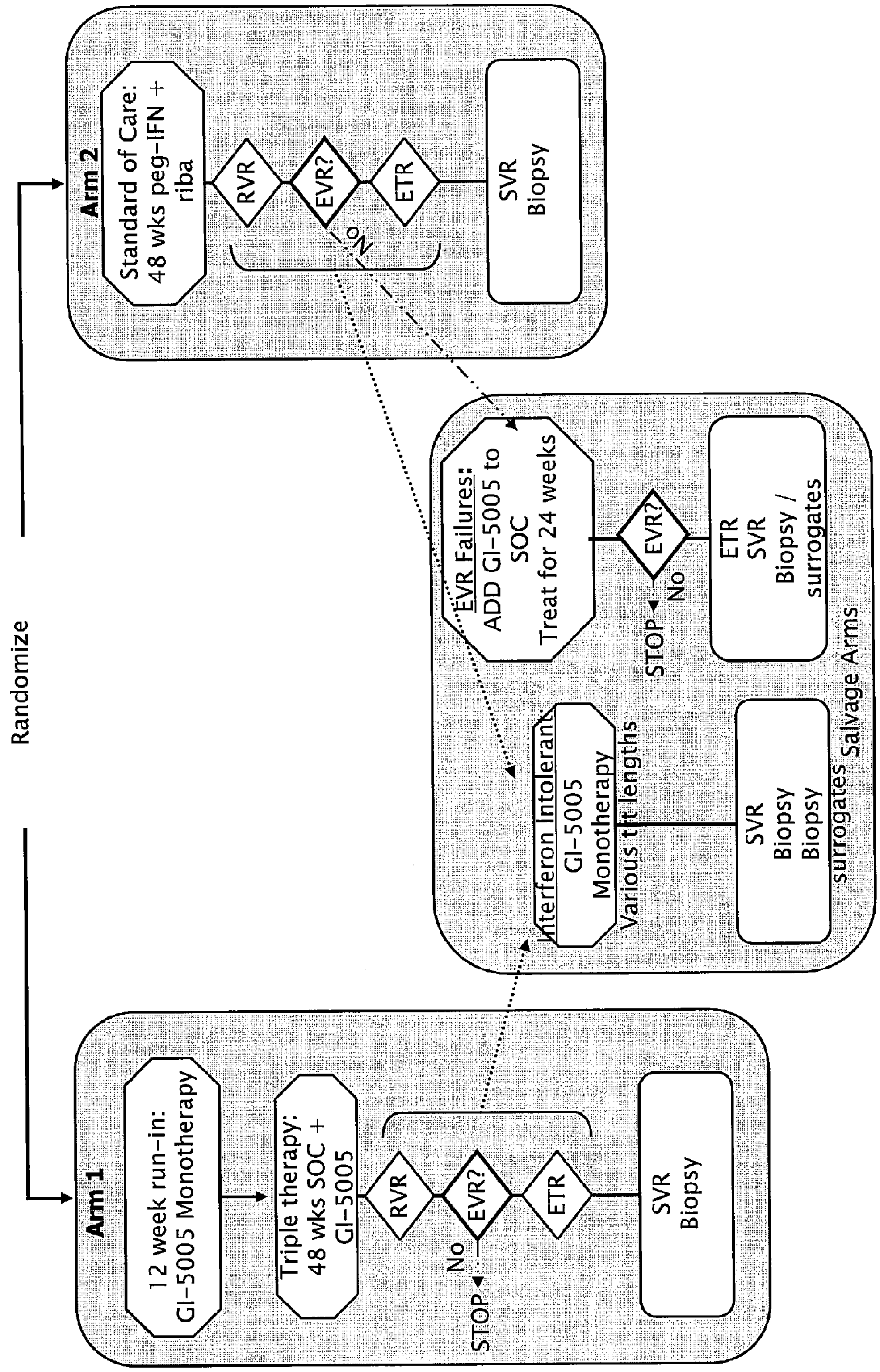

FIG. 1 shows the schematic design of the phase 2 study of GI-5005 in combination with SOC. Genotype 1 subjects with chronic HCV infection who were treatment naïve or non-responders to prior interferon (IFN) or peginterferon (pegIFN) based therapy were eligible (prior null responders and relapsers were excluded). Patients (140 total enrolled) were randomized 1:1, and stratified by virologic response during their prior course of treatment in this open label trial; Arm 1-GI5005 monotherapy run-in consisting of five weekly followed by 2 monthly subcutaneous (SC) doses of 40 YU (1 YU=10,000,000 yeast) GI-5005 over 12 weeks (administered as 10 YU doses to four separate sites on the patient), followed by triple therapy consisting of monthly 40 YU GI-5005 doses plus pegIFN/ribavirin (treatment period is 48 weeks in naïve patients, and 72 weeks in prior non-responders), Arm 2-treatment with SOC alone (without antecedent GI-5005 monotherapy).

PEGASYS®, peginterferon alfa-2a, is a covalent conjugate of recombinant alfa-2a interferon (approximate molecular weight [MW] 20,000 daltons) with a single branched bis-monomethoxy polyethylene glycol (PEG) chain (approximate MW 40,000 daltons). The PEG moiety is linked at a single site to the interferon alfa moiety via a stable amide bond to lysine. Peginterferon alfa-2a has an approximate molecular weight of 60,000 daltons. Interferon alfa-2a is produced using recombinant DNA technology in which a cloned human leukocyte interferon gene is inserted into and expressed in *Escherichia coli.*

The chemical name of ribavirin is 1-(beta)-D-ribofuranosyl-1H-1,2,4-triazole-3-carboxamide. The empirical formula of ribavirin is $C_8H_{12}N_4O_5$ and the molecular weight is 244.2. Ribavirin is a white to off-white powder. It is freely soluble in water and slightly soluble in anhydrous alcohol. Ribavirin is a synthetic nucleoside analogue. The mechanism by which the combination of ribavirin and an interferon product exerts its effects against the hepatitis C virus has not been fully established.

Ribavirin and interferon were administered according to the following recommended dosing information. The recommended dose of PEGASYS® when used in combination with ribavirin for chronic hepatitis C is 180 μg (1.0 mL vial or 0.5 mL prefilled syringe) once weekly. The daily dose of ribavirin is 1000 mg (subject<75 kg) to 1200 mg (subject≥75 kg) administered orally in two divided doses. The dose should be individualized to the patient depending on baseline weight and tolerability of the regimen).

The study was conducted in 40 centers in the United States, India and Europe. 74% of the total enrolled patients are naïve to prior interferon-based therapy; 26% are prior treatment failures.

Figure 2:
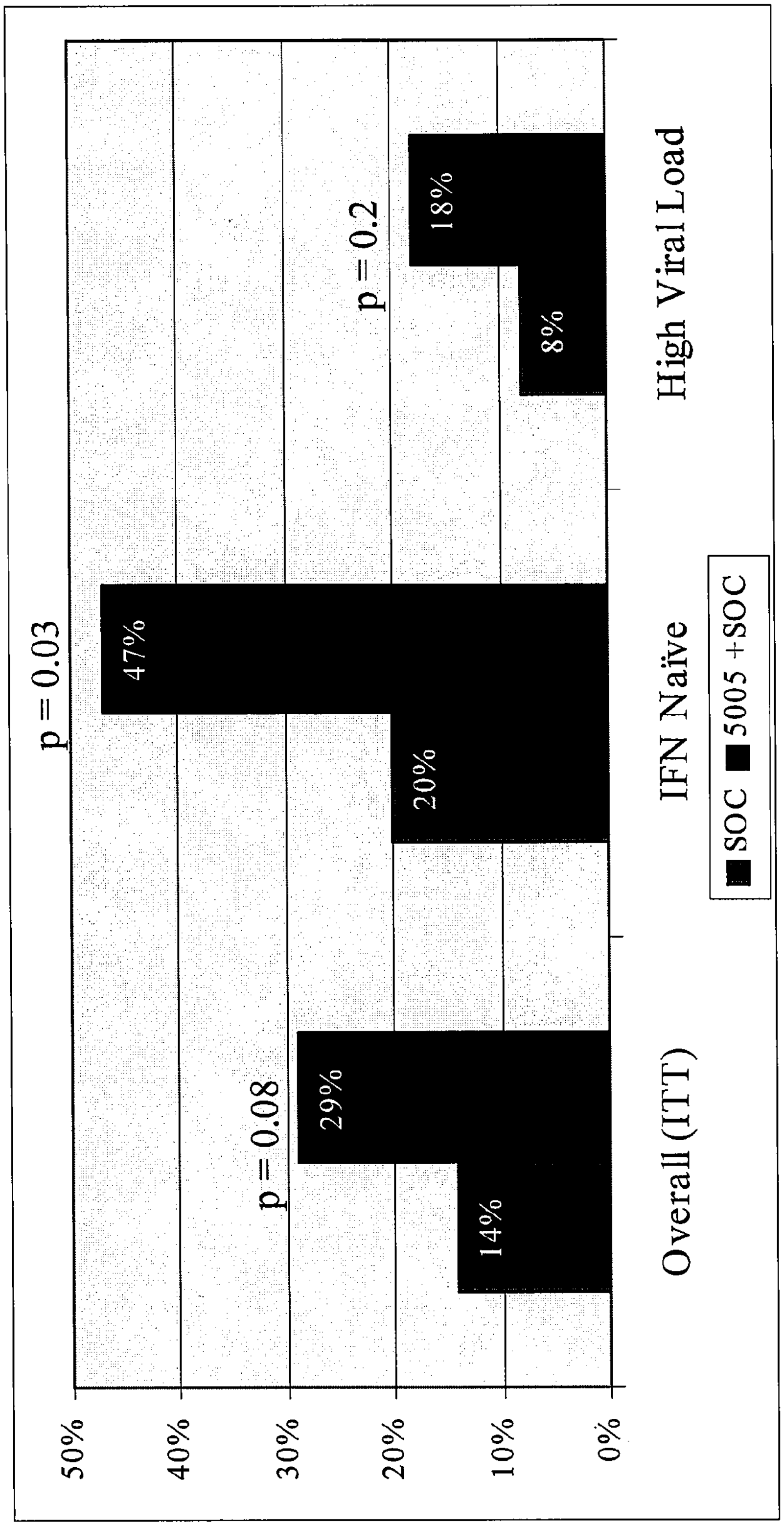
Figure 3:
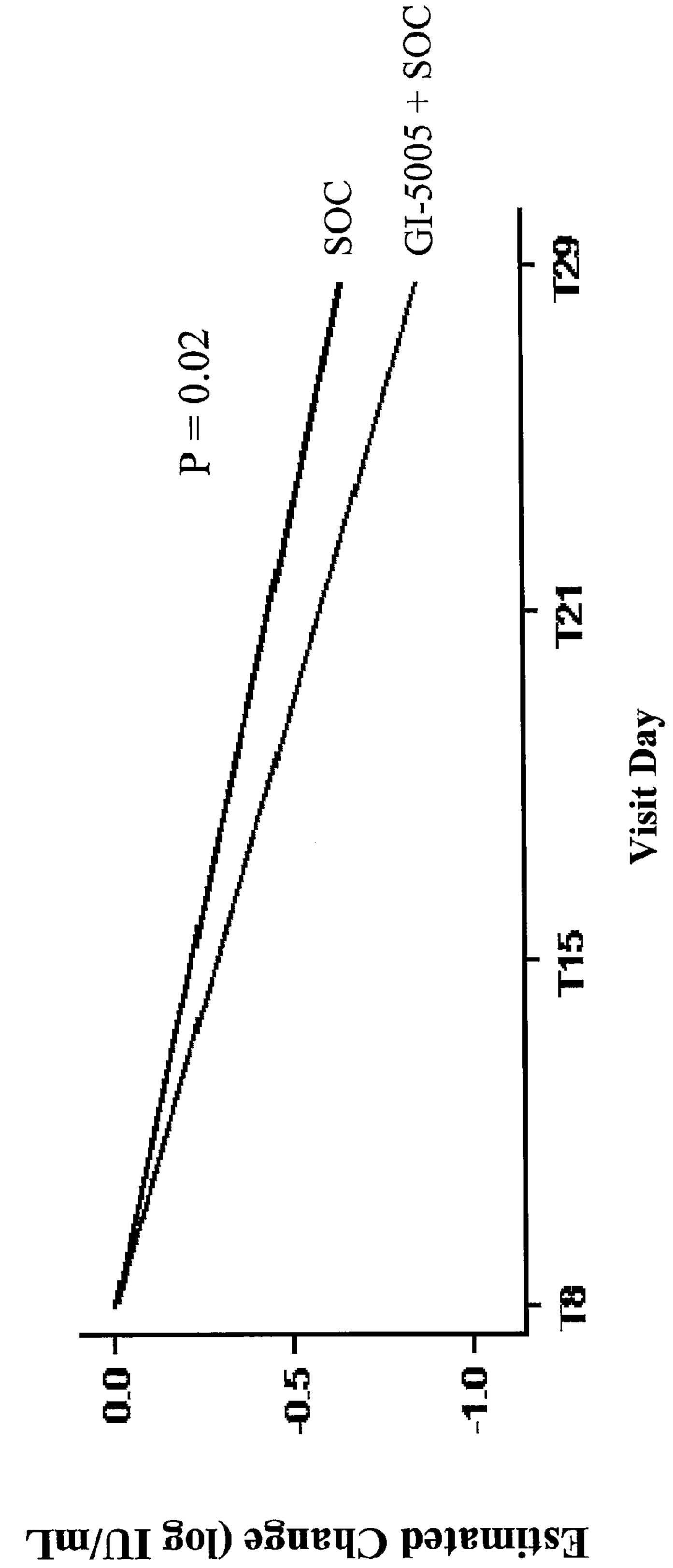

At the interim analysis, 28 of 72 patients (FIG. 1; Arm 1) had completed the first 4 weeks of triple therapy, with a trend to improved rapid virologic response (RVR defined as HCV RNA<25 IU/mL by week 4) in the triple therapy group; overall (8/28 {29%} vs 9/65 {14%}; p=0.08), naïve (8/17 {47%} vs 9/46 {20%}; p=0.03), and baseline HCV RNA>600,000 IU/mL (4/22 {18%} vs 5/60 {8%} p=0.19). 65/68 patients in Arm 2 had completed the first 4 weeks of SOC. FIG. 2 compares RVR rates. There were no RVR responses in prior non-responders in either treatment arm. Second phase viral kinetic slopes (Day 8-Day 29; see FIG. 3) showed an advantage for triple therapy compared to SOC in prior IFN non-responders (−1.16 log 10/mo. vs −0.88 log 10/mo; p=0.02), and patients with HCV RNA>600,000 IU/mL at baseline (−1.92 log 10/mo. vs −1.76 log 10/mo; p=0.36). Triple therapy was well-tolerated to the time of analysis, with no GI5005 related serious adverse events, dose limiting toxicities or discontinuations due to adverse events.

Accordingly, at this interim analysis the inventors have observed a statistically significant difference in RVR rate in treatment naïve patients (8/17 {47%} vs 9/46 {20%}; p=0.03) favoring triple therapy, supporting the belief that immune clearance is having an impact on an important early and predictive virologic endpoint. RVR has been shown to have strong positive predictive value for SVR (ranging from 90-100%) after completion of SOC (Poordad et al, Clin Inf Dis 2008, Jensen et al, Hepatology 2006, Yu et al, Hepatology 2008). While no patients with prior non-response to IFN-based therapy achieved an RVR in either treatment arm to date, the inventors have also observed a statistically significant difference in the kinetic rate of viral clearance between Day 8 and Day 29 for non-responders favoring triple therapy (−1.16 log 10/mo. vs −0.88 log 10/mo; p=0.02). If these kinetic differences are modeled forward through 12 weeks it projects a treatment effect of −0.80 log 10, and may predict better EVR (2 log 10 or better reduction) and potentially better complete EVR rates (negativity for HCV RNA) by week 12 for the triple therapy group.

Triple therapy with GI5005 plus pegIFN/ribavirin was well tolerated and has generated preliminary data indicating improved RVR rates compared to SOC in naïve patients with chronic genotype 1 HCV. Second phase viral clearance kinetics also indicates an early favorable effect of this strategy in prior IFN non-responders.

It is expected that improved immune clearance of HCV in chronically infected patients will improve clinical outcomes as measured by virologic endpoints. The significance of this approach is that the mechanism of enhanced immune clearance will be sustainable with continued boosting and will be complementary or synergistic with other treatment modalities that act primarily by inhibiting viral replication (IFN based therapy and small molecule inhibitors).

While the GI-5005-02 interim data assess early virologic endpoints, the inventors believe they represent important early treatment effects that support the inventors' belief that improved immune clearance of HCV in the context of full length SOC can have an important impact on clinical outcomes as measured by later virologic endpoints including EVR and SVR.

Example 3

The following example shows results from the complete four week virologic endpoint analysis of the phase 2 clinical trial of subjects treated with GI-5005 immunotherapy in combination with interferon/ribavirin therapy, demonstrating that administration of an immunotherapeutic composition to patients chronically infected with HCV prior to combination therapy with interferon and ribavirin results in a trend toward improvement of the rapid viral response (RVR), as well as continued improved second phase viral clearance kinetics, in all major patient subgroups.

This Example describes the analysis of all patients in both arms of the phase 2 clinical trial described in Example 2 after completion of four weeks of therapy with interferon/ribavirin. Results present the safety, viral kinetics, and RVR for the complete dataset.

Figure 4:
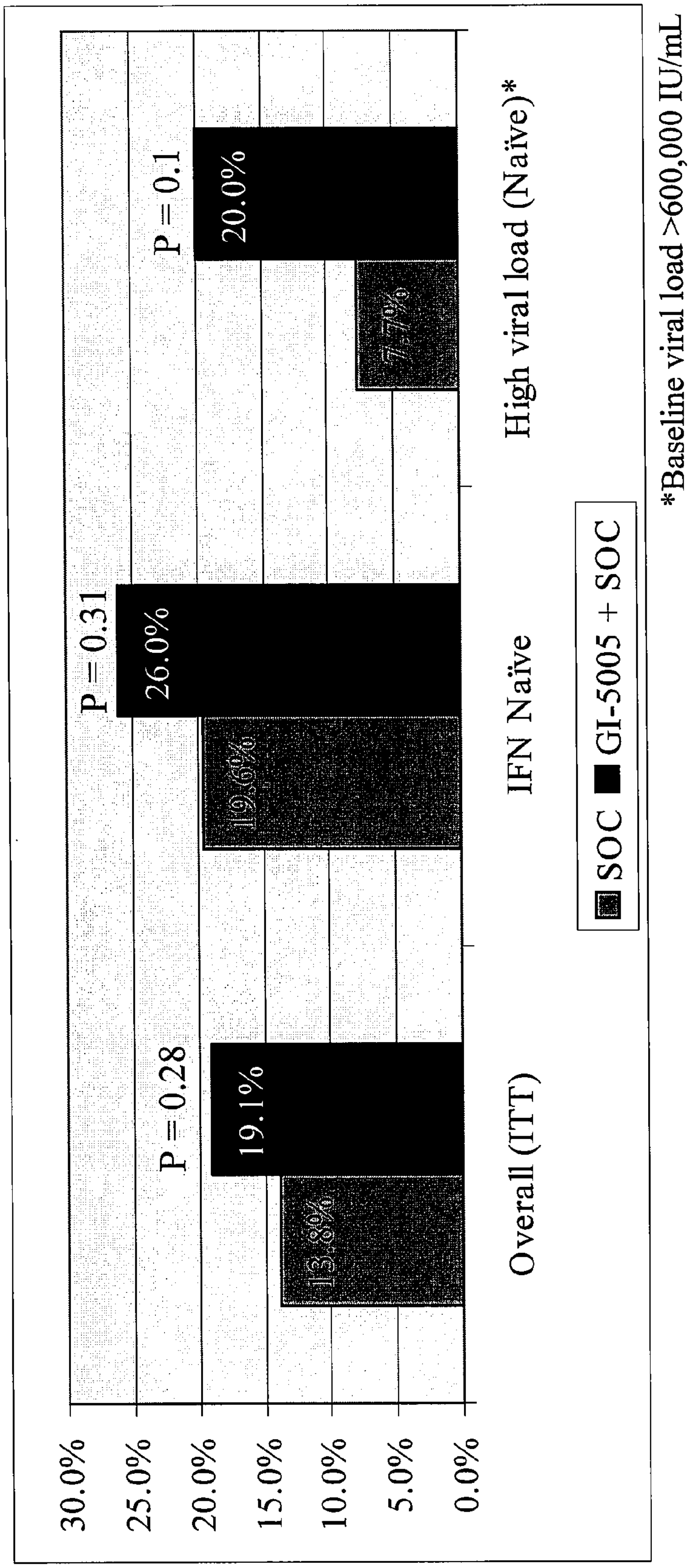

Rapid virologic response (RVR), defined as HCV RNA negativity by PCR assay (<25 IU/mL) by 4 weeks of therapy, is highly predictive of future sustained virologic response SVR for patients who go on to complete full duration of SOC. RVR rates at week 4 were assessed in the triple therapy and SOC groups in the current study (FIG. 4). A 2.6-fold advantage was observed in naïve+high load patients (patients who were naïve to interferon therapy and who had high viral loads at the baseline of the study) with a trend favoring triple therapy (20.0% vs. 7.7%, p=0.1) (FIG. 4; "High viral load (Naïve)". The majority of naïve+low load patients (patients who were naïve to interferon therapy and who had low viral loads at the baseline of the study) achieved RVR in both treatment groups, contributing to the smaller observed advantage for triple therapy in the "all naïve group" (the combined group of patients who were naïve to interferon therapy at the beginning of the trial, including both high load and low load patients; see FIG. 4, "IFN Naïve") (26.0% vs 19.6%). There were no observed RVRs in the non-responder patients from either treatment arm, thereby producing lower absolute RVR rates in the analysis of all patients as a single group (19.1% vs 13.8%) (see FIG. 4, "Overall").

Figure 5:
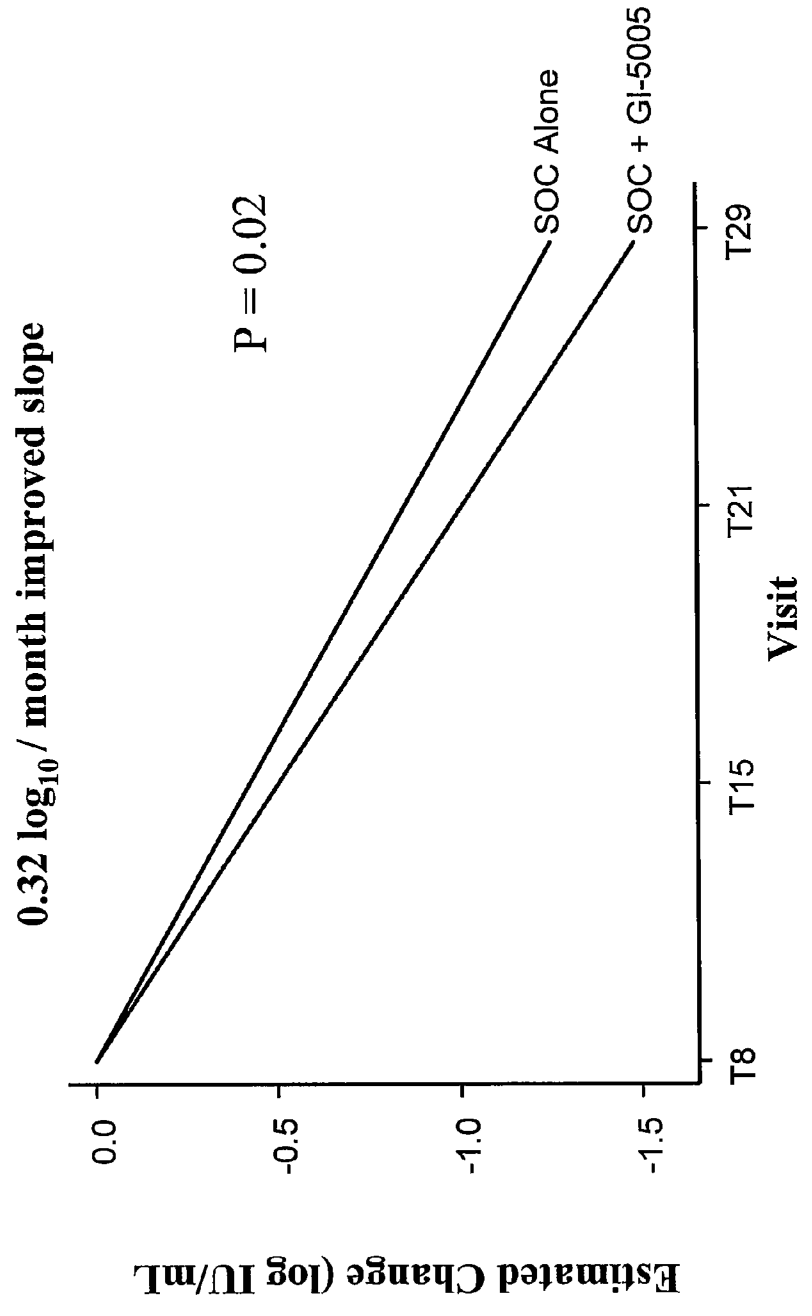
FIG. 5 is a graph showing that, as a group, all subjects (All Treated) who completed the first 4 weeks of SOC+GI-5005 (triple) therapy showed a statistically significant trend toward increased (enhanced) second phase kinetics for peripheral viral reduction as compared to all subjects treated with SOC alone.
Figure 6:
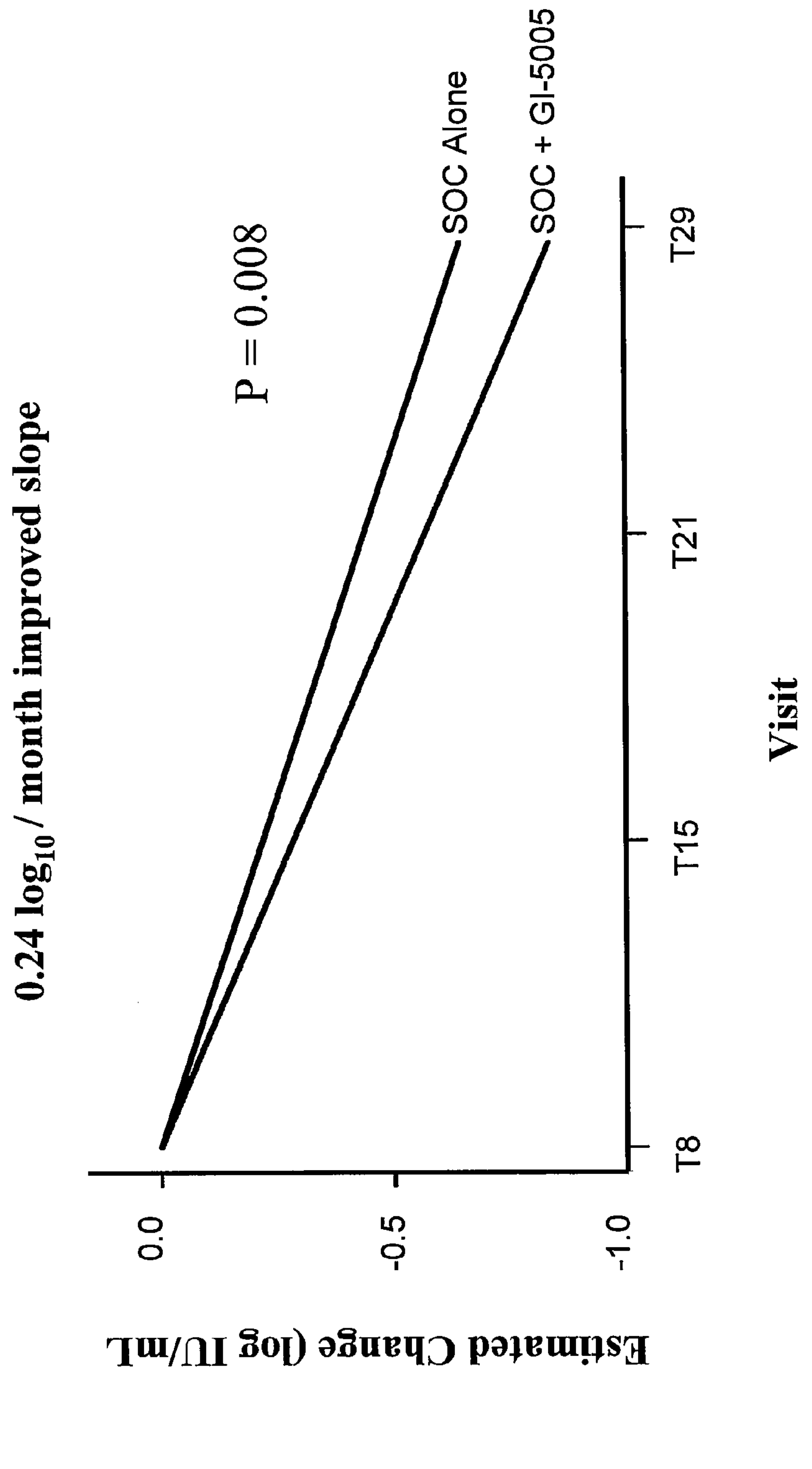
FIG. 6 is a graph showing that, as a group, subject who were prior non-responders to interferon therapy (Prior Non-responders) who completed the first 4 weeks of triple therapy showed a statistically significant trend toward increased (enhanced) second phase kinetics for peripheral viral reduction as compared to prior non-responders treated with SOC alone.
Figure 7:
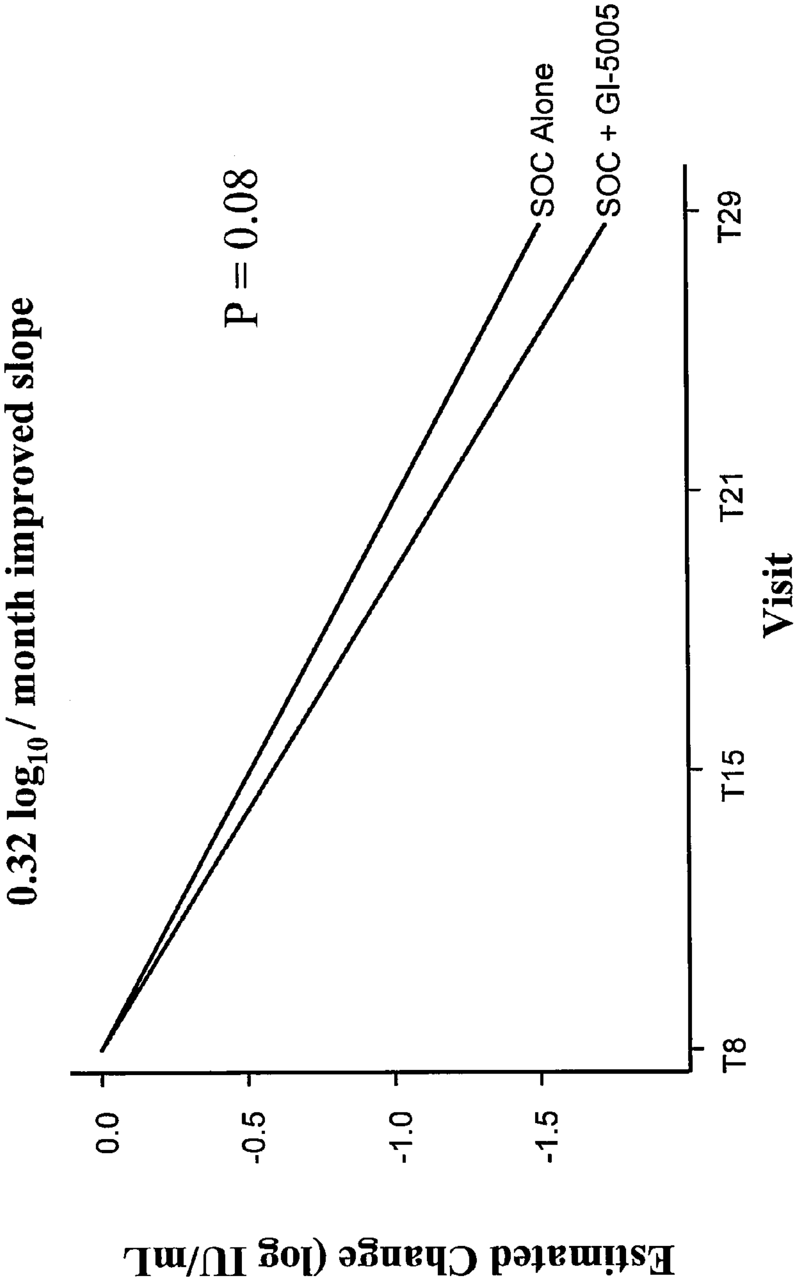
FIG. 7 is a graph showing that, as a group, subjects who were interferon-naïve subjects (Interferon Naive) who completed the first 4 weeks of triple therapy showed a strong trend toward increased (enhanced) second phase kinetics for peripheral viral reduction, as compared to interferon-naïve subjects treated with SOC alone.
Figure 8:
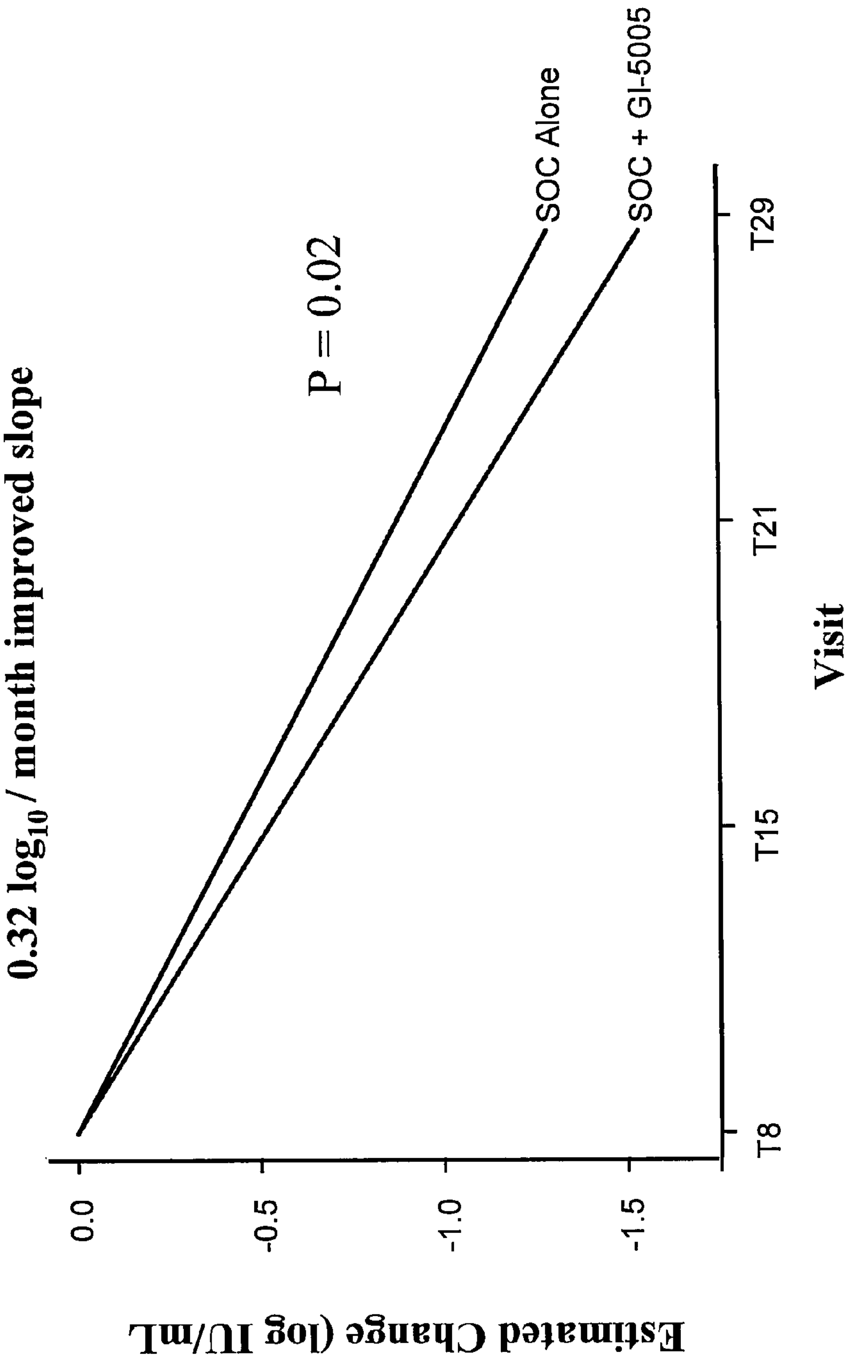
FIG. 8 is a graph showing that, as a group, all subjects having a high viral load at baseline (High Viral Load at Baseline) who completed the first 4 weeks of triple therapy showed a statistically significant trend toward increased (enhanced) second phase kinetics for peripheral viral reduction, as compared to subjects having a high viral load at baseline who were treated with SOC alone.

Second phase viral kinetic clearance reflects the rate of clearance of the hepatic reservoir of HCV-infected cells. Day 8 was considered the baseline for the calculation of second phase viral kinetics, and samples from Day 15, Day 22, and Day 29 were used to establish the slope of clearance using a repeated measures linear mixed effects model to estimate the change from Day 8 to Day 29. Missing HCV RNA values at Day 8 were imputed by the value at Day 15 or Day 22. Analysis includes all patients with at least an HCV RNA value at Day 8 (actual or imputed) and Day 29. As shown in FIGS. 5-9, all major patient subgroups showed an increased rate of second phase kinetics of peripheral viral reduction which favored triple therapy over SOC. More particularly, three subgroups achieved statistical significance: (1) all patients evaluated as a single group (FIG. 5, All Treated); (2) prior non-responders to an interferon-based therapy (FIG. 6, Prior Non-responders); and patients having a high viral load at the baseline for the study (FIG. 8, High Viral Load at Baseline), with p=0.02, p=0.008, and p=0.02 respectively. Two subgroups showed strong trends favoring triple therapy: (1) interferon-naïve patients (FIG. 7, Interferon Naïve), and patients who were both interferon-naïve and had a high viral load at the baseline for the study (FIG. 9, Interferon-Naïve & High Viral Load at Baseline), with p=0.08 and p=0.06 respectively.

During the 12 week GI-5005 monotherapy phase, no patients discontinued therapy due to adverse events. During triple therapy combination with SOC, there have been no deaths in either arm to date, and there have been no immunotherapy-related serious adverse events or dose limiting toxicity events. The most commonly reported non-serious adverse events (defined as >5% incidence) considered by the principal investigator to be related to GI-5005 included injection site erythema (12%), fatigue (9%), and headache (9%). Accordingly, GI-5005 is well tolerated and safe to date in this clinical trial.

In conclusion, the combination of GI-5005 immunotherapy plus SOC (interferon and ribavirin) demonstrated a 2.6-fold improvement in RVR rates compared to SOC alone in treatment naïve patients with high baseline HCV RNA levels. In addition this triple therapy demonstrated a ~2-fold improvement over four weeks in the linear rate of viral clearance (0.24-0.32 $\log_{10}$/month) compared with SOC alone in all relevant subgroups, including prior non-responders to interferon-based therapy. This improved rate of clearance would project to a 3 to 4 $\log_{10}$ improved reduction of virus if sustained for the full 48-72 week regimen. The improvement in the rate of second phase viral kinetic clearance is consistent with the proposed mechanism of GI-5005-induced improved elimination of infected hepatic cells. Accordingly, combination with SOC is believed to be a novel triple therapy approach that can result in improved SVR rates and may also serve as an optimized backbone therapy to which other novel antiviral agents could be added. In addition, combination with different inhibitors of viral replication, such as small molecule polymerase and protease inhibitors may result in the future ability to spare or eliminate components of the current standard of care (pegylated IFN or ribavirin).

Example 4

The following example describes the early virologic endpoint analysis of the phase 2 trial of subjects treated with GI-5005 immunotherapy in combination with interferon/ribavirin therapy.

This example shows results from the complete 12 week virologic endpoint analysis (EVR and cEVR) of the phase 2 clinical trial of subjects treated with GI-5005 immunotherapy in combination with interferon/ribavirin therapy (triple therapy), and demonstrates that administration of an immunotherapeutic composition to patients chronically infected with HCV prior to combination therapy with interferon and ribavirin results in a strong trend toward improvement of the early viral response (EVR) in certain patient subgroups. More particularly, this Example describes the analysis of all patients in both arms of the phase 2 clinical trial described in Example 2 after completion of 12 weeks of therapy with interferon/ribavirin. Results present the safety and EVR for the complete dataset.

Interim results reporting on 52/72 of the triple therapy subjects and 65/68 SOC subjects who were evaluable for EVR at the time of interim analysis (≥2 $\log_{10}$ reduction in HCV RNA at week 12, with last observation carried forward) were evaluated. Specifically, once patients reached week 12 after the start of interferon/ribavirin therapy, viral titers were measured. At this interim analysis, which included about 84% of the complete patient cohort, triple therapy showed a trend for improved EVR in all naïve subjects (34/36 {94.4%} vs. 40/46 {87%} p=0.23) and naïve subjects with high baseline viral load (>600,000 IU/mL) (28/30 {93.3%} vs. 35/41 {85.4%} p=0.26), as groups. EVR was comparable for triple therapy and SOC in the small subset of prior non-responder subjects. Accordingly, the interim analysis indicated improved EVR rates for interferon-naïve subjects (subjects who had not been treated with interferon prior to this trial), despite an unusually high EVR rate in the SOC group (compared to other reported hepatitis clinical trials using SOC). These data were consistent with the improved 4-week RVR rates.

Subsequently, once the entire cohort of patients reached the 12 week point after start of interferon/ribavirin therapy, viral titers were evaluated for the complete set of patients in both arms of the phase 2 clinical trial. Results, illustrated in FIGS. 10A and 10B, continued to show a strong trend toward improved EVR in the immunotherapy arm of the trial for interferon-naïve patients, as a group, as compared to the SOC arm. Results were evaluated with respect to all patients in the trial (FIG. 10A) and with respect to only those patients who were at clinical trial sites in the United States (FIG. 10B), to look at any potential differences in outcomes based on geographic location of treatment.

The results in FIGS. 10A and 10B show that there is an 8-12% improvement in EVR rates in naïve subgroups receiving triple therapy (94-95% Naïve or 93-94% Naïve high viral load (HVL) achieving EVR) as compared to naïve subgroups receiving SOC alone (85-87% Naïve or 82-85% naïve HVL achieving EVR). Taken together with the results shown at earlier time points, improvements in viral kinetics, RVR and EVR are expected to lead to an advantage in virologic response for triple therapy compared to SOC as measured by SVR.

Example 5

The following example describes the end of treatment endpoint analysis of the phase 2 trial of subjects treated with GI-5005 immunotherapy in combination with interferon/ribavirin therapy.

This example shows results from the complete 48 week virologic endpoint analysis (end of treatment response, or ETR) of the phase 2 clinical trial of subjects treated with GI-5005 immunotherapy in combination with interferon/ribavirin therapy (triple therapy), and demonstrates that administration of an immunotherapeutic composition to patients chronically infected with HCV prior to combination therapy with interferon and ribavirin results in an improvement in the end of treatment response (ETR) in the group of all patients (interferon-naïve and non-responders combined), and also in the subgroup of interferon-naïve patients. More particularly, this Example describes the analysis of all patients in both arms of the phase 2 clinical trial described in Example 2 after completion of 48 weeks of therapy with interferon/ribavirin.

More specifically, triple therapy at 48 weeks was well tolerated with no significant new toxicities observed and an equivalent number of SOC discontinuations due to adverse events in each group; Triple-5/68 (7.3%) and SOC-5/65 (7.7%). As shown in FIG. 13, improvement in end of treatment response (HCV RNA<25 IU/mL by PCR assay at 48 weeks) was observed in naïve genotype 1 patients in the triple therapy group compared to SOC alone (all randomized); Triple—37/53 (70%) vs SOC—27/49 (55%), one-tailed Fisher's exact test p=0.09. A similar treatment effect was observed viewing all patients as a group (naïve and non-responder together; data not shown). Complete response (HCV RNA<25 IU/mL) was assessed in non-responders at week 48 (all randomized); Triple-6/19 (32%) vs SOC-6/19 (32%). Race, baseline viral load, SOC compliance, and discontinuations did not reveal a significant influence on the observed treatment effect.

The mITT (modified Intent To Treat) analysis (analysis of only those patients who actually received at least one treatment dose in the study) shows a consistent treatment effect of 15%; Triple 37/50 (74%) vs. SOC 27/46 (59%) (FIG. 14A) with week 48 complete virologic response rates that are comparable to those of recently reported protease inhibitor triple therapy regimens. A similar treatment effect was observed in all patients (naïve and non-responders) using mITT analysis (FIG. 14B).

These results demonstrate a substantial improvement in complete virologic response at week 48 in patients receiving GI-5005 triple therapy compared to SOC alone. This is the first example of a therapeutic vaccine delivering a substantial difference in a long term, clinically meaningful virologic endpoint such as complete virologic response. Furthermore, based on GI-5005's immune-mediated mechanism of action, patients receiving GI-5005 triple therapy are expected to experience continued benefit in the post treatment period and should experience better ETR to SVR conversion. In total, these data support the use of GI-5005 triple therapy as well as novel combination strategies for GI-5005 with other HCV inhibitory agents.

Example 6

The following example describes the sustained virologic endpoint analysis of the phase 2 trial of subjects treated with GI-5005 immunotherapy in combination with interferon/ribavirin therapy.

At 6 months after end of treatment, viral titers are measured. It is expected that a higher number of patients, representing either a trend, strong trend or a statistically significant number, including at least naïve patients, will achieve SVR in the immunotherapy arm of the trial than in the SOC arm. Accordingly, it is expected that among patients in the immunotherapy arm of the trial (triple therapy), the rate of relapsers will be lower than in the SOC only arm. Improved liver function and/or decreased liver damage is also expected in the group of patients receiving triple therapy as compared to the SOC group, as measured by ALT analysis, Fibrotest scores, and/or tissue biopsy.

Example 7

The following example describes the immunological analysis of subjects treated using immunotherapy in combination with interferon/ribavirin therapy.

Briefly, blood samples are collected from all patients at baseline and at subsequent timepoints, and peripheral blood mononuclear cells (PBMCs) are collected and stored.

Immunology assays (ELISpot) are performed on each PBMC sample from each timepoint. ELISpot measures the number of subject T cells activated in response to HCV antigens ex vivo.

More particularly, an ELISpot assay is run on peripheral blood mononuclear cells (PBMCs) from subjects at select study visits. The PBMCs are mixed with various HCV peptides derived from HCV antigen sequences ex vivo and analyzed for interferon-γ (IFNγ) production, a hallmark of antigen-specific T cell activation. Pools of non-optimized HCV peptides and pools of optimized HCV peptides are used for ex vivo stimulation of subject PBMCs. Controls include mitogen stimulation with phorbol myristate acetate (PMA) and ionomycin, CEF peptide pools, HIV gag peptide pools and/or medium alone. In some assays, dependent upon sufficient numbers of cells, immunotherapeutic products designated GI-5005, GI-5003 and YVEC may also be used for in vitro restimulation of the PBMCs. PBMCs are then harvested after ex vivo peptide stimulation and the number of cells (or "spots") per million PBMCs that produce IFNγ are measured using the enzyme-linked immunosorbant (ELISpot) assay. In some assays, CD4 and CD8 T cell depletions of the PBMCs are performed prior to assay.

Culture supernatants from ELISPOT assays are collected after overnight stimulation of the PBMCs and stored at −80° C. for future analysis. For select supernatants, analysis using immunoassays from Luminex Corporation (Austin, Tex.) is performed for multiple select cytokines and other markers associated with an emerging T cell mediated response to HCV, using these culture supernatants derived as described above. Multi-analyte profiling beads enable detection of up to 30 different cytokines and chemokines per reaction in panels. Select supernatants from up to five timepoints are run per patient.

The immunoassay results are expected to reveal an HCV specific immune response that is elicited in the subjects as a result of immunotherapy.

Example 8

The following example describes the results of liver analysis in subjects treated with GI-5005 immunotherapy in combination with interferon/ribavirin therapy.

Viral load and alanine aminotransferase (ALT) levels were and continue to be measured on every subject visit (baseline and each subsequent visit). ALT is a well-validated measure of hepatic injury and serves as a surrogate for hepatic inflammation. In prior large hepatitis trials, reductions and/or normalization of ALT levels have been shown to correlate with improved liver function and reduced liver fibrosis as determined by serial biopsy. ALT normalization is defined as at least 2 ALT values<ULN (upper limit of normal) on consecutive study visits for patients with ALT>ULN at Day 1.

Results of the ALT evaluation at 12 weeks after start of interferon/ribavirin therapy (FIG. 11A) and at 24 weeks after start of interferon/ribavirin therapy (FIG. 11B) showed that GI-5005 immunotherapy in combination with interferon/ribavirin therapy (triple therapy) demonstrated a 10-15% improvement in ALT normalization in treatment naïve patient subgroups (Naïve and Naïve HVL).

In addition to ALT levels, in order to further evaluate liver function and liver damage in the clinical trial subjects, all patients were evaluated by Actitest and Fibrotest at 24 weeks after start of interferon/ribavirin therapy. Actitest determines the proportion of patients who improved from moderate to minimal liver necrosis or from severe to moderate or minimal liver necrosis as measured by Actitest. Fibrotest determines the proportion of patients who improved from moderate to minimal fibrosis or from severe to moderate or minimal fibrosis as measured by Fibrotest.

As shown in FIG. 12A, triple therapy demonstrated up to a 14% advantage in naïve patient subgroups with categorically improved serum Actitest scores compared to SOC. FIG. 12B shows that triple therapy demonstrated increased proportions (up to 2-fold) of patients with categorically improved serum fibrotest scores and decreased proportions (as much as 50% reduction) of patients with categorically worsened serum fibrotest scores, compared to SOC.

ALT normalization values were also evaluated at 48 weeks after start of interferon/ribavirin therapy in triple therapy and SOC groups (FIGS. 15A-15E). At 48 weeks (ETR), the results showed that GI-5005 immunotherapy in combination with interferon/ribavirin therapy (triple therapy) resulted in a notable improvement in ALT normalization in subject receiving this therapy as compared to those receiving SOC alone. This result was observed not only in all subjects viewed as a whole, but in various subgroups based on prior treatment history.

FIG. 15A is a graph showing that, at 48 weeks, triple therapy demonstrated a 21.1% improvement in ALT normalization in the group of all subjects as compared to the group of all subjects receiving SOC alone.

FIG. 15B is a graph showing that, at 48 weeks, triple therapy demonstrated a 19.5% improvement in ALT normalization in the group of all subjects with a high viral load at baseline as compared to the group of all subjects with a high viral load at baseline receiving SOC alone.

FIG. 15C is a graph showing that, at 48 weeks, triple therapy demonstrated a 23.5% improvement in ALT normalization in the group of interferon-naïve subjects as compared to the group of interferon-naïve subjects receiving SOC alone.

FIG. 15D is a graph showing that, at 48 weeks, triple therapy demonstrated a 22.3% improvement in ALT normalization in the group of interferon-naïve subjects who had a high viral load at baseline as compared to the group of interferon-naïve subjects who had a high viral load at baseline receiving SOC alone.

FIG. 15E is a graph showing that, at 48 weeks, triple therapy demonstrated a 13.3% improvement in ALT normalization in the group of prior non-responders as compared to the group of prior non-responders receiving SOC alone.

In total, analysis of liver function and/or liver damage indicates that an advantage in liver histology, which will be measured by paired biopsy assessment, is indicated in patients receiving GI-5005 immunotherapy in combination with interferon/ribavirin therapy as compared to those receiving SOC alone. Accordingly, immunotherapy is believed to improve liver function and/or inhibit liver damage in patients chronically infected with hepatitis C virus, which is anticipated to improve long term liver function and reduce long term effects of hepatitis, including hepatic cirrhosis and/or liver cancer. Additional liver assessment of the patients in this study are expected to confirm these results.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method to increase the frequency of rapid virologic responses (RVR) and/or early virologic responses (EVR/cEVR) in a population of subjects chronically infected with hepatitis C virus (HCV), as compared to RVR and EVR/cEVR in a population of subjects chronically infected with HCV and treated only with combination interferon and anti-viral therapy, the method comprising administering to the population of subjects an immunotherapeutic composition comprising a yeast vehicle expressing at least one HCV antigen or immunogenic domain thereof that elicits a T cell-mediated immune response against one or more HCV antigens in combination with interferon and an anti-viral compound.

2. The method of claim 1, wherein the immunotherapeutic composition is first administered at least 12 weeks prior to the first administration of the combination of interferon and the anti-viral compound.

3. A method to increase the number of complete responders in a population of subjects chronically infected with hepatitis C virus (HCV), as compared to the number of complete responders in a population of subjects chronically infected with HCV that is treated only with interferon and anti-viral therapy, the method comprising administering to the population of subjects an immunotherapeutic composition comprising a yeast vehicle expressing at least one HCV antigen or immunogenic domain thereof that elicits a T cell-mediated immune response against one or more HCV antigens in combination with interferon and an anti-viral compound.

4. The method of claim 3, wherein the immunotherapeutic composition is first administered at least 12 weeks prior to the first administration of the combination of interferon and the anti-viral compound.

5. A method to treat a subject who is chronically infected with HCV, comprising:

a) administering an immunotherapeutic composition comprising a yeast vehicle expressing at least one HCV antigen or immunogenic domain thereof that elicits a T cell-mediated immune response against one or more HCV antigens to the subject for at least 4 to 12 weeks, followed by administering interferon and anti-viral concurrently with continued administration of the immunotherapeutic composition;

b) determining the rapid virologic response (RVR) of the subject at about 4 weeks after the first administration of interferon and anti-viral compound; and c) reducing the dosage and/or frequency of one or both of the interferon or anti-viral compound in subjects with an RVR that is statistically significantly greater or strongly trending toward greater than the expected RVR of a subject treated with a combination of interferon and the anti-viral compound alone.

6. A method to continue treatment of a chronically HCV-infected subject who is predicted to fail combination interferon-anti-viral compound therapy, comprising administering to the subject an immunotherapeutic composition comprising a yeast vehicle expressing at least one HCV antigen or immunogenic domain thereof that elicits a T cell-mediated immune response against one or more HCV antigens.

7. The method of claim 6, wherein the subject continues receiving combination interferon-anti-viral compound therapy during the period of time in which the immunotherapeutic composition is administered.

8. A method to treat chronic hepatitis C virus (HCV) infection, comprising administering to a subject who is naïve to any prior interferon-based treatment for HCV an immunotherapeutic composition comprising a yeast vehicle expressing at least one HCV antigen or immunogenic domain thereof, and further administering to the subject one or both of at least one interferon and at least one anti-viral compound;

wherein the immunotherapeutic composition elicits a T cell-mediated immune response against one or more HCV antigens; and wherein the interferon and anti-viral compound are first administered at least 4 weeks after the immunotherapeutic composition is first administered.

9. The method of claim 8, wherein additional doses of the immunotherapeutic composition are administered during the same period as the administration of the interferon and the anti-viral compound.

10. The method of claim 8, wherein the immunotherapeutic composition is administered weekly for five weeks, followed by monthly administration.

11. The method of claim 8, wherein the subject is naïve to any prior interferon-based treatment for HCV and has a high viral titer at baseline (>600,000 IU/ml HCV RNA levels).

12. The method of claim 8, wherein the interferon is pegylated interferon-α.

13. The method of claim 8, wherein the anti-viral compound is ribavirin or a functional analog thereof.

14. The method of claim 8, wherein the anti-viral compound is an NS3 protease inhibitor.

15. The method of claim 8, wherein the method decreases liver damage in the subject.

16. The method of claim 8, wherein the yeast vehicle is a whole yeast.

17. The method of claim 8, wherein the yeast vehicle is from *Saccharomyces*.

18. The method of claim 8, wherein the immunotherapeutic composition comprises an HCV NS3-Core fusion protein comprising HCV sequences, wherein the HCV sequences consist of an HCV NS3 protease sequence or at least one immunogenic domain thereof linked to an HCV Core sequence or at least one immunogenic domain thereof, wherein the HCV NS3 protease sequence lacks the catalytic domain of a natural HCV NS3 protease, wherein the composition elicits an HCV NS3-specific immune response and an HCV Core-specific immune response.

19. The method of claim 18, wherein the fusion protein consists of SEQ ID NO:2.

* * * * *

SEQUENCE LISTING

<160> NUMBER OF SEQ ID NOS: 20

<210> SEQ ID NO 1
<211> LENGTH: 1233
<212> TYPE: DNA
<213> ORGANISM: Artificial
<220> FEATURE:
<223> OTHER INFORMATION: recombinant fusion protein construct

<400> SEQUENCE: 1

```
atggccgacg aggcaccaca aggttcccgc tcattgacac cctgtacctg cggctcctcg     60

gacctttacc tggtcacgag gcacgccgat gtcattcccg tgcgccggcg aggtgatagc    120

aggggtagcc tgctttcgcc ccggcccatt tcctacttga aaggctcctc gggggggtccg   180

ctgttgtgcc ccgcgggaca cgccgtgggc ctattcaggg ccgcggtgtg cacccgtgga    240

gtggctaaag cggtggactt tatccctgtg gagaacctag ggacaaccat gagatccccg    300

gtgttcacgg acaactcctc tccaccagca gtgccccaga gcttccaggt ggcccacctg    360

catgctccca ccggcagcgg taagagcacc aaggtcccgg ctgcgtacgc agcccagggc    420

tacaaggtgt tggtgctcaa cccctctgtt gctgcaacgc tgggctttgg tgcttacatg    480

tccaaggccc atggggttga tcctaatatc aggaccgggg tgagaacaat taccactggc    540

agccccatca cgtactccac ctacggcaag ttccttgccg acggcgggtg ctcaggaggt    600

gcttatgaca taataatttg tgacgagtgc cactccacgg atgccacatc catcttgggc    660

atcggcactg tccttgacca agcagagact gcgggggcga gactggttgt gctcgccact    720

gctacccctc cgggctccgt cactgtgtcc catcctaaca tcgaggaggt tgctctgtcc    780

accaccggag agatcccctt ttacactagt acgaatccta aacctcaaag aaaaaccaaa    840

cgtaacacca accgtcgccc acaggacgtc aagttcccgg gtggcggtca gatcgttggt    900

ggagtttact tgttgccgcg caggggccct agattgggtg tgcgcgcgac gaggaagact    960

tccgagcggt cgcaacctcg aggtagacgt cagcctatcc ccaaggcacg tcggcccgag   1020

ggcaggacct gggctcagcc cgggtaccct tggcccctct atggcaatga gggttgcggg   1080

tgggcgggat ggctcctgtc tccccgtggc tctcggccta gctggggccc cacagacccc   1140

cggcgtaggt cgcgcaattt gggtaaggtc atcgataccc ttacgtgcgg cttcgccgac   1200

ctcatggggt acataccgct cgtcgaggac tag                                1233
```

<210> SEQ ID NO 2
<211> LENGTH: 410
<212> TYPE: PRT
<213> ORGANISM: Artificial
<220> FEATURE:
<223> OTHER INFORMATION: recombinant fusion protein

<400> SEQUENCE: 2

```
Met Ala Asp Glu Ala Pro Gln Gly Ser Arg Ser Leu Thr Pro Cys Thr
1               5                   10                  15

Cys Gly Ser Ser Asp Leu Tyr Leu Val Thr Arg His Ala Asp Val Ile
            20                  25                  30

Pro Val Arg Arg Arg Gly Asp Ser Arg Gly Ser Leu Leu Ser Pro Arg
        35                  40                  45

Pro Ile Ser Tyr Leu Lys Gly Ser Ser Gly Gly Pro Leu Leu Cys Pro
    50                  55                  60

Ala Gly His Ala Val Gly Leu Phe Arg Ala Ala Val Cys Thr Arg Gly
65                  70                  75                  80
```

```
Val Ala Lys Ala Val Asp Phe Ile Pro Val Glu Asn Leu Gly Thr Thr
                85                  90                  95

Met Arg Ser Pro Val Phe Thr Asp Asn Ser Ser Pro Pro Ala Val Pro
            100                 105                 110

Gln Ser Phe Gln Val Ala His Leu His Ala Pro Thr Gly Ser Gly Lys
        115                 120                 125

Ser Thr Lys Val Pro Ala Ala Tyr Ala Ala Gln Gly Tyr Lys Val Leu
    130                 135                 140

Val Leu Asn Pro Ser Val Ala Ala Thr Leu Gly Phe Gly Ala Tyr Met
145                 150                 155                 160

Ser Lys Ala His Gly Val Asp Pro Asn Ile Arg Thr Gly Val Arg Thr
                165                 170                 175

Ile Thr Thr Gly Ser Pro Ile Thr Tyr Ser Thr Tyr Gly Lys Phe Leu
            180                 185                 190

Ala Asp Gly Gly Cys Ser Gly Gly Ala Tyr Asp Ile Ile Ile Cys Asp
        195                 200                 205

Glu Cys His Ser Thr Asp Ala Thr Ser Ile Leu Gly Ile Gly Thr Val
    210                 215                 220

Leu Asp Gln Ala Glu Thr Ala Gly Ala Arg Leu Val Val Leu Ala Thr
225                 230                 235                 240

Ala Thr Pro Pro Gly Ser Val Thr Val Ser His Pro Asn Ile Glu Glu
                245                 250                 255

Val Ala Leu Ser Thr Thr Gly Glu Ile Pro Phe Tyr Thr Ser Thr Asn
            260                 265                 270

Pro Lys Pro Gln Arg Lys Thr Lys Arg Asn Thr Asn Arg Arg Pro Gln
        275                 280                 285

Asp Val Lys Phe Pro Gly Gly Gly Gln Ile Val Gly Gly Val Tyr Leu
    290                 295                 300

Leu Pro Arg Arg Gly Pro Arg Leu Gly Val Arg Ala Thr Arg Lys Thr
305                 310                 315                 320

Ser Glu Arg Ser Gln Pro Arg Gly Arg Arg Gln Pro Ile Pro Lys Ala
                325                 330                 335

Arg Arg Pro Glu Gly Arg Thr Trp Ala Gln Pro Gly Tyr Pro Trp Pro
            340                 345                 350

Leu Tyr Gly Asn Glu Gly Cys Gly Trp Ala Gly Trp Leu Leu Ser Pro
        355                 360                 365

Arg Gly Ser Arg Pro Ser Trp Gly Pro Thr Asp Pro Arg Arg Arg Ser
    370                 375                 380

Arg Asn Leu Gly Lys Val Ile Asp Thr Leu Thr Cys Gly Phe Ala Asp
385                 390                 395                 400

Leu Met Gly Tyr Ile Pro Leu Val Glu Asp
                405                 410
```

<210> SEQ ID NO 3
<211> LENGTH: 1914
<212> TYPE: DNA
<213> ORGANISM: Artificial
<220> FEATURE:
<223> OTHER INFORMATION: recombinant fusion protein construct

<400> SEQUENCE: 3

```
atggccgacg aggcaccagc gcccatcacg gcgtacgccc agcagacgag aggcctccta      60

gggtgtataa tcaccagcct gactggccgg gacaaaaacc aagtggaggg tgaggtccag     120

atcgtgtcaa ctgctaccca aaccttcctg gcaacgtgca tcaatggggt atgctggact     180
```

-continued

```
gtctaccacg gggccggaac gaggaccatc gcatcaccca agggtcctgt catccagatg    240

tataccaatg tggaccaaga ccttgtgggc tggcccgctc ctcaaggttc ccgctcattg    300

acaccctgta cctgcggctc ctcggacctt tacctggtca cgaggcacgc cgatgtcatt    360

cccgtgcgcc ggcgaggtga tagcaggggt agcctgcttt cgccccggcc catttcctac    420

ttgaaaggct ccgctggggg tccgctgttg tgccccgcgg gacacgccgt gggcctattc    480

agggccgcgg tgtgcacccg tggagtggct aaagcggtgg actttatccc tgtggagaac    540

ctagggacaa ccatgagatc cccggtgttc acggacaact cctctccacc agcagtgccc    600

cagagcttcc aggtggccca cctgcatgct cccaccggca gcggtaagag caccaaggtc    660

ccggctgcgt acgcagccca gggctacaag gtgttggtgc tcaacccctc tgttgctgca    720

acgctgggct ttggtgctta catgtccaag gcccatgggg ttgatcctaa tatcaggacc    780

ggggtgagaa caattaccac tggcagcccc atcacgtact ccacctacgg caagttcctt    840

gccgacggcg ggtgctcagg aggtgcttat gacataataa tttgtgacga gtgccactcc    900

acggatgcca catccatctt gggcatcggc actgtccttg accaagcaga gactgcgggg    960

gcgagactgg ttgtgctcgc cactgctacc cctccgggct ccgtcactgt gtcccatcct   1020

aacatcgagg aggttgctct gtccaccacc ggagagatcc ccttttacgg caaggctatc   1080

cccctcgagg tgatcaaggg gggaagacat ctcatcttct gccactcaaa gaagaagtgc   1140

gacgagctcg ccgcgaagct ggtcgcattg ggcatcaatg ccgtggccta ctaccgcggt   1200

cttgacgtgt ctgtcatccc gaccagcggc gatgttgtcg tcgtgtcgac cgatgctctc   1260

atgactggct ttaccggcga cttcgactct gtgatagact gcaacacgtg tgtcactcag   1320

acagtcgatt tcagccttga ccctaccttt accattgaga caaccacgct cccccaggat   1380

gctgtctcca ggactcaacg ccggggcagg actggcaggg ggaagccagg catctataga   1440

tttgtggcac cgggggagcg cccctccggc atgttcgact cgtccgtcct ctgtgagtgc   1500

tatgacgcgg gctgtgcttg gtatgagctc acgcccgccg agactacagt taggctacga   1560

gcgtacatga acaccccggg gcttcccgtg tgccaggacc atcttgaatt ttgggagggc   1620

gtctttacgg gcctcactca tatagatgcc cactttttat cccagacaaa gcagagtggg   1680

gagaactttc cttacctggt agcgtaccaa gccaccgtgt gcgctagggc tcaagcccct   1740

cccccatcgt gggaccagat gtggaagtgt ttgatccgcc ttaaacccac cctccatggg   1800

ccaacacccc tgctatacag actgggcgct gttcagaatg aagtcaccct gacgcaccca   1860

atcaccaaat acatcatgac atgcatgtcg gccgacctgg aggtcgtcac gtag          1914
```

<210> SEQ ID NO 4
<211> LENGTH: 637
<212> TYPE: PRT
<213> ORGANISM: Artificial
<220> FEATURE:
<223> OTHER INFORMATION: recombinant fusion protein

<400> SEQUENCE: 4

```
Met Ala Asp Glu Ala Pro Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
            20                  25                  30

Asn Gln Val Glu Gly Glu Val Gln Ile Val Ser Thr Ala Thr Gln Thr
        35                  40                  45

Phe Leu Ala Thr Cys Ile Asn Gly Val Cys Trp Thr Val Tyr His Gly
    50                  55                  60
```

-continued

Ala Gly Thr Arg Thr Ile Ala Ser Pro Lys Gly Pro Val Ile Gln Met
65 70 75 80

Tyr Thr Asn Val Asp Gln Asp Leu Val Gly Trp Pro Ala Pro Gln Gly
85 90 95

Ser Arg Ser Leu Thr Pro Cys Thr Cys Gly Ser Ser Asp Leu Tyr Leu
100 105 110

Val Thr Arg His Ala Asp Val Ile Pro Val Arg Arg Arg Gly Asp Ser
115 120 125

Arg Gly Ser Leu Leu Ser Pro Arg Pro Ile Ser Tyr Leu Lys Gly Ser
130 135 140

Ala Gly Gly Pro Leu Leu Cys Pro Ala Gly His Ala Val Gly Leu Phe
145 150 155 160

Arg Ala Ala Val Cys Thr Arg Gly Val Ala Lys Ala Val Asp Phe Ile
165 170 175

Pro Val Glu Asn Leu Gly Thr Thr Met Arg Ser Pro Val Phe Thr Asp
180 185 190

Asn Ser Ser Pro Pro Ala Val Pro Gln Ser Phe Gln Val Ala His Leu
195 200 205

His Ala Pro Thr Gly Ser Gly Lys Ser Thr Lys Val Pro Ala Ala Tyr
210 215 220

Ala Ala Gln Gly Tyr Lys Val Leu Val Leu Asn Pro Ser Val Ala Ala
225 230 235 240

Thr Leu Gly Phe Gly Ala Tyr Met Ser Lys Ala His Gly Val Asp Pro
245 250 255

Asn Ile Arg Thr Gly Val Arg Thr Ile Thr Thr Gly Ser Pro Ile Thr
260 265 270

Tyr Ser Thr Tyr Gly Lys Phe Leu Ala Asp Gly Gly Cys Ser Gly Gly
275 280 285

Ala Tyr Asp Ile Ile Ile Cys Asp Glu Cys His Ser Thr Asp Ala Thr
290 295 300

Ser Ile Leu Gly Ile Gly Thr Val Leu Asp Gln Ala Glu Thr Ala Gly
305 310 315 320

Ala Arg Leu Val Val Leu Ala Thr Ala Thr Pro Pro Gly Ser Val Thr
325 330 335

Val Ser His Pro Asn Ile Glu Glu Val Ala Leu Ser Thr Thr Gly Glu
340 345 350

Ile Pro Phe Tyr Gly Lys Ala Ile Pro Leu Glu Val Ile Lys Gly Gly
355 360 365

Arg His Leu Ile Phe Cys His Ser Lys Lys Lys Cys Asp Glu Leu Ala
370 375 380

Ala Lys Leu Val Ala Leu Gly Ile Asn Ala Val Ala Tyr Tyr Arg Gly
385 390 395 400

Leu Asp Val Ser Val Ile Pro Thr Ser Gly Asp Val Val Val Val Ser
405 410 415

Thr Asp Ala Leu Met Thr Gly Phe Thr Gly Asp Phe Asp Ser Val Ile
420 425 430

Asp Cys Asn Thr Cys Val Thr Gln Thr Val Asp Phe Ser Leu Asp Pro
435 440 445

Thr Phe Thr Ile Glu Thr Thr Thr Leu Pro Gln Asp Ala Val Ser Arg
450 455 460

Thr Gln Arg Arg Gly Arg Thr Gly Arg Gly Lys Pro Gly Ile Tyr Arg
465 470 475 480

Phe Val Ala Pro Gly Glu Arg Pro Ser Gly Met Phe Asp Ser Ser Val
485 490 495

```
Leu Cys Glu Cys Tyr Asp Ala Gly Cys Ala Trp Tyr Glu Leu Thr Pro
            500                 505                 510

Ala Glu Thr Thr Val Arg Leu Arg Ala Tyr Met Asn Thr Pro Gly Leu
        515                 520                 525

Pro Val Cys Gln Asp His Leu Glu Phe Trp Glu Gly Val Phe Thr Gly
    530                 535                 540

Leu Thr His Ile Asp Ala His Phe Leu Ser Gln Thr Lys Gln Ser Gly
545                 550                 555                 560

Glu Asn Phe Pro Tyr Leu Val Ala Tyr Gln Ala Thr Val Cys Ala Arg
                565                 570                 575

Ala Gln Ala Pro Pro Pro Ser Trp Asp Gln Met Trp Lys Cys Leu Ile
            580                 585                 590

Arg Leu Lys Pro Thr Leu His Gly Pro Thr Pro Leu Leu Tyr Arg Leu
        595                 600                 605

Gly Ala Val Gln Asn Glu Val Thr Leu Thr His Pro Ile Thr Lys Tyr
    610                 615                 620

Ile Met Thr Cys Met Ser Ala Asp Leu Glu Val Val Thr
625                 630                 635


<210> SEQ ID NO 5
<211> LENGTH: 1491
<212> TYPE: DNA
<213> ORGANISM: Artificial
<220> FEATURE:
<223> OTHER INFORMATION: recombinant fusion protein construct

<400> SEQUENCE: 5

atggccgacg aggcaccata ccaagtgcgc aattcctcgg ggctttacca tgtcaccaat     60

gattgcccta actcgagtat tgtgtacgag gcggccgatg ccatcctgca cactccgggg    120

tgtgtccctt gcgttcgcga gggtaacgcc tcgaggtgtt gggtggcggt gacccccacg    180

gtggccacca gggacggcaa actccccaca acgcagcttc gacgtcatat cgatctgctt    240

gtcgggagcg ccaccctctg ctcggccctc tacgtggggg acctgtgcgg gtctgtcttt    300

cttgttggtc aactgtttac cttctctccc aggcgccact ggacgacgca agactgcaat    360

tgttctatct atcccggcca tataacgggt catcgcatgg catgggatat gatgatgaac    420

tggtccccta cggcagcgtt ggtggtagct cagctgctcc ggatcccaca agccatcatg    480

gacatggaaa cccacgtcac cgggggaagt gccggccgca ccacggctgg gcttgttggt    540

ctccttacac caggcgccaa gcagaacatc caactgatca acaccaacgg cagttggcac    600

atcaatagca cggccttgaa ctgcaatgaa agccttaaca ccggctggtt agcagggctc    660

ttctatcagc acaaattcaa ctcttcaggc tgtcctgaga ggttggccag ctgccgacgc    720

cttaccgatt ttgcccaggg ctggggtcct atcagttatg ccaacggaag cggcctcgac    780

gaacgcccct actgctggca ctaccctcca agaccttgtg gcattgtgcc cgcaaagagc    840

gtgtgtggcc cggtatattg cttcactccc agccccgtgg tggtgggaac gaccgacagg    900

tcgggcgcgc ctacctacag ctggggtgca aatgatacgg atgtcttcgt ccttaacaac    960

accaggccac cgctgggcaa ttggttcggt tgtacctgga tgaactcaac tggattcacc   1020

aaagtgtgcg gagcgccccc ttgtgtcatc ggaggggtgg gcaacaacac cttgctctgc   1080

cccactgatt gtttccgcaa gcatccggaa gccacatact ctcggtgcgg ctccggtccc   1140

tggattacac ccaggtgcat ggtcgactac ccgtataggc tttggcacta tccttgtacc   1200

atcaattaca ccatattcaa agtcaggatg tacgtgggag ggtcgagcaa caggctggaa   1260
```

-continued

```
gcggcctgca actggacgcg gggcgaacgc tgtgatctgg aagacaggga caggtccgag   1320

ctcagcccat tgctgctgtc caccacacag tggcaggtcc ttccgtgttc tttcacgacc   1380

ctgccagcct tgtccaccgg cctcatccac ctccaccaga acattgtgga cgtgcagtac   1440

ttgtacgggg tagggtcaag catcgcgtcc tgggccatta agtgggagta g            1491
```

<210> SEQ ID NO 6
<211> LENGTH: 496
<212> TYPE: PRT
<213> ORGANISM: Artificial
<220> FEATURE:
<223> OTHER INFORMATION: recombinant fusion protein

<400> SEQUENCE: 6

```
Met Ala Asp Glu Ala Pro Tyr Gln Val Arg Asn Ser Ser Gly Leu Tyr
1               5                   10                  15

His Val Thr Asn Asp Cys Pro Asn Ser Ser Ile Val Tyr Glu Ala Ala
            20                  25                  30

Asp Ala Ile Leu His Thr Pro Gly Cys Val Pro Cys Val Arg Glu Gly
        35                  40                  45

Asn Ala Ser Arg Cys Trp Val Ala Val Thr Pro Thr Val Ala Thr Arg
    50                  55                  60

Asp Gly Lys Leu Pro Thr Thr Gln Leu Arg Arg His Ile Asp Leu Leu
65                  70                  75                  80

Val Gly Ser Ala Thr Leu Cys Ser Ala Leu Tyr Val Gly Asp Leu Cys
                85                  90                  95

Gly Ser Val Phe Leu Val Gly Gln Leu Phe Thr Phe Ser Pro Arg Arg
            100                 105                 110

His Trp Thr Thr Gln Asp Cys Asn Cys Ser Ile Tyr Pro Gly His Ile
        115                 120                 125

Thr Gly His Arg Met Ala Trp Asp Met Met Met Asn Trp Ser Pro Thr
    130                 135                 140

Ala Ala Leu Val Val Ala Gln Leu Leu Arg Ile Pro Gln Ala Ile Met
145                 150                 155                 160

Asp Met Glu Thr His Val Thr Gly Gly Ser Ala Gly Arg Thr Thr Ala
                165                 170                 175

Gly Leu Val Gly Leu Leu Thr Pro Gly Ala Lys Gln Asn Ile Gln Leu
            180                 185                 190

Ile Asn Thr Asn Gly Ser Trp His Ile Asn Ser Thr Ala Leu Asn Cys
        195                 200                 205

Asn Glu Ser Leu Asn Thr Gly Trp Leu Ala Gly Leu Phe Tyr Gln His
    210                 215                 220

Lys Phe Asn Ser Ser Gly Cys Pro Glu Arg Leu Ala Ser Cys Arg Arg
225                 230                 235                 240

Leu Thr Asp Phe Ala Gln Gly Trp Gly Pro Ile Ser Tyr Ala Asn Gly
                245                 250                 255

Ser Gly Leu Asp Glu Arg Pro Tyr Cys Trp His Tyr Pro Pro Arg Pro
            260                 265                 270

Cys Gly Ile Val Pro Ala Lys Ser Val Cys Gly Pro Val Tyr Cys Phe
        275                 280                 285

Thr Pro Ser Pro Val Val Val Gly Thr Thr Asp Arg Ser Gly Ala Pro
    290                 295                 300

Thr Tyr Ser Trp Gly Ala Asn Asp Thr Asp Val Phe Val Leu Asn Asn
305                 310                 315                 320

Thr Arg Pro Pro Leu Gly Asn Trp Phe Gly Cys Thr Trp Met Asn Ser
                325                 330                 335
```

```
Thr Gly Phe Thr Lys Val Cys Gly Ala Pro Pro Cys Val Ile Gly Gly
            340                 345                 350

Val Gly Asn Asn Thr Leu Leu Cys Pro Thr Asp Cys Phe Arg Lys His
        355                 360                 365

Pro Glu Ala Thr Tyr Ser Arg Cys Gly Ser Gly Pro Trp Ile Thr Pro
    370                 375                 380

Arg Cys Met Val Asp Tyr Pro Tyr Arg Leu Trp His Tyr Pro Cys Thr
385                 390                 395                 400

Ile Asn Tyr Thr Ile Phe Lys Val Arg Met Tyr Val Gly Gly Val Glu
                405                 410                 415

His Arg Leu Glu Ala Ala Cys Asn Trp Thr Arg Gly Glu Arg Cys Asp
            420                 425                 430

Leu Glu Asp Arg Asp Arg Ser Glu Leu Ser Pro Leu Leu Leu Ser Thr
        435                 440                 445

Thr Gln Trp Gln Val Leu Pro Cys Ser Phe Thr Thr Leu Pro Ala Leu
    450                 455                 460

Ser Thr Gly Leu Ile His Leu His Gln Asn Ile Val Asp Val Gln Tyr
465                 470                 475                 480

Leu Tyr Gly Val Gly Ser Ser Ile Ala Ser Trp Ala Ile Lys Trp Glu
                485                 490                 495
```

<210> SEQ ID NO 7
<211> LENGTH: 483
<212> TYPE: DNA
<213> ORGANISM: Artificial
<220> FEATURE:
<223> OTHER INFORMATION: recombinant fusion protein construct

<400> SEQUENCE: 7

```
atggccgacg aggcaccatc tcagcactta ccgtacatcg agcaagggat gatgctcgct      60

gagcagttca agcagaaggc cctcggcctc ctgcagaccg cgtcccgcca tgcagaggtt     120

atcacccctg ctgtccagac caactggcag aaactcgagg tcttctgggc gaagcacatg     180

tggaatttca tcagtgggat acaatacttg gcgggcctgt caactagtcc tggagccctt     240

gtagtcggtg tggtctgcgc agcaatactg cgccggcacg ttggcccggg cgagggggca     300

gtgcaatgga tgaaccggct aatagccttc gcctcccggg ggaaccatgt ttcccccacg     360

cactacgtgc cggagagcga tgcagccgcc cgcgtcactg ccatactcag cagcctcact     420

gtaacccagc tcctgaggcg actgcatcag tggataagct cggagtgtac cactccatgc     480

tag                                                                   483
```

<210> SEQ ID NO 8
<211> LENGTH: 160
<212> TYPE: PRT
<213> ORGANISM: Artificial
<220> FEATURE:
<223> OTHER INFORMATION: recombinant fusion protein

<400> SEQUENCE: 8

```
Met Ala Asp Glu Ala Pro Ser Gln His Leu Pro Tyr Ile Glu Gln Gly
1               5                   10                  15

Met Met Leu Ala Glu Gln Phe Lys Gln Lys Ala Leu Gly Leu Leu Gln
            20                  25                  30

Thr Ala Ser Arg His Ala Glu Val Ile Thr Pro Ala Val Gln Thr Asn
        35                  40                  45

Trp Gln Lys Leu Glu Val Phe Trp Ala Lys His Met Trp Asn Phe Ile
    50                  55                  60
```

-continued

Ser Gly Ile Gln Tyr Leu Ala Gly Leu Ser Thr Ser Pro Gly Ala Leu
65 70 75 80

Val Val Gly Val Val Cys Ala Ala Ile Leu Arg Arg His Val Gly Pro
85 90 95

Gly Glu Gly Ala Val Gln Trp Met Asn Arg Leu Ile Ala Phe Ala Ser
100 105 110

Arg Gly Asn His Val Ser Pro Thr His Tyr Val Pro Glu Ser Asp Ala
115 120 125

Ala Ala Arg Val Thr Ala Ile Leu Ser Ser Leu Thr Val Thr Gln Leu
130 135 140

Leu Arg Arg Leu His Gln Trp Ile Ser Ser Glu Cys Thr Thr Pro Cys
145 150 155 160

<210> SEQ ID NO 9
<211> LENGTH: 6
<212> TYPE: PRT
<213> ORGANISM: Artificial
<220> FEATURE:
<223> OTHER INFORMATION: synthetic peptide

<400> SEQUENCE: 9

Met Ala Asp Glu Ala Pro
1 5

<210> SEQ ID NO 10
<211> LENGTH: 9
<212> TYPE: PRT
<213> ORGANISM: Artificial
<220> FEATURE:
<223> OTHER INFORMATION: synthetic peptide

<400> SEQUENCE: 10

Gly Gly Gly His His His His His His
1 5

<210> SEQ ID NO 11
<211> LENGTH: 2256
<212> TYPE: DNA
<213> ORGANISM: Artificial
<220> FEATURE:
<223> OTHER INFORMATION: recombinant fusion protein construct

<400> SEQUENCE: 11
atggccgacg aggcaccaag cacgaatcct aaacctcaaa gaaaaaccaa acgtaacacc 60
aaccgtcgcc cacaggacgt caagttcccg ggtggcggtc agatcgttgg tggagtttac 120
ttgttgccgc gcaggggccc tagattgggt gtgcgcgcga cgaggaagac ttccgagcgg 180
tcgcaacctc gaggtagacg tcagcctatc cccaaggcac gtcggcccga gggcaggacc 240
tgggctcagc ccgggtaccc ttggcccctc tatggcaatg agggttgcgg gtgggcggga 300
tggctcctgt ctccccgtgg ctctcggcct agctggggcc ccacagaccc ccggcgtagg 360
tcgcgcaatt tgggtaaggt catcgatacc cttacgtgcg gcttcgccga cctcatgggg 420
tacataccgc tcgtcggcgc ccctcttgga ggcgctgcca gggccctggc gcatggcgtc 480
cgggttctgg aagacggcgt gaactatgca acagggaacc ttcctggttg ctctttctct 540
atcttccttc tggccctgct ctcttgcctg actgtgcccg cttcagccta ccaagtgcgc 600
aattcctcgg ggctttacca tgtcaccaat gattgcccta actcgagtat tgtgtacgag 660
gcggccgatg ccatcctgca cactccgggg tgtgtccctt gcgttcgcga gggtaacgcc 720
tcgaggtgtt gggtggcggt gacccccacg gtggccacca gggacggcaa actccccaca 780

```
acgcagcttc gacgtcatat cgatctgctt gtcgggagcg ccaccctctg ctcggccctc     840

tacgtggggg acctgtgcgg gtctgtcttt cttgttggtc aactgtttac cttctctccc     900

aggcgccact ggacgacgca agactgcaat tgttctatct atcccggcca tataacgggt     960

catcgcatgg catgggatat gatgatgaac tggtccccta cggcagcgtt ggtggtagct    1020

cagctgctcc ggatcccaca agccatcatg gacatgatcg ctggtgctca ctggggagtc    1080

ctggcgggca tagcgtattt ctccatggtg gggaactggg cgaaggtcct ggtagtgctg    1140

ctgctatttg ccggcgtcga cgcggaaacc cacgtcaccg gggaagtgc cggccgcacc     1200

acggctgggc ttgttggtct ccttacacca ggcgccaagc agaacatcca actgatcaac    1260

accaacggca gttggcacat caatagcacg gccttgaact gcaatgaaag ccttaacacc    1320

ggctggttag cagggctctt ctatcagcac aaattcaact cttcaggctg tcctgagagg    1380

ttggccagct gccgacgcct taccgatttt gcccagggct ggggtcctat cagttatgcc    1440

aacggaagcg gcctcgacga acgcccctac tgctggcact accctccaag accttgtggc    1500

attgtgcccg caaagagcgt gtgtggcccg gtatattgct tcactcccag ccccgtggtg    1560

gtgggaacga ccgacaggtc gggcgcgcct acctacagct ggggtgcaaa tgatacggat    1620

gtcttcgtcc ttaacaacac caggccaccg ctgggcaatt ggttcggttg tacctggatg    1680

aactcaactg gattcaccaa agtgtgcgga gcgcccccctt gtgtcatcgg aggggtgggc   1740

aacaacacct tgctctgccc cactgattgt ttccgcaagc atccggaagc cacatactct    1800

cggtgcggct ccggtccctg gattacaccc aggtgcatgg tcgactaccc gtataggctt    1860

tggcactatc cttgtaccat caattacacc atattcaaag tcaggatgta cgtgggaggg    1920

gtcgagcaca ggctggaagc ggcctgcaac tggacgcggg gcgaacgctg tgatctggaa    1980

gacagggaca ggtccgagct cagcccattg ctgctgtcca ccacacagtg gcaggtcctt    2040

ccgtgttctt tcacgaccct gccagccttg tccaccggcc tcatccacct ccaccagaac    2100

attgtggacg tgcagtactt gtacggggta gggtcaagca tcgcgtcctg ggccattaag    2160

tgggagtacg tcgttctcct gttcctcctg cttgcagacg cgcgcgtctg ctcctgcttg    2220

tggatgatgt tactcatatc ccaagcggag gcgtag                              2256
```

<210> SEQ ID NO 12
<211> LENGTH: 751
<212> TYPE: PRT
<213> ORGANISM: Artificial
<220> FEATURE:
<223> OTHER INFORMATION: recombinant fusion protein

<400> SEQUENCE: 12

```
Met Ala Asp Glu Ala Pro Ser Thr Asn Pro Lys Pro Gln Arg Lys Thr
1               5                   10                  15

Lys Arg Asn Thr Asn Arg Arg Pro Gln Asp Val Lys Phe Pro Gly Gly
            20                  25                  30

Gly Gln Ile Val Gly Gly Val Tyr Leu Leu Pro Arg Arg Gly Pro Arg
        35                  40                  45

Leu Gly Val Arg Ala Thr Arg Lys Thr Ser Glu Arg Ser Gln Pro Arg
    50                  55                  60

Gly Arg Arg Gln Pro Ile Pro Lys Ala Arg Arg Pro Glu Gly Arg Thr
65                  70                  75                  80

Trp Ala Gln Pro Gly Tyr Pro Trp Pro Leu Tyr Gly Asn Glu Gly Cys
                85                  90                  95

Gly Trp Ala Gly Trp Leu Leu Ser Pro Arg Gly Ser Arg Pro Ser Trp
```

-continued

```
            100                 105                 110

Gly Pro Thr Asp Pro Arg Arg Arg Ser Arg Asn Leu Gly Lys Val Ile
        115                 120                 125

Asp Thr Leu Thr Cys Gly Phe Ala Asp Leu Met Gly Tyr Ile Pro Leu
    130                 135                 140

Val Gly Ala Pro Leu Gly Gly Ala Ala Arg Ala Leu Ala His Gly Val
145                 150                 155                 160

Arg Val Leu Glu Asp Gly Val Asn Tyr Ala Thr Gly Asn Leu Pro Gly
                165                 170                 175

Cys Ser Phe Ser Ile Phe Leu Leu Ala Leu Leu Ser Cys Leu Thr Val
            180                 185                 190

Pro Ala Ser Ala Tyr Gln Val Arg Asn Ser Ser Gly Leu Tyr His Val
        195                 200                 205

Thr Asn Asp Cys Pro Asn Ser Ser Ile Val Tyr Glu Ala Ala Asp Ala
    210                 215                 220

Ile Leu His Thr Pro Gly Cys Val Pro Cys Val Arg Glu Gly Asn Ala
225                 230                 235                 240

Ser Arg Cys Trp Val Ala Val Thr Pro Thr Val Ala Thr Arg Asp Gly
                245                 250                 255

Lys Leu Pro Thr Thr Gln Leu Arg Arg His Ile Asp Leu Leu Val Gly
            260                 265                 270

Ser Ala Thr Leu Cys Ser Ala Leu Tyr Val Gly Asp Leu Cys Gly Ser
        275                 280                 285

Val Phe Leu Val Gly Gln Leu Phe Thr Phe Ser Pro Arg Arg His Trp
    290                 295                 300

Thr Thr Gln Asp Cys Asn Cys Ser Ile Tyr Pro Gly His Ile Thr Gly
305                 310                 315                 320

His Arg Met Ala Trp Asp Met Met Met Asn Trp Ser Pro Thr Ala Ala
                325                 330                 335

Leu Val Val Ala Gln Leu Leu Arg Ile Pro Gln Ala Ile Met Asp Met
            340                 345                 350

Ile Ala Gly Ala His Trp Gly Val Leu Ala Gly Ile Ala Tyr Phe Ser
        355                 360                 365

Met Val Gly Asn Trp Ala Lys Val Leu Val Val Leu Leu Leu Phe Ala
    370                 375                 380

Gly Val Asp Ala Glu Thr His Val Thr Gly Gly Ser Ala Gly Arg Thr
385                 390                 395                 400

Thr Ala Gly Leu Val Gly Leu Leu Thr Pro Gly Ala Lys Gln Asn Ile
                405                 410                 415

Gln Leu Ile Asn Thr Asn Gly Ser Trp His Ile Asn Ser Thr Ala Leu
            420                 425                 430

Asn Cys Asn Glu Ser Leu Asn Thr Gly Trp Leu Ala Gly Leu Phe Tyr
        435                 440                 445

Gln His Lys Phe Asn Ser Ser Gly Cys Pro Glu Arg Leu Ala Ser Cys
    450                 455                 460

Arg Arg Leu Thr Asp Phe Ala Gln Gly Trp Gly Pro Ile Ser Tyr Ala
465                 470                 475                 480

Asn Gly Ser Gly Leu Asp Glu Arg Pro Tyr Cys Trp His Tyr Pro Pro
                485                 490                 495

Arg Pro Cys Gly Ile Val Pro Ala Lys Ser Val Cys Gly Pro Val Tyr
            500                 505                 510

Cys Phe Thr Pro Ser Pro Val Val Val Gly Thr Thr Asp Arg Ser Gly
        515                 520                 525
```

```
Ala Pro Thr Tyr Ser Trp Gly Ala Asn Asp Thr Asp Val Phe Val Leu
    530                 535                 540

Asn Asn Thr Arg Pro Pro Leu Gly Asn Trp Phe Gly Cys Thr Trp Met
545                 550                 555                 560

Asn Ser Thr Gly Phe Thr Lys Val Cys Gly Ala Pro Pro Cys Val Ile
                565                 570                 575

Gly Gly Val Gly Asn Asn Thr Leu Leu Cys Pro Thr Asp Cys Phe Arg
            580                 585                 590

Lys His Pro Glu Ala Thr Tyr Ser Arg Cys Gly Ser Gly Pro Trp Ile
        595                 600                 605

Thr Pro Arg Cys Met Val Asp Tyr Pro Tyr Arg Leu Trp His Tyr Pro
    610                 615                 620

Cys Thr Ile Asn Tyr Thr Ile Phe Lys Val Arg Met Tyr Val Gly Gly
625                 630                 635                 640

Val Glu His Arg Leu Glu Ala Ala Cys Asn Trp Thr Arg Gly Glu Arg
                645                 650                 655

Cys Asp Leu Glu Asp Arg Asp Arg Ser Glu Leu Ser Pro Leu Leu Leu
            660                 665                 670

Ser Thr Thr Gln Trp Gln Val Leu Pro Cys Ser Phe Thr Thr Leu Pro
        675                 680                 685

Ala Leu Ser Thr Gly Leu Ile His Leu His Gln Asn Ile Val Asp Val
    690                 695                 700

Gln Tyr Leu Tyr Gly Val Gly Ser Ser Ile Ala Ser Trp Ala Ile Lys
705                 710                 715                 720

Trp Glu Tyr Val Val Leu Leu Phe Leu Leu Leu Ala Asp Ala Arg Val
                725                 730                 735

Cys Ser Cys Leu Trp Met Met Leu Leu Ile Ser Gln Ala Glu Ala
            740                 745                 750
```

<210> SEQ ID NO 13
<211> LENGTH: 1908
<212> TYPE: DNA
<213> ORGANISM: Artificial
<220> FEATURE:
<223> OTHER INFORMATION: recombinant fusion protein construct

<400> SEQUENCE: 13

```
atggccgacg aggcaccaag tacgaatcct aaacctcaaa gaaaaaccaa acgtaacacc      60

aaccgtcgcc cacaggacgt caagttcccg ggtggcggtc agatcgttgg tggagtttac     120

ttgttgccgc gcaggggccc tagattgggt gtgcgcgcga cgaggaagac ttccgagcgg     180

tcgcaacctc gaggtagacg tcagcctatc cccaaggcac gtcggcccga gggcaggacc     240

tgggctcagc ccgggtaccc ttggcccctc tatggcaatg agggttgcgg gtgggcggga     300

tggctcctgt ctccccgtgg ctctcggcct agctggggcc ccacagaccc ccggcgtagg     360

tcgcgcaatt tgggtaaggt catcgatacc cttacgtgcg gcttcgccga cctcatgggg     420

tacataccgc tcgtctacca agtgcgcaat tcctcggggc tttaccatgt caccaatgat     480

tgccctaact cgagtattgt gtacgaggcg gccgatgcca tcctgcacac tccggggtgt     540

gtcccttgcg ttcgcgaggg taacgcctcg aggtgttggg tggcggtgac ccccacggtg     600

gccaccaggg acggcaaact ccccacaacg cagcttcgac gtcatatcga tctgcttgtc     660

gggagcgcca ccctctgctc ggccctctac gtgggggacc tgtgcgggtc tgtctttctt     720

gttggtcaac tgtttacctt ctctcccagg cgccactgga cgacgcaaga ctgcaattgt     780

tctatctatc ccggccatat aacgggtcat cgcatggcat gggatatgat gatgaactgg     840
```

-continued

```
tcccctacgg cagcgttggt ggtagctcag ctgctccgga tcccacaagc catcatggac    900

atggaaaccc acgtcaccgg gggaagtgcc ggccgcacca cggctgggct tgttggtctc    960

cttacaccag gcgccaagca gaacatccaa ctgatcaaca ccaacggcag ttggcacatc   1020

aatagcacgg ccttgaactg caatgaaagc cttaacaccg gctggttagc agggctcttc   1080

tatcagcaca aattcaactc ttcaggctgt cctgagaggt tggccagctg ccgacgcctt   1140

accgattttg cccagggctg ggtcctatc agttatgcca acggaagcgg cctcgacgaa   1200

cgcccctact gctggcacta ccctccaaga ccttgtggca ttgtgcccgc aaagagcgtg   1260

tgtggcccgg tatattgctt cactcccagc cccgtggtgg tgggaacgac cgacaggtcg   1320

ggcgcgccta cctacagctg ggtgcaaat gatacggatg tcttcgtcct taacaacacc   1380

aggccaccgc tgggcaattg gttcggttgt acctggatga actcaactgg attcaccaaa   1440

gtgtgcggag cgccccccttg tgtcatcgga ggggtgggca acaacacctt gctctgcccc   1500

actgattgtt tccgcaagca tccggaagcc acatactctc ggtgcggctc cggtccctgg   1560

attacaccca ggtgcatggt cgactacccg tataggcttt ggcactatcc ttgtaccatc   1620

aattacacca tattcaaagt caggatgtac gtgggagggg tcgagcacag gctggaagcg   1680

gcctgcaact ggacgcgggg cgaacgctgt gatctggaag acagggacag gtccgagctc   1740

agcccattgc tgctgtccac cacacagtgg caggtccttc cgtgttcttt cacgaccctg   1800

ccagccttgt ccaccggcct catccacctc caccagaaca ttgtggacgt gcagtacttg   1860

tacggggtag ggtcaagcat cgcgtcctgg gccattaagt gggagtag                1908


<210> SEQ ID NO 14
<211> LENGTH: 635
<212> TYPE: PRT
<213> ORGANISM: Artificial
<220> FEATURE:
<223> OTHER INFORMATION: recombinant fusion protein

<400> SEQUENCE: 14

Met Ala Asp Glu Ala Pro Ser Thr Asn Pro Lys Pro Gln Arg Lys Thr
1               5                   10                  15

Lys Arg Asn Thr Asn Arg Arg Pro Gln Asp Val Lys Phe Pro Gly Gly
            20                  25                  30

Gly Gln Ile Val Gly Gly Val Tyr Leu Leu Pro Arg Arg Gly Pro Arg
        35                  40                  45

Leu Gly Val Arg Ala Thr Arg Lys Thr Ser Glu Arg Ser Gln Pro Arg
    50                  55                  60

Gly Arg Arg Gln Pro Ile Pro Lys Ala Arg Arg Pro Glu Gly Arg Thr
65                  70                  75                  80

Trp Ala Gln Pro Gly Tyr Pro Trp Pro Leu Tyr Gly Asn Glu Gly Cys
                85                  90                  95

Gly Trp Ala Gly Trp Leu Leu Ser Pro Arg Gly Ser Arg Pro Ser Trp
            100                 105                 110

Gly Pro Thr Asp Pro Arg Arg Arg Ser Arg Asn Leu Gly Lys Val Ile
        115                 120                 125

Asp Thr Leu Thr Cys Gly Phe Ala Asp Leu Met Gly Tyr Ile Pro Leu
    130                 135                 140

Val Tyr Gln Val Arg Asn Ser Ser Gly Leu Tyr His Val Thr Asn Asp
145                 150                 155                 160

Cys Pro Asn Ser Ser Ile Val Tyr Glu Ala Ala Asp Ala Ile Leu His
                165                 170                 175

Thr Pro Gly Cys Val Pro Cys Val Arg Glu Gly Asn Ala Ser Arg Cys
```

-continued

```
            180                 185                 190

Trp Val Ala Val Thr Pro Thr Val Ala Thr Arg Asp Gly Lys Leu Pro
        195                 200                 205

Thr Thr Gln Leu Arg Arg His Ile Asp Leu Leu Val Gly Ser Ala Thr
    210                 215                 220

Leu Cys Ser Ala Leu Tyr Val Gly Asp Leu Cys Gly Ser Val Phe Leu
225                 230                 235                 240

Val Gly Gln Leu Phe Thr Phe Ser Pro Arg Arg His Trp Thr Thr Gln
                245                 250                 255

Asp Cys Asn Cys Ser Ile Tyr Pro Gly His Ile Thr Gly His Arg Met
            260                 265                 270

Ala Trp Asp Met Met Met Asn Trp Ser Pro Thr Ala Ala Leu Val Val
        275                 280                 285

Ala Gln Leu Leu Arg Ile Pro Gln Ala Ile Met Asp Met Glu Thr His
    290                 295                 300

Val Thr Gly Gly Ser Ala Gly Arg Thr Thr Ala Gly Leu Val Gly Leu
305                 310                 315                 320

Leu Thr Pro Gly Ala Lys Gln Asn Ile Gln Leu Ile Asn Thr Asn Gly
                325                 330                 335

Ser Trp His Ile Asn Ser Thr Ala Leu Asn Cys Asn Glu Ser Leu Asn
            340                 345                 350

Thr Gly Trp Leu Ala Gly Leu Phe Tyr Gln His Lys Phe Asn Ser Ser
        355                 360                 365

Gly Cys Pro Glu Arg Leu Ala Ser Cys Arg Arg Leu Thr Asp Phe Ala
    370                 375                 380

Gln Gly Trp Gly Pro Ile Ser Tyr Ala Asn Gly Ser Gly Leu Asp Glu
385                 390                 395                 400

Arg Pro Tyr Cys Trp His Tyr Pro Pro Arg Pro Cys Gly Ile Val Pro
                405                 410                 415

Ala Lys Ser Val Cys Gly Pro Val Tyr Cys Phe Thr Pro Ser Pro Val
            420                 425                 430

Val Val Gly Thr Thr Asp Arg Ser Gly Ala Pro Thr Tyr Ser Trp Gly
        435                 440                 445

Ala Asn Asp Thr Asp Val Phe Val Leu Asn Asn Thr Arg Pro Pro Leu
    450                 455                 460

Gly Asn Trp Phe Gly Cys Thr Trp Met Asn Ser Thr Gly Phe Thr Lys
465                 470                 475                 480

Val Cys Gly Ala Pro Pro Cys Val Ile Gly Gly Val Gly Asn Asn Thr
                485                 490                 495

Leu Leu Cys Pro Thr Asp Cys Phe Arg Lys His Pro Glu Ala Thr Tyr
            500                 505                 510

Ser Arg Cys Gly Ser Gly Pro Trp Ile Thr Pro Arg Cys Met Val Asp
        515                 520                 525

Tyr Pro Tyr Arg Leu Trp His Tyr Pro Cys Thr Ile Asn Tyr Thr Ile
    530                 535                 540

Phe Lys Val Arg Met Tyr Val Gly Gly Val Glu His Arg Leu Glu Ala
545                 550                 555                 560

Ala Cys Asn Trp Thr Arg Gly Glu Arg Cys Asp Leu Glu Asp Arg Asp
                565                 570                 575

Arg Ser Glu Leu Ser Pro Leu Leu Leu Ser Thr Thr Gln Trp Gln Val
            580                 585                 590

Leu Pro Cys Ser Phe Thr Thr Leu Pro Ala Leu Ser Thr Gly Leu Ile
        595                 600                 605
```

-continued

His Leu His Gln Asn Ile Val Asp Val Gln Tyr Leu Tyr Gly Val Gly
    610                 615                 620

Ser Ser Ile Ala Ser Trp Ala Ile Lys Trp Glu
625                 630                 635

<210> SEQ ID NO 15
<211> LENGTH: 2538
<212> TYPE: DNA
<213> ORGANISM: Artificial
<220> FEATURE:
<223> OTHER INFORMATION: recombinant fusion protein construct

<400> SEQUENCE: 15
atggccgacg aggcaccagc gcccatcacg gcgtacgccc agcagacgag aggcctccta 60
gggtgtataa tcaccagcct gactggccgg gacaaaaacc aagtggaggg tgaggtccag 120
atcgtgtcaa ctgctaccca aaccttcctg gcaacgtgca tcaatggggt atgctggact 180
gtctaccacg gggccggaac gaggaccatc gcatcaccca agggtcctgt catccagatg 240
tataccaatg tggaccaaga ccttgtgggc tggcccgctc ctcaaggttc ccgctcattg 300
acaccctgta cctgcggctc ctcggacctt tacctggtca cgaggcacgc cgatgtcatt 360
cccgtgcgcc ggcgaggtga tagcaggggt agcctgcttt cgccccggcc catttcctac 420
ttgaaaggct ccgctggggg tccgctgttg tgccccgcgg gacacgccgt gggcctattc 480
agggccgcgg tgtgcacccg tggagtggct aaagcggtgg actttatccc tgtggagaac 540
ctagggacaa ccatgagatc ccccggtgttc acggacaact cctctccacc agcagtgccc 600
cagagcttcc aggtggccca cctgcatgct cccaccggca gcggtaagag caccaaggtc 660
ccggctgcgt acgcagccca gggctacaag gtgttggtgc tcaacccctc tgttgctgca 720
acgctgggct ttggtgctta catgtccaag gcccatgggg ttgatcctaa tatcaggacc 780
ggggtgagaa caattaccac tggcagcccc atcacgtact ccacctacgg caagttcctt 840
gccgacggcg ggtgctcagg aggtgcttat gacataataa tttgtgacga gtgccactcc 900
acggatgcca catccatctt gggcatcggc actgtccttg accaagcaga gactgcgggg 960
gcgagactgg ttgtgctcgc cactgctacc cctccgggct ccgtcactgt gtcccatcct 1020
aacatcgagg aggttgctct gtccaccacc ggagagatcc ccttttacgg caaggctatc 1080
cccctcgagg tgatcaaggg gggaagacat ctcatcttct gccactcaaa gaagaagtgc 1140
gacgagctcg ccgcgaagct ggtcgcattg ggcatcaatg ccgtggccta ctaccgcggt 1200
cttgacgtgt ctgtcatccc gaccagcggc gatgttgtcg tcgtgtcgac cgatgctctc 1260
atgactggct ttaccggcga cttcgactct gtgatagact gcaacacgtg tgtcactcag 1320
acagtcgatt tcagccttga ccctaccttt accattgaga caaccacgct cccccaggat 1380
gctgtctcca ggactcaacg ccggggcagg actggcaggg ggaagccagg catctataga 1440
tttgtggcac cgggggagcg cccctccggc atgttcgact cgtccgtcct ctgtgagtgc 1500
tatgacgcgg gctgtgcttg gtatgagctc acgcccgccg agactacagt taggctacga 1560
gcgtacatga acaccccggg gcttcccgtg tgccaggacc atcttgaatt ttgggagggc 1620
gtctttacgg gcctcactca tatagatgcc cactttttat cccagacaaa gcagagtggg 1680
gagaactttc cttacctggt agcgtaccaa gccaccgtgt gcgctagggc tcaagcccct 1740
cccccatcgt gggaccagat gtggaagtgt ttgatccgcc ttaaacccac cctccatggg 1800
ccaacacccc tgctatacag actgggcgct gttcagaatg aagtcaccct gacgcaccca 1860
atcaccaaat acatcatgac atgcatgtcg gccgacctgg aggtcgtcac gagcacctgg 1920

-continued

```
gtgctcgttg gcggcgtcct ggctgctctg gccgcgtatt gcctgtcaac aggctgcgtg   1980

gtcatagtgg gcaggattgt cttgtccggg aagccggcaa ttatacctga cagggaggtt   2040

ctctaccagg agttcgatga gatggaagag tgctctcagc acttaccgta catcgagcaa   2100

gggatgatgc tcgctgagca gttcaagcag aaggccctcg gcctcctgca gaccgcgtcc   2160

cgccatgcag aggttatcac ccctgctgtc cagaccaact ggcagaaact cgaggtcttc   2220

tgggcgaagc acatgtggaa tttcatcagt gggatacaat acttggcggg cctgtcaact   2280

agtcctggag cccttgtagt cggtgtggtc tgcgcagcaa tactgcgccg gcacgttggc   2340

ccgggcgagg gggcagtgca atggatgaac cggctaatag ccttcgcctc ccgggggaac   2400

catgtttccc ccacgcacta cgtgccggag agcgatgcag ccgcccgcgt cactgccata   2460

ctcagcagcc tcactgtaac ccagctcctg aggcgactgc atcagtggat aagctcggag   2520

tgtaccactc catgctag                                                 2538
```

<210> SEQ ID NO 16
<211> LENGTH: 845
<212> TYPE: PRT
<213> ORGANISM: Artificial
<220> FEATURE:
<223> OTHER INFORMATION: recombinant fusion protein

<400> SEQUENCE: 16

```
Met Ala Asp Glu Ala Pro Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
            20                  25                  30

Asn Gln Val Glu Gly Glu Val Gln Ile Val Ser Thr Ala Thr Gln Thr
        35                  40                  45

Phe Leu Ala Thr Cys Ile Asn Gly Val Cys Trp Thr Val Tyr His Gly
    50                  55                  60

Ala Gly Thr Arg Thr Ile Ala Ser Pro Lys Gly Pro Val Ile Gln Met
65                  70                  75                  80

Tyr Thr Asn Val Asp Gln Asp Leu Val Gly Trp Pro Ala Pro Gln Gly
                85                  90                  95

Ser Arg Ser Leu Thr Pro Cys Thr Cys Gly Ser Ser Asp Leu Tyr Leu
            100                 105                 110

Val Thr Arg His Ala Asp Val Ile Pro Val Arg Arg Arg Gly Asp Ser
        115                 120                 125

Arg Gly Ser Leu Leu Ser Pro Arg Pro Ile Ser Tyr Leu Lys Gly Ser
    130                 135                 140

Ala Gly Gly Pro Leu Leu Cys Pro Ala Gly His Ala Val Gly Leu Phe
145                 150                 155                 160

Arg Ala Ala Val Cys Thr Arg Gly Val Ala Lys Ala Val Asp Phe Ile
                165                 170                 175

Pro Val Glu Asn Leu Gly Thr Thr Met Arg Ser Pro Val Phe Thr Asp
            180                 185                 190

Asn Ser Ser Pro Pro Ala Val Pro Gln Ser Phe Gln Val Ala His Leu
        195                 200                 205

His Ala Pro Thr Gly Ser Gly Lys Ser Thr Lys Val Pro Ala Ala Tyr
    210                 215                 220

Ala Ala Gln Gly Tyr Lys Val Leu Val Leu Asn Pro Ser Val Ala Ala
225                 230                 235                 240

Thr Leu Gly Phe Gly Ala Tyr Met Ser Lys Ala His Gly Val Asp Pro
                245                 250                 255
```

-continued

```
Asn Ile Arg Thr Gly Val Arg Thr Ile Thr Thr Gly Ser Pro Ile Thr
            260                 265                 270

Tyr Ser Thr Tyr Gly Lys Phe Leu Ala Asp Gly Gly Cys Ser Gly Gly
        275                 280                 285

Ala Tyr Asp Ile Ile Ile Cys Asp Glu Cys His Ser Thr Asp Ala Thr
    290                 295                 300

Ser Ile Leu Gly Ile Gly Thr Val Leu Asp Gln Ala Glu Thr Ala Gly
305                 310                 315                 320

Ala Arg Leu Val Val Leu Ala Thr Ala Thr Pro Pro Gly Ser Val Thr
                325                 330                 335

Val Ser His Pro Asn Ile Glu Glu Val Ala Leu Ser Thr Thr Gly Glu
            340                 345                 350

Ile Pro Phe Tyr Gly Lys Ala Ile Pro Leu Glu Val Ile Lys Gly Gly
        355                 360                 365

Arg His Leu Ile Phe Cys His Ser Lys Lys Lys Cys Asp Glu Leu Ala
    370                 375                 380

Ala Lys Leu Val Ala Leu Gly Ile Asn Ala Val Ala Tyr Tyr Arg Gly
385                 390                 395                 400

Leu Asp Val Ser Val Ile Pro Thr Ser Gly Asp Val Val Val Val Ser
                405                 410                 415

Thr Asp Ala Leu Met Thr Gly Phe Thr Gly Asp Phe Asp Ser Val Ile
            420                 425                 430

Asp Cys Asn Thr Cys Val Thr Gln Thr Val Asp Phe Ser Leu Asp Pro
        435                 440                 445

Thr Phe Thr Ile Glu Thr Thr Thr Leu Pro Gln Asp Ala Val Ser Arg
    450                 455                 460

Thr Gln Arg Arg Gly Arg Thr Gly Arg Gly Lys Pro Gly Ile Tyr Arg
465                 470                 475                 480

Phe Val Ala Pro Gly Glu Arg Pro Ser Gly Met Phe Asp Ser Ser Val
                485                 490                 495

Leu Cys Glu Cys Tyr Asp Ala Gly Cys Ala Trp Tyr Glu Leu Thr Pro
            500                 505                 510

Ala Glu Thr Thr Val Arg Leu Arg Ala Tyr Met Asn Thr Pro Gly Leu
        515                 520                 525

Pro Val Cys Gln Asp His Leu Glu Phe Trp Glu Gly Val Phe Thr Gly
    530                 535                 540

Leu Thr His Ile Asp Ala His Phe Leu Ser Gln Thr Lys Gln Ser Gly
545                 550                 555                 560

Glu Asn Phe Pro Tyr Leu Val Ala Tyr Gln Ala Thr Val Cys Ala Arg
                565                 570                 575

Ala Gln Ala Pro Pro Pro Ser Trp Asp Gln Met Trp Lys Cys Leu Ile
            580                 585                 590

Arg Leu Lys Pro Thr Leu His Gly Pro Thr Pro Leu Leu Tyr Arg Leu
        595                 600                 605

Gly Ala Val Gln Asn Glu Val Thr Leu Thr His Pro Ile Thr Lys Tyr
    610                 615                 620

Ile Met Thr Cys Met Ser Ala Asp Leu Glu Val Val Thr Ser Thr Trp
625                 630                 635                 640

Val Leu Val Gly Gly Val Leu Ala Ala Leu Ala Ala Tyr Cys Leu Ser
                645                 650                 655

Thr Gly Cys Val Val Ile Val Gly Arg Ile Val Leu Ser Gly Lys Pro
            660                 665                 670

Ala Ile Ile Pro Asp Arg Glu Val Leu Tyr Gln Glu Phe Asp Glu Met
        675                 680                 685
```

```
Glu Glu Cys Ser Gln His Leu Pro Tyr Ile Glu Gln Gly Met Met Leu
    690                 695                 700

Ala Glu Gln Phe Lys Gln Lys Ala Leu Gly Leu Leu Gln Thr Ala Ser
705                 710                 715                 720

Arg His Ala Glu Val Ile Thr Pro Ala Val Gln Thr Asn Trp Gln Lys
                725                 730                 735

Leu Glu Val Phe Trp Ala Lys His Met Trp Asn Phe Ile Ser Gly Ile
            740                 745                 750

Gln Tyr Leu Ala Gly Leu Ser Thr Ser Pro Gly Ala Leu Val Val Gly
        755                 760                 765

Val Val Cys Ala Ala Ile Leu Arg Arg His Val Gly Pro Gly Glu Gly
    770                 775                 780

Ala Val Gln Trp Met Asn Arg Leu Ile Ala Phe Ala Ser Arg Gly Asn
785                 790                 795                 800

His Val Ser Pro Thr His Tyr Val Pro Glu Ser Asp Ala Ala Ala Arg
                805                 810                 815

Val Thr Ala Ile Leu Ser Ser Leu Thr Val Thr Gln Leu Leu Arg Arg
            820                 825                 830

Leu His Gln Trp Ile Ser Ser Glu Cys Thr Thr Pro Cys
        835                 840                 845
```

<210> SEQ ID NO 17
<211> LENGTH: 2982
<212> TYPE: DNA
<213> ORGANISM: Artificial
<220> FEATURE:
<223> OTHER INFORMATION: recombinant fusion protein construct

<400> SEQUENCE: 17

```
atggccgacg aggcaccatc cggttcctgg ctaagggaca tctgggactg gatatgcgag     60

gtgctgagcg actttaagac ctggctgaaa gccaagctca tgccacaact gcctgggatt    120

ccctttgtgt cctgccagcg cgggtatagg ggggtctggc gaggagacgg cattatgcac    180

actcgctgcc actgtggagc tgagatcact ggacatgtca aaaacgggac gatgaggatc    240

gtcggtccta ggacctgcag gaacatgtgg agtgggacgt tccccattaa cgcctacacc    300

acgggcccct gtactcccct tcctgcgccg aactataagt tcgcgctgtg gagggtgtct    360

gcagaggaat acgtggagat aaggcgggtg gggggacttcc actacgtatc gggtatgact    420

actgacaatc ttaaatgccc gtgccagatc ccatcgcccg aatttttcac agaattggac    480

ggggtgcgcc tacataggtt tgcgcccccct tgcaagccct tgctgcggga ggaggtatca    540

ttcagagtag gactccacga gtacccggtg gggtcgcaat taccttgcga gcccgaaccg    600

gacgtagccg tgttgacgtc catgctcact gatccctccc atataacagc agaggcggcc    660

gggagaaggt tggcgagagg gtcacccccct tctatggcca gctcctcggc cagccagctg    720

tccgctccat ctctcaaggc aacttgcacc gccaaccatg actcccctga cgccgagctc    780

atagaggcta acctcctgtg gaggcaggag atgggcggca acatcaccag ggttgagtca    840

gagaacaaag tggtgattct ggactccttc gatccgcttg tggcagagga ggatgagcgg    900

gaggtctccg tacccgcaga aattctgcgg aagtctcgga gattcgcccg ggccctgccc    960

gtttgggcgc ggccggacta caaccccccg ctagtagaga cgtggaaaaa gcctgactac   1020

gaaccacctg tggtccatgg ctgcccgcta ccacctccac ggtcccctcc tgtgcctccg   1080

cctcggaaaa agcgtacggt ggtcctcacc gaatcaaccc tatctactgc cttggccgag   1140

cttgccacca aaagttttgg cagctcctca acttccggca ttacgggcga caatacgaca   1200
```

```
acatcctctg agcccgcccc ttctggctgc ccccccgact ccgacgttga gtcctattct   1260
tccatgcccc ccctggaggg ggagcctggg gatccggatc tcagcgacgg gtcatggtcg   1320
acggtcagta gtggggccga cacggaagat gtcgtgtgct gctcaatgtc ttattcctgg   1380
acaggcgcac tcgtcacccc gtgcgctgcg gaagaacaaa aactgcccat caacgcactg   1440
agcaactcgt tgctacgcca tcacaatctg gtgtattcca ccacttcacg cagtgcttgc   1500
caaaggcaga agaaagtcac atttgacaga ctgcaagttc tggacagcca ttaccaggac   1560
gtgctcaagg aggtcaaagc agcggcgtca aaagtgaagg ctaacttgct atccgtagag   1620
gaagcttgca gcctgacgcc cccacattca gccaaatcca agtttggcta tggggcaaaa   1680
gacgtccgtt gccatgccag aaaggccgta gcccacatca actccgtgtg gaaagacctt   1740
ctggaagaca gtgtaacacc aatagacact accatcatgg ccaagaacga ggttttctgc   1800
gttcagcctg agaagggggg tcgtaagcca gctcgtctca tcgtgttccc cgacctgggc   1860
gtgcgcgtgt gcgagaagat ggccctgtac gacgtggtta gcaagctccc cctggccgtg   1920
atgggaagct cctacggatt ccaatactca ccaggacagc gggttgaatt cctcgtgcaa   1980
gcgtggaagt ccaagaagac cccgatgggg ttctcgtatg atacccgctg ttttgactcc   2040
acagtcactg agagcgacat ccgtacggag gaggcaattt accaatgttg tgacctggac   2100
ccccaagccc gcgtggccat caagtccctc actgagaggc tttatgttgg gggccctctt   2160
accaattcaa ggggggaaaa ctgcggctac cgcaggtgcc gcgcgagcgg cgtactgaca   2220
actagctgtg gtaacaccct cacttgctac atcaaggccc gggcagcctg tcgagccgca   2280
gggctccagg actgcaccat gctcgtgtgt ggcgacgact tagtcgttat ctgtgaaagt   2340
gcgggggtcc aggaggacgc ggcgagcctg agagccttca cggaggctat gaccaggtac   2400
tccgcccccc ccggggaccc cccacaacca gaatacgact tggagcttat aacatcatgc   2460
tcctccaacg tgtcagtcgc ccacgacggc gctggaaaga gggtctacta ccttacccgt   2520
gaccctacaa cccccctcgc gagagccgcg tgggagacag caagacacac tccagtcaat   2580
tcctggctag gcaacataat catgtttgcc cccacactgt gggcgaggat gatactgatg   2640
acccatttct ttagcgtcct catagccagg gatcagcttg aacaggctct taactgtgag   2700
atctacggag cctgctactc catagaacca ctggatctac ctccaatcat tcaaagactc   2760
catggcctca gcgcattttc actccacagt tactctccag gtgaaatcaa tagggtggcc   2820
gcatgcctca gaaaacttgg ggtcccgccc ttgcgagctt ggagacaccg ggcccggagc   2880
gtccgcgcta ggcttctgtc cagaggaggc agggctgcca tatgtggcaa gtacctcttc   2940
aactgggcag taagaacaaa gctcaaactc actccaatat ag                      2982
```

<210> SEQ ID NO 18
<211> LENGTH: 993
<212> TYPE: PRT
<213> ORGANISM: Artificial
<220> FEATURE:
<223> OTHER INFORMATION: recombinant fusion protein

<400> SEQUENCE: 18

```
Met Ala Asp Glu Ala Pro Ser Gly Ser Trp Leu Arg Asp Ile Trp Asp
1               5                   10                  15

Trp Ile Cys Glu Val Leu Ser Asp Phe Lys Thr Trp Leu Lys Ala Lys
            20                  25                  30

Leu Met Pro Gln Leu Pro Gly Ile Pro Phe Val Ser Cys Gln Arg Gly
        35                  40                  45
```

-continued

```
Tyr Arg Gly Val Trp Arg Gly Asp Gly Ile Met His Thr Arg Cys His
    50                  55                  60

Cys Gly Ala Glu Ile Thr Gly His Val Lys Asn Gly Thr Met Arg Ile
65                  70                  75                  80

Val Gly Pro Arg Thr Cys Arg Asn Met Trp Ser Gly Thr Phe Pro Ile
                85                  90                  95

Asn Ala Tyr Thr Thr Gly Pro Cys Thr Pro Leu Pro Ala Pro Asn Tyr
            100                 105                 110

Lys Phe Ala Leu Trp Arg Val Ser Ala Glu Glu Tyr Val Glu Ile Arg
        115                 120                 125

Arg Val Gly Asp Phe His Tyr Val Ser Gly Met Thr Thr Asp Asn Leu
    130                 135                 140

Lys Cys Pro Cys Gln Ile Pro Ser Pro Glu Phe Phe Thr Glu Leu Asp
145                 150                 155                 160

Gly Val Arg Leu His Arg Phe Ala Pro Pro Cys Lys Pro Leu Leu Arg
                165                 170                 175

Glu Glu Val Ser Phe Arg Val Gly Leu His Glu Tyr Pro Val Gly Ser
            180                 185                 190

Gln Leu Pro Cys Glu Pro Glu Pro Asp Val Ala Val Leu Thr Ser Met
        195                 200                 205

Leu Thr Asp Pro Ser His Ile Thr Ala Glu Ala Ala Gly Arg Arg Leu
    210                 215                 220

Ala Arg Gly Ser Pro Pro Ser Met Ala Ser Ser Ser Ala Ser Gln Leu
225                 230                 235                 240

Ser Ala Pro Ser Leu Lys Ala Thr Cys Thr Ala Asn His Asp Ser Pro
                245                 250                 255

Asp Ala Glu Leu Ile Glu Ala Asn Leu Leu Trp Arg Gln Glu Met Gly
            260                 265                 270

Gly Asn Ile Thr Arg Val Glu Ser Glu Asn Lys Val Val Ile Leu Asp
        275                 280                 285

Ser Phe Asp Pro Leu Val Ala Glu Glu Asp Glu Arg Glu Val Ser Val
    290                 295                 300

Pro Ala Glu Ile Leu Arg Lys Ser Arg Arg Phe Ala Arg Ala Leu Pro
305                 310                 315                 320

Val Trp Ala Arg Pro Asp Tyr Asn Pro Pro Leu Val Glu Thr Trp Lys
                325                 330                 335

Lys Pro Asp Tyr Glu Pro Pro Val Val His Gly Cys Pro Leu Pro Pro
            340                 345                 350

Pro Arg Ser Pro Pro Val Pro Pro Pro Arg Lys Lys Arg Thr Val Val
        355                 360                 365

Leu Thr Glu Ser Thr Leu Ser Thr Ala Leu Ala Glu Leu Ala Thr Lys
    370                 375                 380

Ser Phe Gly Ser Ser Ser Thr Ser Gly Ile Thr Gly Asp Asn Thr Thr
385                 390                 395                 400

Thr Ser Ser Glu Pro Ala Pro Ser Gly Cys Pro Pro Asp Ser Asp Val
                405                 410                 415

Glu Ser Tyr Ser Ser Met Pro Pro Leu Glu Gly Glu Pro Gly Asp Pro
            420                 425                 430

Asp Leu Ser Asp Gly Ser Trp Ser Thr Val Ser Ser Gly Ala Asp Thr
        435                 440                 445

Glu Asp Val Val Cys Cys Ser Met Ser Tyr Ser Trp Thr Gly Ala Leu
    450                 455                 460

Val Thr Pro Cys Ala Ala Glu Glu Gln Lys Leu Pro Ile Asn Ala Leu
465                 470                 475                 480
```

```
Ser Asn Ser Leu Leu Arg His His Asn Leu Val Tyr Ser Thr Thr Ser
                485                 490                 495

Arg Ser Ala Cys Gln Arg Gln Lys Lys Val Thr Phe Asp Arg Leu Gln
            500                 505                 510

Val Leu Asp Ser His Tyr Gln Asp Val Leu Lys Glu Val Lys Ala Ala
        515                 520                 525

Ala Ser Lys Val Lys Ala Asn Leu Leu Ser Val Glu Glu Ala Cys Ser
    530                 535                 540

Leu Thr Pro Pro His Ser Ala Lys Ser Lys Phe Gly Tyr Gly Ala Lys
545                 550                 555                 560

Asp Val Arg Cys His Ala Arg Lys Ala Val Ala His Ile Asn Ser Val
                565                 570                 575

Trp Lys Asp Leu Leu Glu Asp Ser Val Thr Pro Ile Asp Thr Thr Ile
            580                 585                 590

Met Ala Lys Asn Glu Val Phe Cys Val Gln Pro Glu Lys Gly Gly Arg
        595                 600                 605

Lys Pro Ala Arg Leu Ile Val Phe Pro Asp Leu Gly Val Arg Val Cys
    610                 615                 620

Glu Lys Met Ala Leu Tyr Asp Val Val Ser Lys Leu Pro Leu Ala Val
625                 630                 635                 640

Met Gly Ser Ser Tyr Gly Phe Gln Tyr Ser Pro Gly Gln Arg Val Glu
                645                 650                 655

Phe Leu Val Gln Ala Trp Lys Ser Lys Lys Thr Pro Met Gly Phe Ser
            660                 665                 670

Tyr Asp Thr Arg Cys Phe Asp Ser Thr Val Thr Glu Ser Asp Ile Arg
        675                 680                 685

Thr Glu Glu Ala Ile Tyr Gln Cys Cys Asp Leu Asp Pro Gln Ala Arg
    690                 695                 700

Val Ala Ile Lys Ser Leu Thr Glu Arg Leu Tyr Val Gly Gly Pro Leu
705                 710                 715                 720

Thr Asn Ser Arg Gly Glu Asn Cys Gly Tyr Arg Arg Cys Arg Ala Ser
                725                 730                 735

Gly Val Leu Thr Thr Ser Cys Gly Asn Thr Leu Thr Cys Tyr Ile Lys
            740                 745                 750

Ala Arg Ala Ala Cys Arg Ala Ala Gly Leu Gln Asp Cys Thr Met Leu
        755                 760                 765

Val Cys Gly Asp Asp Leu Val Val Ile Cys Glu Ser Ala Gly Val Gln
    770                 775                 780

Glu Asp Ala Ala Ser Leu Arg Ala Phe Thr Glu Ala Met Thr Arg Tyr
785                 790                 795                 800

Ser Ala Pro Pro Gly Asp Pro Pro Gln Pro Glu Tyr Asp Leu Glu Leu
                805                 810                 815

Ile Thr Ser Cys Ser Ser Asn Val Ser Val Ala His Asp Gly Ala Gly
            820                 825                 830

Lys Arg Val Tyr Tyr Leu Thr Arg Asp Pro Thr Thr Pro Leu Ala Arg
        835                 840                 845

Ala Ala Trp Glu Thr Ala Arg His Thr Pro Val Asn Ser Trp Leu Gly
    850                 855                 860

Asn Ile Ile Met Phe Ala Pro Thr Leu Trp Ala Arg Met Ile Leu Met
865                 870                 875                 880

Thr His Phe Phe Ser Val Leu Ile Ala Arg Asp Gln Leu Glu Gln Ala
                885                 890                 895

Leu Asn Cys Glu Ile Tyr Gly Ala Cys Tyr Ser Ile Glu Pro Leu Asp
```

```
            900                 905                 910

Leu Pro Pro Ile Ile Gln Arg Leu His Gly Leu Ser Ala Phe Ser Leu
        915                 920                 925

His Ser Tyr Ser Pro Gly Glu Ile Asn Arg Val Ala Ala Cys Leu Arg
    930                 935                 940

Lys Leu Gly Val Pro Pro Leu Arg Ala Trp Arg His Arg Ala Arg Ser
945                 950                 955                 960

Val Arg Ala Arg Leu Leu Ser Arg Gly Gly Arg Ala Ala Ile Cys Gly
                965                 970                 975

Lys Tyr Leu Phe Asn Trp Ala Val Arg Thr Lys Leu Lys Leu Thr Pro
            980                 985                 990

Ile


<210> SEQ ID NO 19
<211> LENGTH: 9599
<212> TYPE: DNA
<213> ORGANISM: Hepatitis C virus

<400> SEQUENCE: 19

gccagccccc tgatgggggc gacactccac catgaatcac tcccctgtga ggaactattg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag    180

gacgaccggg tcctttcttg gataaacccg ctcaatgcct ggagatttgg gcgtgccccc    240

gcaagactgc tagccgagta gtgttgggtc gcgaaaggcc ttgtggtact gcctgatagg    300

gtgcttgcga gtgccccggg aggtctcgta gaccgtgcac catgagcacg aatcctaaac    360

ctcaaagaaa aaccaaacgt aacaccaacc gtcgcccaca ggacgtcaag ttcccgggtg    420

gcggtcagat cgttggtgga gtttacttgt tgccgcgcag gggccctaga ttgggtgtgc    480

gcgcgacgag gaagacttcc gagcggtcgc aacctcgagg tagacgtcag cctatcccca    540

aggcacgtcg gcccgagggc aggacctggg ctcagcccgg gtacccttgg cccctctatg    600

gcaatgaggg ttgcgggtgg gcgggatggc tcctgtctcc ccgtggctct cggcctagct    660

ggggccccac agacccccgg cgtaggtcgc gcaatttggg taaggtcatc gataccctta    720

cgtgcggctt cgccgacctc atggggtaca taccgctcgt cggcgcccct cttggaggcg    780

ctgccagggc cctggcgcat ggcgtccggg ttctggaaga cggcgtgaac tatgcaacag    840

ggaaccttcc tggttgctct ttctctatct tccttctggc cctgctctct tgcctgactg    900

tgcccgcttc agcctaccaa gtgcgcaatt cctcggggct ttaccatgtc accaatgatt    960

gccctaactc gagtattgtg tacgaggcgg ccgatgccat cctgcacact ccggggtgtg   1020

tcccttgcgt tcgcgagggt aacgcctcga ggtgttgggt ggcggtgacc cccacggtgg   1080

ccaccaggga cggcaaactc cccacaacgc agcttcgacg tcatatcgat ctgcttgtcg   1140

ggagcgccac cctctgctcg gccctctacg tgggggacct gtgcgggtct gtctttcttg   1200

ttggtcaact gtttaccttc tctcccaggc gccactggac gacgcaagac tgcaattgtt   1260

ctatctatcc cggccatata acgggtcatc gcatggcatg ggatatgatg atgaactggt   1320

cccctacggc agcgttggtg gtagctcagc tgctccggat cccacaagcc atcatggaca   1380

tgatcgctgg tgctcactgg ggagtcctgg cgggcatagc gtatttctcc atggtgggga   1440

actgggcgaa ggtcctggta gtgctgctgc tatttgccgg cgtcgacgcg gaaacccacg   1500

tcaccggggg aaatgccggc cgcaccacgg ctgggcttgt tggtctcctt acaccaggcg   1560

ccaagcagaa catccaactg atcaacacca acggcagttg gcacatcaat agcacggcct   1620
```

-continued

```
tgaactgcaa tgaaagcctt aacaccggct ggttagcagg gctcttctat cagcacaaat   1680
tcaactcttc aggctgtcct gagaggttga ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggacgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
ccttcctcgt gttcttctgc tttgcgtggt atctgaaggg taggtgggtg cccggagcgg   2700
cctacgcctt ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttcccccc ctcaacgtcc   2940
ggggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc acccctcttc gagactgggc gcacaacggc ctgcgagatc   3240
tggccgtggc tgtggaacca gtcgttttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgcagg   3420
cgcccatcac ggcgtacacc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt ggcaccctgc acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg ggacacgccg tgggcctatt cagggccgcg gtgtgcaccc   3900
gtggagtggc taaggcggtg gactttatcc ctgtggagaa cctagggaca accatgagat   3960
ccccggtgtt cacggacaac tcctctccac cagcagtgcc ccagagcttc caggtggccc   4020
```

```
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc cccttttacg gcaaggctat cccccctcgag gtgatcaagg   4500
ggggaagaca tctcatcttc tgccattcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gaccggcagg gggaagccag gcatctatag atttgtggca ccgggggagc   4860
gcccctccgg catgttcgac tcgtccgtcc tctgtgagtg ctatgacgcg ggctgtgctt   4920
ggtatgagct cacgcccgcc gagactacag ttaggctacg agcgtacatg aacaccccgg   4980
ggcttcccgt gtgccaggac catcttgaat tttgggaggg cgtctttacg ggcctcactc   5040
atatagatgc ccactttcta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
agttcaagca gaaggccctc ggcctcctgc agaccgcgtc ccgccatgca gaggttatca   5580
cccctgctgt ccagaccaac tggcagaaac tcgaggtctt ttgggcgaag cacatgtgga   5640
atttcatcag tgggatacaa tacttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ctgcctttgt gggcgctggc ctagctggcg ccgccatcgg cagcgttgga ctggggaagg   5880
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg ggtctggcg aggagacggc attatgcaca   6420
```

```
ctcgctgcca ctgtggagct gagatcactg gacatgtcaa aaacgggacg atgaggatcg   6480
tcggtcctag gacttgcagg aacatgtgga gtgggacgtt ccccattaac gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga atttttcaca gaattggacg   6720
gggtgcgcct acacaggttt gcgcccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcacccccctt ctatggccag ctcctcggct agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acctgcagaa attctgcgga agtctcggag attcgcccgg gccctgcccg   7200
tctgggcgcg gccggactac aaccccccgc tagtagagac gtggaaaaag cctgactacg   7260
aaccacctgt ggtccatggc tgcccgctac cacctccacg gtcccctcct gtgcctccgc   7320
ctcggaaaaa gcgtacggtg gtcctcaccg aatcaaccct atctactgcc ttggccgagc   7380
ttgccaccaa aagttttggc agctcctcaa cttccggcat tacgggcgac aatacgacaa   7440
catcctctga gcccgcccct tctggctgcc cccccgactc cgacgttgag tcctattctt   7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
caggcgcact cgtcaccccg tgcgctgcgg aagaacaaaa actgcccatc aacgcactga   7680
gcaactcgtt gctacgccat cacaatctgg tgtattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa aagtgaaggc taacttgcta tccgtagagg   7860
aagcttgcag cctgacgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga gaagggggggt cgtaagccag ctcgtctcat cgtgttcccc gacctgggcg   8100
tgcgcgtgtg cgagaagatg gccctgtacg acgtggttag caagctcccc ctggccgtga   8160
tgggaagctc ctacggattc caatactcac caggacagcg ggttgaattc ctcgtgcaag   8220
cgtggaagtc caagaagacc ccgatggggt tctcgtatga tacccgctgt tttgactcca   8280
cagtcactga gagcgacatc cgtacggagg aggcaattta ccaatgttgt gacctggacc   8340
cccaagcccg cgtggccatc aagtccctca ctgagaggct ttatgttggg ggccctctta   8400
ccaattcaag gggggaaaac tgcggctacc gcaggtgccg cgcgagcggc gtactgacaa   8460
ctagctgtgg taacaccctc acttgctaca tcaaggcccg ggcagcctgt cgagccgcag   8520
ggctccagga ctgcaccatg ctcgtgtgtg gcgacgactt agtcgttatc tgtgaaagtg   8580
cgggggtcca ggaggacgcg gcgaacctga gagccttcac ggaggctatg accaggtact   8640
ccgccccccc cggggacccc ccacaaccag aatacgactt ggagcttata acatcatgct   8700
cctccaacgt gtcagtcgcc cacgacggcg ctggaaagag ggtctactac cttacccgtg   8760
accctacaac ccccctcgcg agagccgcgt gggagacagc aagacacact ccagtcaatt   8820
```

```
cctggctagg caacataatc atgtttgccc ccacactgtg ggcgaggatg atactgatga   8880
cccatttctt tagcgtcctc atagccaggg atcagcttga acaggctctt aactgtgaga   8940
tctacggagc ctgctactcc atagaaccac tggatctacc tccaatcatt caaagactcc   9000
atggcctcag cgcattttca ctccacagtt actctccagg tgaaatcaat agggtggccg   9060
catgcctcag aaaacttggg gtcccgccct tgcgagcttg gagacaccgg gcccggagcg   9120
tccgcgctag gcttctgtcc agaggaggca gggctgccat atgtggcaag tacctcttca   9180
actgggcagt aagaacaaag ctcaaactca ccccaataac ggccgctggc cggctggact   9240
tgtccggttg gttcacggct ggctacagcg gggagacat ttatcacagc gtgtctcatg    9300
cccggccccg ctggttctgg ttttgcctac tcctgctcgc tgcaggggta ggcatctacc   9360
tcctccccaa ccgatgaagg ttggggtaaa cactccggcc tcttaagcca tttcctgttt   9420
ttttttttt ttttttttt tttttctttt tttttttctt tcctttcctt cttttttcc      9480
tttcttttc ccttctttaa tggtggctcc atcttagccc tagtcacggc tagctgtgaa    9540
aggtccgtga gccgcatgac tgcagagagt gctgatactg gcctctctgc agatcatgt    9599
```

<210> SEQ ID NO 20
<211> LENGTH: 3011
<212> TYPE: PRT
<213> ORGANISM: Hepatitis C virus

<400> SEQUENCE: 20

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240
```

-continued

```
Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Thr Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670
```

-continued

```
Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Ala Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                1005

Glu Ile  Leu Leu Gly Pro Ala  Asp Gly Met Val Ser  Lys Gly Trp
    1010                1015                1020

Arg Leu  Gln Ala Pro Ile Thr  Ala Tyr Thr Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Thr Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Pro Lys Gly  Pro Val Ile
```

```
    1085                1090                1095

Gln Met  Tyr Thr Asn Val Asp  Gln Asp Leu Val Gly  Trp Pro Ala
    1100                1105                1110

Pro Gln  Gly Ser Arg Ser Leu  Ala Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Leu Phe  Arg Ala Ala Val Cys  Thr Arg Gly
    1175                1180                1185

Val Ala  Lys Ala Val Asp Phe  Ile Pro Val Glu Asn  Leu Gly Thr
    1190                1195                1200

Thr Met  Arg Ser Pro Val Phe  Thr Asp Asn Ser Ser  Pro Pro Ala
    1205                1210                1215

Val Pro  Gln Ser Phe Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260

Phe Gly  Ala Tyr Met Ser Lys  Ala His Gly Val Asp  Pro Asn Ile
    1265                1270                1275

Arg Thr  Gly Val Arg Thr Ile  Thr Thr Gly Ser Pro  Ile Thr Tyr
    1280                1285                1290

Ser Thr  Tyr Gly Lys Phe Leu  Ala Asp Gly Gly Cys  Ser Gly Gly
    1295                1300                1305

Ala Tyr  Asp Ile Ile Ile Cys  Asp Glu Cys His Ser  Thr Asp Ala
    1310                1315                1320

Thr Ser  Ile Leu Gly Ile Gly  Thr Val Leu Asp Gln  Ala Glu Thr
    1325                1330                1335

Ala Gly  Ala Arg Leu Val Val  Leu Ala Thr Ala Thr  Pro Pro Gly
    1340                1345                1350

Ser Val  Thr Val Ser His Pro  Asn Ile Glu Glu Val  Ala Leu Ser
    1355                1360                1365

Thr Thr  Gly Glu Ile Pro Phe  Tyr Gly Lys Ala Ile  Pro Leu Glu
    1370                1375                1380

Val Ile  Lys Gly Gly Arg His  Leu Ile Phe Cys His  Ser Lys Lys
    1385                1390                1395

Lys Cys  Asp Glu Leu Ala Ala  Lys Leu Val Ala Leu  Gly Ile Asn
    1400                1405                1410

Ala Val  Ala Tyr Tyr Arg Gly  Leu Asp Val Ser Val  Ile Pro Thr
    1415                1420                1425

Ser Gly  Asp Val Val Val Val  Ser Thr Asp Ala Leu  Met Thr Gly
    1430                1435                1440

Phe Thr  Gly Asp Phe Asp Ser  Val Ile Asp Cys Asn  Thr Cys Val
    1445                1450                1455

Thr Gln  Thr Val Asp Phe Ser  Leu Asp Pro Thr Phe  Thr Ile Glu
    1460                1465                1470

Thr Thr  Thr Leu Pro Gln Asp  Ala Val Ser Arg Thr  Gln Arg Arg
    1475                1480                1485
```

-continued

```
Gly Arg  Thr Gly Arg Gly Lys  Pro Gly Ile Tyr Arg  Phe Val Ala
    1490                 1495                 1500

Pro Gly  Glu Arg Pro Ser Gly  Met Phe Asp Ser Ser  Val Leu Cys
    1505                 1510                 1515

Glu Cys  Tyr Asp Ala Gly Cys  Ala Trp Tyr Glu Leu  Thr Pro Ala
    1520                 1525                 1530

Glu Thr  Thr Val Arg Leu Arg  Ala Tyr Met Asn Thr  Pro Gly Leu
    1535                 1540                 1545

Pro Val  Cys Gln Asp His Leu  Glu Phe Trp Glu Gly  Val Phe Thr
    1550                 1555                 1560

Gly Leu  Thr His Ile Asp Ala  His Phe Leu Ser Gln  Thr Lys Gln
    1565                 1570                 1575

Ser Gly  Glu Asn Phe Pro Tyr  Leu Val Ala Tyr Gln  Ala Thr Val
    1580                 1585                 1590

Cys Ala  Arg Ala Gln Ala Pro  Pro Pro Ser Trp Asp  Gln Met Trp
    1595                 1600                 1605

Lys Cys  Leu Ile Arg Leu Lys  Pro Thr Leu His Gly  Pro Thr Pro
    1610                 1615                 1620

Leu Leu  Tyr Arg Leu Gly Ala  Val Gln Asn Glu Val  Thr Leu Thr
    1625                 1630                 1635

His Pro  Ile Thr Lys Tyr Ile  Met Thr Cys Met Ser  Ala Asp Leu
    1640                 1645                 1650

Glu Val  Val Thr Ser Thr Trp  Val Leu Val Gly Gly  Val Leu Ala
    1655                 1660                 1665

Ala Leu  Ala Ala Tyr Cys Leu  Ser Thr Gly Cys Val  Val Ile Val
    1670                 1675                 1680

Gly Arg  Ile Val Leu Ser Gly  Lys Pro Ala Ile Ile  Pro Asp Arg
    1685                 1690                 1695

Glu Val  Leu Tyr Gln Glu Phe  Asp Glu Met Glu Glu  Cys Ser Gln
    1700                 1705                 1710

His Leu  Pro Tyr Ile Glu Gln  Gly Met Met Leu Ala  Glu Gln Phe
    1715                 1720                 1725

Lys Gln  Lys Ala Leu Gly Leu  Leu Gln Thr Ala Ser  Arg His Ala
    1730                 1735                 1740

Glu Val  Ile Thr Pro Ala Val  Gln Thr Asn Trp Gln  Lys Leu Glu
    1745                 1750                 1755

Val Phe  Trp Ala Lys His Met  Trp Asn Phe Ile Ser  Gly Ile Gln
    1760                 1765                 1770

Tyr Leu  Ala Gly Leu Ser Thr  Leu Pro Gly Asn Pro  Ala Ile Ala
    1775                 1780                 1785

Ser Leu  Met Ala Phe Thr Ala  Ala Val Thr Ser Pro  Leu Thr Thr
    1790                 1795                 1800

Gly Gln  Thr Leu Leu Phe Asn  Ile Leu Gly Gly Trp  Val Ala Ala
    1805                 1810                 1815

Gln Leu  Ala Ala Pro Gly Ala  Ala Thr Ala Phe Val  Gly Ala Gly
    1820                 1825                 1830

Leu Ala  Gly Ala Ala Ile Gly  Ser Val Gly Leu Gly  Lys Val Leu
    1835                 1840                 1845

Val Asp  Ile Leu Ala Gly Tyr  Gly Ala Gly Val Ala  Gly Ala Leu
    1850                 1855                 1860

Val Ala  Phe Lys Ile Met Ser  Gly Glu Val Pro Ser  Thr Glu Asp
    1865                 1870                 1875

Leu Val  Asn Leu Leu Pro Ala  Ile Leu Ser Pro Gly  Ala Leu Val
    1880                 1885                 1890
```

```
Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Ala Ile Leu Ser Ser Leu Thr Val
    1940                1945                1950

Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp
    1970                1975                1980

Ile Cys Glu Val Leu Ser Asp Phe Lys Thr Trp Leu Lys Ala Lys
    1985                1990                1995

Leu Met Pro Gln Leu Pro Gly Ile Pro Phe Val Ser Cys Gln Arg
    2000                2005                2010

Gly Tyr Arg Gly Val Trp Arg Gly Asp Gly Ile Met His Thr Arg
    2015                2020                2025

Cys His Cys Gly Ala Glu Ile Thr Gly His Val Lys Asn Gly Thr
    2030                2035                2040

Met Arg Ile Val Gly Pro Arg Thr Cys Arg Asn Met Trp Ser Gly
    2045                2050                2055

Thr Phe Pro Ile Asn Ala Tyr Thr Thr Gly Pro Cys Thr Pro Leu
    2060                2065                2070

Pro Ala Pro Asn Tyr Lys Phe Ala Leu Trp Arg Val Ser Ala Glu
    2075                2080                2085

Glu Tyr Val Glu Ile Arg Arg Val Gly Asp Phe His Tyr Val Ser
    2090                2095                2100

Gly Met Thr Thr Asp Asn Leu Lys Cys Pro Cys Gln Ile Pro Ser
    2105                2110                2115

Pro Glu Phe Phe Thr Glu Leu Asp Gly Val Arg Leu His Arg Phe
    2120                2125                2130

Ala Pro Pro Cys Lys Pro Leu Leu Arg Glu Glu Val Ser Phe Arg
    2135                2140                2145

Val Gly Leu His Glu Tyr Pro Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Ala Ala Gly Arg Arg Leu Ala Arg Gly
    2180                2185                2190

Ser Pro Pro Ser Met Ala Ser Ser Ser Ala Ser Gln Leu Ser Ala
    2195                2200                2205

Pro Ser Leu Lys Ala Thr Cys Thr Ala Asn His Asp Ser Pro Asp
    2210                2215                2220

Ala Glu Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu Val Ala Glu Glu Asp Glu Arg Glu Val
    2255                2260                2265

Ser Val Pro Ala Glu Ile Leu Arg Lys Ser Arg Arg Phe Ala Arg
    2270                2275                2280

Ala Leu Pro Val Trp Ala Arg Pro Asp Tyr Asn Pro Pro Leu Val
```

-continued

```
    2285                2290                2295

Glu Thr  Trp Lys Lys Pro Asp  Tyr Glu Pro Pro Val  Val His Gly
    2300                2305                2310

Cys Pro  Leu Pro Pro Pro Arg  Ser Pro Pro Val Pro  Pro Pro Arg
    2315                2320                2325

Lys Lys  Arg Thr Val Val Leu  Thr Glu Ser Thr Leu  Ser Thr Ala
    2330                2335                2340

Leu Ala  Glu Leu Ala Thr Lys  Ser Phe Gly Ser Ser  Ser Thr Ser
    2345                2350                2355

Gly Ile  Thr Gly Asp Asn Thr  Thr Thr Ser Ser Glu  Pro Ala Pro
    2360                2365                2370

Ser Gly  Cys Pro Pro Asp Ser  Asp Val Glu Ser Tyr  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Ser  Gly Ala Asp Thr Glu  Asp Val Val
    2405                2410                2415

Cys Cys  Ser Met Ser Tyr Ser  Trp Thr Gly Ala Leu  Val Thr Pro
    2420                2425                2430

Cys Ala  Ala Glu Glu Gln Lys  Leu Pro Ile Asn Ala  Leu Ser Asn
    2435                2440                2445

Ser Leu  Leu Arg His His Asn  Leu Val Tyr Ser Thr  Thr Ser Arg
    2450                2455                2460

Ser Ala  Cys Gln Arg Gln Lys  Lys Val Thr Phe Asp  Arg Leu Gln
    2465                2470                2475

Val Leu  Asp Ser His Tyr Gln  Asp Val Leu Lys Glu  Val Lys Ala
    2480                2485                2490

Ala Ala  Ser Lys Val Lys Ala  Asn Leu Leu Ser Val  Glu Glu Ala
    2495                2500                2505

Cys Ser  Leu Thr Pro Pro His  Ser Ala Lys Ser Lys  Phe Gly Tyr
    2510                2515                2520

Gly Ala  Lys Asp Val Arg Cys  His Ala Arg Lys Ala  Val Ala His
    2525                2530                2535

Ile Asn  Ser Val Trp Lys Asp  Leu Leu Glu Asp Ser  Val Thr Pro
    2540                2545                2550

Ile Asp  Thr Thr Ile Met Ala  Lys Asn Glu Val Phe  Cys Val Gln
    2555                2560                2565

Pro Glu  Lys Gly Gly Arg Lys  Pro Ala Arg Leu Ile  Val Phe Pro
    2570                2575                2580

Asp Leu  Gly Val Arg Val Cys  Glu Lys Met Ala Leu  Tyr Asp Val
    2585                2590                2595

Val Ser  Lys Leu Pro Leu Ala  Val Met Gly Ser Ser  Tyr Gly Phe
    2600                2605                2610

Gln Tyr  Ser Pro Gly Gln Arg  Val Glu Phe Leu Val  Gln Ala Trp
    2615                2620                2625

Lys Ser  Lys Lys Thr Pro Met  Gly Phe Ser Tyr Asp  Thr Arg Cys
    2630                2635                2640

Phe Asp  Ser Thr Val Thr Glu  Ser Asp Ile Arg Thr  Glu Glu Ala
    2645                2650                2655

Ile Tyr  Gln Cys Cys Asp Leu  Asp Pro Gln Ala Arg  Val Ala Ile
    2660                2665                2670

Lys Ser  Leu Thr Glu Arg Leu  Tyr Val Gly Gly Pro  Leu Thr Asn
    2675                2680                2685
```

-continued

```
Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Asn Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Thr Ala Ala Gly Arg Leu Asp Leu Ser Gly Trp Phe Thr Ala
    2960                2965                2970

Gly Tyr Ser Gly Gly Asp Ile Tyr His Ser Val Ser His Ala Arg
    2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
    3005                3010
```